United States Patent
Thudium et al.

(10) Patent No.: US 11,512,130 B2
(45) Date of Patent: *Nov. 29, 2022

(54) HUMAN ANTIBODIES THAT BIND LYMPHOCYTE ACTIVATION GENE-3 (LAG-3), AND USES THEREOF

(71) Applicant: E.R. Squibb & Sons, L.L.C., Princeton, NJ (US)

(72) Inventors: Kent B. Thudium, Oakland, CA (US); Mark J. Selby, San Francisco, CA (US); Kyra D. Zens, San Mateo, CA (US); Mark Yamanaka, Pleasanton, CA (US); Alan J. Korman, Piedmont, CA (US); Heidi N. Leblanc, Mountain View, CA (US)

(73) Assignee: E.R. Squibb & Sons, L.L.C., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/544,542

(22) Filed: Dec. 7, 2021

(65) Prior Publication Data

US 2022/0204612 A1 Jun. 30, 2022

Related U.S. Application Data

(60) Continuation of application No. 17/226,624, filed on Apr. 9, 2021, now Pat. No. 11,236,165, which is a continuation of application No. 16/999,488, filed on Aug. 21, 2020, now Pat. No. 11,001,630, which is a continuation of application No. 16/419,938, filed on May 22, 2019, now Pat. No. 10,988,535, which is a division of application No. 15/730,363, filed on Oct. 11, 2017, now Pat. No. 10,344,089, which is a division of application No. 13/058,492, filed as application No. PCT/US2009/053405 on Aug. 11, 2009, now abandoned.

(60) Provisional application No. 61/188,548, filed on Aug. 11, 2008.

(51) Int. Cl.
*A61K 39/00* (2006.01)
*C07K 16/28* (2006.01)

(52) U.S. Cl.
CPC ...... *C07K 16/2803* (2013.01); *C07K 16/2827* (2013.01); *A61K 2039/505* (2013.01); *A61K 2039/507* (2013.01); *C07K 2317/21* (2013.01); *C07K 2317/34* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,545,806 A | 8/1996 | Lonberg et al. |
| 5,773,578 A | 6/1998 | Hercend et al. |
| 5,811,097 A | 9/1998 | Allison et al. |
| 5,874,250 A | 2/1999 | Hercend et al. |
| 5,976,877 A | 11/1999 | Hercend et al. |
| 6,143,273 A | 11/2000 | Faure et al. |
| 6,197,524 B1 | 3/2001 | Romagnani |
| 6,207,156 B1 | 3/2001 | Kuchroo et al. |
| 6,482,925 B1 | 11/2002 | El Tayar et al. |
| 6,500,422 B2 | 12/2002 | Biffoni |
| RE38,313 E | 11/2003 | Faure et al. |
| 6,808,710 B1 | 10/2004 | Wood et al. |
| 7,138,501 B2 | 11/2006 | Ruben et al. |
| 7,306,906 B2 | 12/2007 | Maruyama et al. |
| 7,329,737 B2 | 2/2008 | Sexton et al. |

(Continued)

FOREIGN PATENT DOCUMENTS

| | | |
|---|---|---|
| WO | WO-9110682 A1 | 7/1991 |
| WO | WO-9530750 A2 | 11/1995 |

(Continued)

OTHER PUBLICATIONS

Adib-Conquy, M., et al., "Effect of Amino Acid Substitutions in the Heavy Chain CDR3 of an Autoantibody on Its Reactivity," International Immunology 10(3):341-346, Oxford University Press, England (1998).

(Continued)

*Primary Examiner* — Michail A Belyavskyi
(74) *Attorney, Agent, or Firm* — Sterne, Kessler, Goldstein & Fox P.L.L.C.

(57) ABSTRACT

The present disclosure provides isolated monoclonal antibodies that specifically bind to LAG-3 with high affinity, particularly human monoclonal antibodies. Preferably, the antibodies bind human LAG-3. In certain embodiments, the antibodies bind both human and monkey LAG-3 but do not bind mouse LAG-3. The invention provides anti-LAG-3 antibodies that can inhibit the binding of LAG-3 to MHC Class II molecules and that can stimulate antigen-specific T cell responses. Nucleic acid molecules encoding the antibodies of the invention, expression vectors, host cells and methods for expressing the antibodies of the invention are also provided. Immunoconjugates, bispecific molecules and pharmaceutical compositions comprising the antibodies of the invention are also provided. This disclosure also provides methods for detecting LAG-3, as well as methods for treating stimulating immune responses using an anti-LAG-3 antibody of the invention. Combination therapy, in which an anti-LAG-3 antibody is co-administered with at least one additional immunostimulatory antibody, is also provided.

22 Claims, 26 Drawing Sheets

Specification includes a Sequence Listing.

(56) References Cited

U.S. PATENT DOCUMENTS

| | | |
|---|---|---|
| 7,563,441 B2 | 7/2009 | Graus et al. |
| 7,595,048 B2 | 9/2009 | Honjo et al. |
| 7,605,238 B2 | 10/2009 | Korman et al. |
| 7,790,160 B2 | 9/2010 | Von Strandmann et al. |
| 7,850,965 B2 | 12/2010 | Jensen et al. |
| 7,943,743 B2 | 5/2011 | Korman et al. |
| 8,008,449 B2 | 8/2011 | Korman et al. |
| 8,168,179 B2 | 5/2012 | Honjo et al. |
| 8,383,796 B2 | 2/2013 | Korman et al. |
| 8,476,419 B2 | 7/2013 | Thielemans |
| 8,551,481 B2 | 10/2013 | Pardoll et al. |
| 8,728,474 B2 | 5/2014 | Honjo et al. |
| 8,779,105 B2 | 7/2014 | Korman et al. |
| 9,005,629 B2 | 4/2015 | Pardoll et al. |
| 9,067,999 B1 | 6/2015 | Honjo et al. |
| 9,073,994 B2 | 7/2015 | Honjo et al. |
| 9,084,776 B2 | 7/2015 | Korman et al. |
| 9,102,725 B2 | 8/2015 | Korman et al. |
| 9,212,224 B2 | 12/2015 | Cogswell et al. |
| 9,273,135 B2 | 3/2016 | Korman et al. |
| 9,358,289 B2 | 6/2016 | Korman et al. |
| 9,387,247 B2 | 7/2016 | Korman et al. |
| 9,393,301 B2 | 7/2016 | Honjo et al. |
| 9,402,899 B2 | 8/2016 | Honjo et al. |
| 9,439,962 B2 | 9/2016 | Honjo et al. |
| 9,492,539 B2 | 11/2016 | Korman et al. |
| 9,492,540 B2 | 11/2016 | Korman et al. |
| 9,505,839 B2 | 11/2016 | Lonberg et al. |
| 9,580,505 B2 | 2/2017 | Korman et al. |
| 9,580,507 B2 | 2/2017 | Korman et al. |
| 9,856,320 B2 | 1/2018 | Cogswell |
| 10,072,082 B2 | 9/2018 | Cogswell |
| 10,138,299 B2 | 11/2018 | Cogswell |
| 10,266,591 B2 | 4/2019 | Lonberg et al. |
| 10,266,594 B1 | 4/2019 | Cogswell |
| 10,266,595 B2 | 4/2019 | Cogswell |
| 10,266,596 B1 | 4/2019 | Cogswell |
| 10,308,714 B2 | 6/2019 | Cogswell |
| 10,316,090 B2 | 6/2019 | Cogswell |
| 10,316,091 B2 | 6/2019 | Cogswell |
| 10,323,092 B2 | 6/2019 | Cogswell |
| 10,323,093 B2 | 6/2019 | Cogswell |
| 10,344,089 B2 | 7/2019 | Thudium |
| 10,358,495 B2 | 7/2019 | Ullman et al. |
| 10,377,824 B2 | 8/2019 | Lonberg et al. |
| 10,441,655 B2 | 10/2019 | Korman et al. |
| 10,577,423 B2 | 3/2020 | Cogswell et al. |
| 10,584,170 B2 | 3/2020 | Cogswell et al. |
| 10,604,575 B2 | 3/2020 | Cogswell et al. |
| 10,988,535 B2 | 4/2021 | Thudium |
| 10,988,536 B2 | 4/2021 | Thudium |
| 11,001,630 B2 | 5/2021 | Thudium |
| 2002/0086014 A1 | 7/2002 | Korman et al. |
| 2002/0146753 A1 | 10/2002 | Ditzel et al. |
| 2003/0059937 A1 | 3/2003 | Ruben et al. |
| 2003/0129601 A1 | 7/2003 | Cole |
| 2004/0072164 A1 | 4/2004 | Maruyama et al. |
| 2004/0171551 A1 | 9/2004 | Triebel |
| 2005/0009136 A1 | 1/2005 | Nixon et al. |
| 2005/0226876 A1 | 10/2005 | Graus et al. |
| 2006/0083744 A1 | 4/2006 | Chen et al. |
| 2006/0110383 A1 | 5/2006 | Honjo et al. |
| 2006/0177442 A1 | 8/2006 | Von Strandmann et al. |
| 2006/0240024 A1 | 10/2006 | Pardoll et al. |
| 2007/0004910 A1 | 1/2007 | Sexton et al. |
| 2007/0160598 A1 | 7/2007 | Dennis et al. |
| 2008/0038264 A1 | 2/2008 | Bodary et al. |
| 2008/0069822 A1 | 3/2008 | Jensen et al. |
| 2008/0260641 A1 | 10/2008 | Teeling et al. |
| 2008/0279865 A1 | 11/2008 | Gomez-Navarro |
| 2009/0055944 A1 | 2/2009 | Korman et al. |
| 2009/0217401 A1 | 8/2009 | Korman et al. |
| 2009/0252741 A1 | 10/2009 | Liu |
| 2009/0297518 A1 | 12/2009 | Honjo et al. |
| 2010/0233183 A1 | 9/2010 | Triebel et al. |
| 2011/0081341 A1 | 4/2011 | Honjo et al. |
| 2011/0150892 A1 | 6/2011 | Thudium et al. |
| 2011/0209230 A1 | 8/2011 | Korman et al. |
| 2013/0122014 A1 | 5/2013 | Korman et al. |
| 2013/0133091 A1 | 5/2013 | Korman et al. |
| 2013/0309250 A1 | 11/2013 | Cogswell et al. |
| 2014/0212422 A1 | 7/2014 | Korman et al. |
| 2014/0271684 A1 | 9/2014 | Li |
| 2014/0294852 A1 | 10/2014 | Korman et al. |
| 2014/0314714 A1 | 10/2014 | Honjo et al. |
| 2014/0328833 A1 | 11/2014 | Korman et al. |
| 2014/0348743 A1 | 11/2014 | Korman et al. |
| 2015/0093380 A1 | 4/2015 | Honjo et al. |
| 2015/0125463 A1 | 5/2015 | Cogswell et al. |
| 2015/0165025 A1 | 6/2015 | Korman et al. |
| 2015/0197572 A1 | 7/2015 | Honjo et al. |
| 2015/0307609 A1 | 10/2015 | Lonberg et al. |
| 2015/0337038 A1 | 11/2015 | Korman et al. |
| 2016/0075782 A1 | 3/2016 | Korman et al. |
| 2016/0090417 A1 | 3/2016 | Cogswell et al. |
| 2016/0108121 A1 | 4/2016 | Pardoll et al. |
| 2016/0158355 A1 | 6/2016 | Honjo et al. |
| 2016/0158356 A1 | 6/2016 | Honjo et al. |
| 2016/0362495 A1 | 12/2016 | Korman et al. |
| 2017/0051060 A1 | 2/2017 | Honjo et al. |
| 2017/0088615 A1 | 3/2017 | Korman |
| 2017/0137514 A1 | 5/2017 | Lonberg et al. |
| 2017/0143827 A1 | 5/2017 | Vikram et al. |
| 2017/0158767 A1 | 6/2017 | Korman et al. |
| 2018/0066054 A1 | 3/2018 | Thudium |
| 2018/0282414 A1 | 6/2018 | Cogswell |
| 2018/0273624 A1 | 9/2018 | Cogswell |
| 2018/0282413 A1 | 10/2018 | Cogswell |
| 2018/0312590 A1 | 11/2018 | Cogswell |
| 2018/0319887 A1 | 11/2018 | Cogswell |
| 2019/0092863 A1 | 3/2019 | Cogswell |
| 2019/0100589 A1 | 4/2019 | Cogswell |
| 2019/0100590 A1 | 4/2019 | Cogswell |
| 2019/0112376 A1 | 4/2019 | Cogswell |
| 2019/0112377 A1 | 4/2019 | Cogswell |
| 2019/0135920 A1 | 5/2019 | Cogswell |
| 2019/0153099 A1 | 5/2019 | Cogswell |
| 2019/0256594 A1 | 8/2019 | Lonberg et al. |
| 2019/0276538 A1 | 9/2019 | Thudium |
| 2019/0276539 A1 | 9/2019 | Thudium |
| 2020/0062846 A1 | 2/2020 | Honjo et al. |
| 2020/0062848 A1 | 2/2020 | Korman et al. |
| 2020/0138945 A1 | 5/2020 | Korman et al. |
| 2020/0231671 A1 | 7/2020 | Thudium |
| 2020/0308282 A1 | 10/2020 | Cogswell et al. |
| 2020/0385466 A1 | 12/2020 | Thudium |
| 2020/0385467 A1 | 12/2020 | Thudium |
| 2021/0261660 A1 | 8/2021 | Thudium |
| 2021/0261661 A1 | 8/2021 | Thudium |
| 2021/0261662 A1 | 8/2021 | Thudium |

FOREIGN PATENT DOCUMENTS

| | | |
|---|---|---|
| WO | WO-9703695 A1 | 2/1997 |
| WO | WO-9842752 A1 | 10/1998 |
| WO | WO-9858059 A1 | 12/1998 |
| WO | WO-0037504 A2 | 6/2000 |
| WO | WO-0069914 A2 | 11/2000 |
| WO | WO-0114424 A2 | 3/2001 |
| WO | WO-200243478 A2 | 6/2002 |
| WO | WO-03088808 A2 | 10/2003 |
| WO | WO-2004004771 A1 | 1/2004 |
| WO | WO-2004039956 A2 | 5/2004 |
| WO | WO-2004078928 A1 | 9/2004 |
| WO | WO-2005034733 A2 | 4/2005 |
| WO | WO-2006007850 A1 | 1/2006 |
| WO | WO-2006121168 A1 | 11/2006 |
| WO | WO-2006133396 A2 | 12/2006 |
| WO | WO-2007005874 A2 | 1/2007 |
| WO | WO-2008007648 A1 | 1/2008 |
| WO | WO-2008073160 A2 | 6/2008 |
| WO | WO-2008132601 A1 | 11/2008 |
| WO | WO-2010019570 A2 | 2/2010 |

(56) References Cited

FOREIGN PATENT DOCUMENTS

| WO | WO-2013173223 A1 | 11/2013 |
| WO | WO-2016168716 A1 | 11/2013 |
| WO | WO-2014008218 A1 | 1/2014 |

OTHER PUBLICATIONS

Baixeras, E., et al., "Characterization of the Lymphocyte Activation Gene 3-encoded Protein. A New Ligand for Human Leukocyte Antigen Class II Antigens," The Journal of Experimental Medicine 176(2):327-337, Rockefeller University Press, United States (1992).

Beers, R., et al., "Immunotoxins With Increased Activity Against Epidermal Growth Factor Receptor vIII-expressing Cells Produced by Antibody Phage Display," Clinical Cancer Research 6(7):2835-2843, The Association, United States (2000).

Blackburn, S.D., et al., "Coregulation of CD8+ T cell exhaustion by multiple inhibitory receptors during chronic viral infection," Nature Immunology 10(1):29-37, Nature America Inc., United States (Jan. 2009).

Brummell, D.A., et al., "Probing the Combining Site of an Anti-Carbohydrate Antibody by Saturation-Mutagenesis: Role of the Heavy-Chain CDR3 Residues," Biochemistry 32(4):1180-1187, American Chemical Society, United States (1993).

Camacho, L.H., et al., "Phase I clinical trial of anti-CTLA4 human monoclonal antibody CP-675,206 in patients (pts) with advanced solid malignancies," Journal of Clinical Oncology 22(14S):Abstract 2505, 2004 ASCO Annual Meeting Proceedings (Post-Meeting Edition), 40$^{th}$ Annual Meeting, Jun. 5-8, New Orleans, LA, American Society of Clinical Oncology, United States (2004).

Casati, C., et al., "Soluble Human LAG-3 Molecule Amplifies the In vitro Generation of Type 1 Tumor-Specific Immunity," Cancer Research 66(8):4450-4460, American Association for Cancer Research, United States (2006).

De Pascalis, R., et al., "Grafting of 'Abbreviated' Complementarity-Determining Regions Containing Specificity-determining Residues Essential for Ligand Contact to Engineer a Less Immunogenic Humanized Monoclonal Antibody," Journal of Immunology 169(6):3076-3084, The American Association of Immunologists, United States (2002).

De Wildt, R.M.T., et al. , "Heavy Chain CDR3 Optimization of a Germline Encoded Recombinant Antibody Fragment Predisposed to Bind the U1A Protein," Protein Engineering 10(7):835-841, Oxford University Press, England (1997).

Drake, C.G., et al., "Blocking the Regulatory T Cell Molecule LAG-3 Augments in Vivo Anti-tumor Immunity in an Autochthonous Model of Prostate Cancer," Journal of Clinical Oncology 24(18):2573 (2006).

El Mir, S. and Triebel, F., "A Soluble Lymphocyte Activation Gene-3 Molecule Used as a Vaccine Adjuvant Elicits Greater Humoral and Cellular Immune Responses to Both Particulate and Soluble Antigens," Journal of Immunology 164(11):5583-5589, American Association of Immunologists, United States (2000).

Extended European Search Report for EP Application No. 09807162.4, European Patent Office, Netherlands, dated Dec. 21, 2012, 9 pages.

Fishwild, D.M., et al., "High-Avidity Human IgGK Monoclonal Antibodies from a Novel Strain of Minilocus Transgenic Mice," Nature Biotechnology 14(7):845-851, Nature Publishing Group, United States (1996).

Greenberg, P.D. and Riddell, S.R., "Deficient Cellular Immunity-Finding and Fixing the Defects," Science 285(5427):546-551, American Association for the Advancement of Science, United States (1999).

Grosso, J.F., et al., "Functionally Distinct LAG-3 and PD-1 Subsets on Activated and Chronically Stimulated CD8 T Cells," The Journal of Immunology 182(11):6659-6669, The American Association of Immunologists, Inc., United States (Jun. 2009).

Grosso, J.F., et al., "LAG-3 Regulates CD8+ T Cell Accumulation and Effector Function in Murine Self- and Tumor-tolerance Systems," The Journal of Clinical Investigation 117(11):3383-3392, American Society for Clinical Investigation, United States (2007).

Hahne, M., et al., "Melanoma Cell Expression of Fas(Apo-1/CD95) Ligand: Implications for Tumor Immune Escape," Science 274(5291):1363-1366, American Association for the Advancement of Science, United States (1996).

Hall, B.L., et al., "A Single Amino Acid Mutation in CDR3 of the 3-14-9 L Chain Abolished Expression of the IDA 10-defined Idiotope and Antigen Binding," Journal of Immunology 149(5):1605-1612, American Association of Immunologists, United States (1992).

He, Y-F., et al., "Blocking Programmed Death-1 Ligand-PD-1 Interactions by Local Gene Therapy Results in Enhancement of Antitumor Effect of Secondary Lymphoid Tissue Chemokine," The Journal of Immunology 173(8):4919-4928, The American Association of Immunologists, United States (2004).

Holliger, P., et al., "'Diabodies': Small Bivalent and Bispecific Antibody Fragments," Proceedings of the National Academy of Sciences USA 90(14):6444-6448, National Academy of Sciences, United States (1993).

Howard, M. and Ogarra, A., "Biological Properties of Interleukin 10," Immunology Today 13(6):198-200, Elsevier Science Publishers, England (1992).

Huang, C-T., et al., "Role of LAG-3 in Regulatory T Cells," Immunity 21(4):503-513, Cell Press, United States (2004).

Huard, B., et al., "Characterization of the Major Histocompatibility Complex Class II Binding Site on LAG-3 Protein," Proceedings of the National Academy of Sciences of the United States of America 94(11):5744-5749, National Academy of Sciences, United States (1997).

Huard, B., et al., "Cellular expression and tissue distribution of the human LAG-3-encoded protein, an MHC class II ligand," Immunogenetics 39:213-217, Springer-Verlag, Germany (1994).

Huard, B., et al., "Lymphocyte-activation Gene 3/major Histocompatibility Complex Class II Interaction Modulates the Antigenic Response of CD4+ T Lymphocytes," European Journal of Immunology 24(12):3216-3221, Wiley-VCH, Germany (1994).

Huard, B., et al., "T Cell Major Histocompatibility Complex Class II Molecules Down-regulate CD4+ T Cell Clone Responses Following LAG-3 Binding," European Journal of Immunology 26(5):1180-1186, Wiley-VCH, Germany (1996).

Hurwitz, A.A., et al., "CTLA-4 Blockade Synergizes With Tumor-derived Granulocyte-macrophage Colony-stimulating Factor for Treatment of an Experimental Mammary Carcinoma," Proceedings of the National Academy of Sciences of the United States of America 95(17):10067-10071, National Academy of Sciences, United States (1998).

Hutloff, A., et al., "ICOS is an Inducible T-cell Co-stimulator Structurally and Functionally Related to CD28," Nature 397(6716):263-266, Nature Publishing Group, England (1999).

International Preliminary Report on Patentability and Written Opinion for Application No. PCT/US2009/053405, dated Feb. 15, 2011, 10 pages.

International Search Report for International Application No. PCT/US2009/053405, ISA/US Alexandria, Virginia, dated Mar. 31, 2010, 5 pages.

Iouzalen, N., et al., "LAP, A Lymphocyte Activation Gene-3 (LAG-3)-associated Protein That Binds to a Repeated EP Motif in the Intracellular Region of LAG-3, May Participate in the Down-regulation of the CD3/TCR Activation Pathway," European Journal of Immunology 31(10):2885-2891, Wiley-VCH, Germany (2001).

Ito, D., et al., "Effective Priming of Cytotoxic T Lymphocyte Precursors by Subcutaneous Administration of Peptide Antigens in Liposomes Accompanied by Anti-CD40 and Anti-CTLA-4 Antibodies," Immunobiology 201(5):527-540, Elsevier, Netherlands (2000).

Kehrl, J.H., et al., "Production of Transforming Growth Factor β by Human T Lymphocytes and Its Potential Role in the Regulation of T Cell Growth," The Journal of Experimental Medicine 163(5):1037-1050, Rockefeller University Press, United States (1986).

Kelley, R.F. and O'Connell, M.P., "Thermodynamic Analysis of an Antibody Functional Epitope," Biochemistry 32(27):6828-6835, American Chemical Society, United States (1993).

Kocak, E., et al., "Combination Therapy with Anti-CTL Antigen-4 and Anti-4-1BB Antibodies Enhances Cancer Immunity and Reduces

(56) References Cited

OTHER PUBLICATIONS

Autoimmunity," Cancer Research 66(14):7276-7284, American Association for Cancer Research, United States (2006).
Komissarov, A.A., et al., "Site-specific Mutagenesis of a Recombinant Anti-single-stranded DNA Fab. Role of Heavy Chain Complementarity-determining Region 3 Residues in Antigen Interaction," 272(43):26864-26870, American Society for Biochemistry and Molecular Biology, United States (1997).
Lonberg, N., et al., "Antigen-specific Human Antibodies from Mice Comprising Four Distinct Genetic Modifications," Nature 368(6474):856-859, Nature Publishing Group, United States (1994).
MacCallum, R.M., et al., "Antibody-antigen Interactions: Contact Analysis and Binding Site Topography," Journal of Molecular Biology 262(5):732-745, Academic Press, England (1996).
Macon-Lemaitre, L. and Triebel, F., "The Negative Regulatory Function of the Lymphocyte-activation Gene-3 Co-receptor (CD223) on Human T Cells," Immunology 115(2):170-178, Blackwell Scientific Publications, England (2005).
Melero, I., et al., "Monoclonal Antibodies Against the 4-1BB T-cell Activation Molecule Eradicate Established Tumors," Nature Medicine 3(6):682-685, Nature Publishing Company, United States (1997).
Mokyr, M.B., et al., "Realization of the Therapeutic Potential of CTLA-4 Blockade in Low-dose Chemotherapy-treated Tumor-bearing Mice," Cancer Research 58(23):5301-5304, American Association for Cancer Research, United States (1998).
Pardoll, D., "Chapter 14-Dendritic Cells and Coregulatory Signals: Immune Checkpoint Blockade to Stimulate Immunotherapy," Cancer Immunotherapy Immune Suppression and Tumor Growth, pp. 257-275, Elsevier Inc., United States (2007).
Poljak, R.J., "Production and Structure of Diabodies," Structure 2(12):1121-1123, Cell Press, United States (1994).
Prigent, P., et al., "Lymphocyte Activation Gene-3 Induces Tumor Regression and Antitumor Immune Responses," European Journal of Immunology 29(12):3867-3876, Wiley-VCH, Germany (1999).
Ridge J.P., et al., "A Conditioned Dendritic Cell Can be a Temporal Bridge Between a CD4+ T-helper and a T-killer Cell," Nature 393(6684):474-478, Nature Publishing Group, England (1998).
Subramanyam, M., et al., "Soluble Human Lymphocyte Activation Gene-3 Modulates Allospecific T Cell Responses," International Immunology 10(5):679-689, University Press, England (1998).
Triebel, F., et al., "LAG-3, A Novel Lymphocyte Activation Gene Closely Related to CD4," The Journal of Experimental Medicine 171(5):1393-1405, Rockefeller University Press, United States (1990).
Triebel, F., "LAG-3: A Regulator of T-cell and DC Responses and its Use in Therapeutic Vaccination," Trends in Immunology 24(12):619-622, Elsevier Science Ltd., England (2003).
Weinberg, A.D., et al., "Engagement of the OX-40 Receptor in Vivo Enhances Antitumor Immunity," Journal of Immunology 164(4):2160-2169, American Association of Immunologists, United States (2000).
Workman, C.J. and Vignali, D.A., "Negative Regulation of T Cell Homeostasis by Lymphocyte Activation Gene-3 (CD223)," Journal of Immunology 174(2):688-695, American Association of Immunologists, United States (2005).
Workman, C.J., et al., "Phenotypic Analysis of the Murine Cd4-related Glycoprotein, CD223 (LAG-3)," European Journal of Immunology 32(8):2255-2263, Wiley-VCH, Germany (2002).
Office Action, dated May 30, 2014, in U.S. Appl. No. 13/058,492, Thudium, et al., 371(c) date Feb. 10, 2011.
Office Action, dated Oct. 14, 2014, in U.S. Appl. No. 13/058,492, Thudium, et al., 371(c) date Feb. 10, 2011.
Office Action, dated Mar. 17, 2015, in U.S. Appl. No. 13/058,492, Thudium, et al., 371(c) date Feb. 10, 2011.
Office Action, dated Jul. 8, 2015, in U.S. Appl. No. 13/058,492, Thudium, et al., 371(c) date Feb. 10, 2011.
Examiner's Answer to Appeal Brief, mailed Feb. 13, 2017, in U.S. Appl. No. 13/058,492, Thudium, et al., 371(c) date Feb. 10, 2011.
Poirier, N., et al., "Antibody-mediated depletion of lymphocyte-activation gene-3 (LAG-3$^+$)-activated T lymphocytes prevents delayed-type hypersensitivity in non-human primates" Clinical and Experimental Immunology 164(2):265-274, British Society for Immunology (2011).
Woo, S-R., et al., "Immune inhibitory molecules LAG-3 and PD-1 synergistically regulate T-cell function to promote tumoral immune escape" Cancer Research 72(4):917-927, American Association for Cancer Research (2011).
Kallewaard, N.L., et al., "Functional Maturation of the Human Antibody Response to Rotavirus," Journal of Immunology 180(6):3980-3989, American Association of Immunologists, United States (Mar. 2008).
Wiens, G.D., et al., "Somatic Mutation in VH complementarity-determining Region 2 and Framework Region 2: Differential Effects on Antigen Binding and Ig selection," Journal of Immunology 159(3):1293-1302, American Association of Immunologists, United States (1997).
Office Action, dated Jun. 6, 2018, in U.S. Appl. No. 15/730,363, Thudium, et al., filed Oct. 11, 2017, 6 pages.
Office Action, dated Nov. 20, 2018 in U.S. Appl. No. 15/730,363, Thudium, et al., filed Oct. 11, 2017, 7 pages.
Office Action dated Jun. 10, 2019, in U.S. Appl. No. 16/419,940, Thudium, et al., filed May 22, 2019, 7 pages.
Office Action, dated Jul. 25, 2019, in U.S. Appl. No. 13/058,492, Thudium, et al., 371(c) date Feb. 10, 2011, 8 pages.
Khan, T., et al., "Adjustable locks and flexible Keys: Plasticity of Epitope-Paratope Interactions in Germline Antibodies," J Immunol 192:5398-5405, American Association of Immunologists, United States (2014).
Torres, Marcela, et al., "The Immunoglobulin constant region contributes to affinity and specificity," Trends in Immunology 29(2): 91-97, Elsevier, Netherlands (2007).
Poosarla, V.G., et al., "Computational De Novo Design of Antibodies Binding to a Peptide With High Affinity," Biotechnology and Bioengineering 114(6):1331-1342, Wiley Online Library, United States (2017).
Edwards, B.M., et al., "The Remarkable Flexibility of the Human Antibody Repertoire; Isolation of Over One Thousand Different Antibodies to a Single Protein," J. Mol. Biol. 334:103-118, Elsevier, Netherlands (2003).
Barber, D.L., et al., "Restoring function in exhausted CD8 T cells during chronic viral infection," Nature 439:682-687, Nature Publishing Group, United Kingdom (2006).
Declaration of Jeanette L. Fairhurst in Grounds of Opposition mailed Aug. 20, 2020 in EP Application No. 1516647.8, European Patent Office, Germany, 12 pages.
Dyrberg, T., et al., "Peptides as antigens. Importance of orientation," The Journal of Experimental Medicine 164(4):1344-1349, Rockefeller University Press, United States (1986).
Exhibit 1 in Grounds of Opposition mailed Aug. 20, 2020, in EP Application No. 15156647.8, European Patent Office, Germany, 1 page.
Extended European Search Report dated Jul. 13, 2015, in EP Application No. 15156647.8, European Patent Office, Germany, 9 pages.
Goldberg, M.V., et al., "LAG-3 in Cancer Immunotherapy," Curr Top Microbiol Immunology 344:269-278, Springer, United States (2011).
Grounds of Opposition mailed Aug. 20, 2020, in EP Application No. 1516647.8, European Patent Office, Germany, 86 pages.
Hong, S., et al., "Progress and Application of Humanization of Monoclonal Antibodies," Chinese Journal of Biologicals 21(1):70-73, Changchun Institute of Biological Products, China (2008).
Hoogenboom, H.R., et al., "Designing and optimizing library selection strategies for generating high-affinity antibodies," TibTech Library 15:62-70, Elsevier, Netherlands (1997).
Huard, B., et al., "CD4/major histocompatibility complex class II interaction analyzed with CD4- and lymphocyte activation gene-3 (LAG-3)-Ig fusion proteins," Eur. J. Immunol.25:2718-2721, Wiley-VCH, Germany (1995).
Huard, B., et al., "LAG-3 does not define a specific mode of natural killing in human," Immunology Letters 61:109-112, Elsevier, Netherlands (1998).

(56) References Cited

OTHER PUBLICATIONS

Imakiire, T., et al., "Generation, immunologic characterization and antitumor effects of human monoclonal antibodies for carcinoembryonic antigen," Int J Cancer 108(4):564-570, Wiley Online Publishing, United States (2004).

Jespers, L.S., et al., "Guiding the Selection of Human Antibodies from Phage Display Reperotires to a Single Epitope of an Antigen," Biotechnology 12:899-903, Nature Publishing Group, United Kingdom (1994).

Kaufmann, D.E., et al., "Upregulation of CTLA-4 by HIV-specific CD4+ T cells correlates with disease progression and defines a reversible immune dysfunction," Nature Immunology 8(11):1246-1254, Nature Publishing Group, United Kingdom (2007).

Office Action dated Aug. 17, 2020, in U.S. Appl. No. 16/419,940, inventor Thudium, Kent B., et al., filed May 22, 2019, 8 pages.

Response to communication in European Patent Application No. 15156647.8, dated Mar. 29, 2018, European Patent Office, Germany, 3 pages.

Response to communication in European Patent Application No. 15156647.8, dated Feb. 9, 2016, European Patent Office, Germany, 3 pages.

Perez De La Lastra, J.M., et al., "Epitope mapping of 10 monoclonal antibodies against the pig analogue of human membrane cofactor protein (MCP)," Immunology 96:663-670, Blackwell Science Ltd., United States (1999).

Shapira, M., et al., "Immunity and protection against influenza virus by synthetic peptide corresponding to antigenic sites of hemagglutinin," PNAS 81(8): 2461-2465, United States National Academy of Sciences, United States (1984).

Office Action dated Apr. 28, 2020 in CN 201710463804.9, State Intellectual Property Office of People's Republic of China, China, 8 pages.

Tanaka, T., et al., "Efficient generation of antibodies to oncoproteins by using synthetic peptide antigens," PNAS 82(10):3400-3404, United States National Academy of Sciences, United States (1985).

Workman, C.J., et al., "The CD4-related molecule, LAG-3 (CD223), regulates the expansion of activated T cells," Eur J. Immunol. 33(4):970-979, Wiley Online Library, United States (2003).

Office Action dated Oct. 24, 2019, in U.S. Appl. No. 16/419,938, Thudium, et al., filed May 22, 2019, 4 pages.

Office Action dated Jun. 21, 2019, in U.S. Appl. No. 16/419,938, Thudium, et al., filed May 22, 2019, 4 pages.

Office Action dated Nov. 19, 2020, in U.S. Appl. No. 16/999,463, Thudium, et al., filed Aug. 21, 2020, 4 pages.

Office Action dated Nov. 20, 2020, in U.S. Appl. No. 16/999,488, Thudium, et al., filed Aug. 21, 2020, 5 pages.

Office Action dated Jul. 14, 2021, in U.S. Appl. No. 17/226,609, Thudium, et al., filed Apr. 9, 2021, 5 pages.

Office Action dated Jul. 7, 2021, in U.S. Appl. No. 17/226,595, Thudium, et al., filed Apr. 9, 2021, 5 pages.

Proprietor's Response to the Communication of Notices of Opposition in European Patent Application No. 15156647.8, filed Mar. 4, 2021, with Auxiliary Requests, 73 pages.

Summons to Attend Oral Proceedings Pursuant to Rule 115(1) EPC in European Patent Application No. 15156647.8, mailed May 10, 2021, 26 pages.

Office Action dated Jul. 28, 2021 in U.S. Appl. No. 17/226,624, Thudium, et al., filed Apr. 9, 2021, 5 pages.

Proprietor's Response to Summons to Attend Oral Proceedings in European Patent No. 2905030 (Patent Application No. 15156647.8, filed Mar. 4, 2021), with Auxiliary Claim Requests 1-a to 7-b in marked-up and clean versions, D38, D39, and D40, 203 pages.

Opponent's Response to Summons to Attend Oral Proceedings in European Patent No. 2905030 (Patent Application No. 15156647.8, filed Mar. 4, 2021), with Annex 1, D41, D42, D43, and D44, 260 pages.

Anti-LAG3 25F7 VH

```
V segment:      4-34
D segment:      5-12
J segment:      JH5b
```

|     | Q | V | Q | L | Q | Q | W | G | A | G | L | L | K | P | S | E | T | L |
|-----|---|---|---|---|---|---|---|---|---|---|---|---|---|---|---|---|---|---|
| 1   | CAG | GTG | CAG | CTA | CAG | CAG | TGG | GGC | GCA | GGA | CTG | TTG | AAG | CCT | TCG | GAG | ACC | CTG |

CDR1
~~~~~~~~~~~~~~~~~~~~

|     | S | L | T | C | A | V | Y | G | G | S | F | S | D | Y | Y | W | N | W |
|-----|---|---|---|---|---|---|---|---|---|---|---|---|---|---|---|---|---|---|
| 55  | TCC | CTC | ACC | TGC | GCT | GTC | TAT | GGT | GGG | TCC | TTC | AGT | GAT | TAC | TAC | TGG | AAC | TGG |

CDR2

~~~~~~~~~~~~~~~~~~~~

|     | I | R | Q | P | P | G | K | G | L | E | W | I | G | E | I | N | H | N |
|-----|---|---|---|---|---|---|---|---|---|---|---|---|---|---|---|---|---|---|
| 109 | ATC | CGC | CAG | CCC | CCA | GGG | AAG | GGG | CTG | GAG | TGG | ATT | GGG | GAA | ATC | AAT | CAT | AAT |

CDR2
~~~~~~~~~~~~~~~~~~~~~~~~~~~~~~~~~~~~~~~~~~~~~~~~

|     | G | N | T | N | S | N | P | S | L | K | S | R | V | T | L | S | L | D |
|-----|---|---|---|---|---|---|---|---|---|---|---|---|---|---|---|---|---|---|
| 163 | GGA | AAC | ACC | AAC | TCC | AAC | CCG | TCC | CTC | AAG | AGT | CGA | GTC | ACC | CTA | TCA | CTA | GAC |

|     | T | S | K | N | Q | F | S | L | K | L | R | S | V | T | A | A | D | T |
|-----|---|---|---|---|---|---|---|---|---|---|---|---|---|---|---|---|---|---|
| 217 | ACG | TCC | AAG | AAC | CAG | TTC | TCC | CTG | AAG | CTG | AGG | TCT | GTG | ACC | GCC | GCG | GAC | ACG |

CDR3
~~~~~~~~~~~~~~~~~~~~~~~~~~~~~~~~~~~~~~~~~~~~~~~~

|     | A | V | Y | Y | C | A | F | G | Y | S | D | Y | E | Y | N | W | F | D |
|-----|---|---|---|---|---|---|---|---|---|---|---|---|---|---|---|---|---|---|
| 271 | GCT | GTG | TAT | TAC | TGT | GCG | TTT | GGA | TAT | AGT | GAC | TAC | GAG | TAC | AAC | TGG | TTC | GAC |

CDR3
~~~

|     | P | W | G | Q | G | T | L | V | T | V | S | S |
|-----|---|---|---|---|---|---|---|---|---|---|---|---|
| 325 | CCC | TGG | GGC | CAG | GGA | ACC | CTG | GTC | ACC | GTC | TCC | TCA |

FIGURE 1A

Anti-LAG3 25F7 VK

V segment:       L6
    J segment:       JK2

```
        E   I   V   L   T   Q   S   P   A   T   L   S   L   S   P   G   E
        R
1       GAA ATT GTG TTG ACA CAG TCT CCA GCC ACC CTG TCT TTG TCT CCA GGG GAA
        AGA

CDR1
                            ~~~~~~~~~~~~~~~~~~~~~~~~~~~~~~~~~~~~~~~~~~~~~
        A   T   L   S   C   R   A   S   Q   S   I   S   S   Y   L   A   W
        Y
55      GCC ACC CTC TCC TGC AGG GCC AGT CAG AGT ATT AGC AGC TAC TTA GCC TGG
        TAC

CDR2

~~~~~~~~~~~~~~~~~~~~
        Q   Q   K   P   G   Q   A   P   R   L   L   I   Y   D   A   S   N
        R
109     CAA CAG AAA CCT GGC CAG GCT CCC AGG CTC CTC ATC TAT GAT GCA TCC AAC
        AGG

CDR2
        ~~~~~~~~
        A   T   G   I   P   A   R   F   S   G   S   G   S   G   T   D   F
        T
163     GCC ACT GGC ATC CCA GCC AGG TTC AGT GGC AGT GGG TCT GGG ACA GAC TTC
        ACT

CDR3
        ~~~~~~~~
        L   T   I   S   S   L   E   P   E   D   F   A   V   Y   Y   C   Q
        Q
217     CTC ACC ATC AGC AGC CTA GAG CCT GAA GAT TTT GCA GTT TAT TAC TGT CAG
        CAG

CDR3
        ~~~~~~~~~~~~~~~~~~~~~~~~~~~~
        R   S   N   W   P   L   T   F   G   Q   G   T   N   L   E   I   K
271     CGT AGC AAC TGG CCT CTC ACT TTT GGC CAG GGG ACC AAC CTG GAG ATC AAA
```

FIGURE 1B

```
Anti-LAG3 26H10 VH

V segment:       3-33
    D segment:       6-19
    J segment:       JH6b

Q    V    Q    L    V    E    S    G    G    G    V    V    Q    P    G    R    S
    L
    1 CAG  GTG  CAG  CTG  GTG  GAG  TCT  GGG  GGA  GGC  GTG  GTC  CAG  CCT  GGG  AGG  TCC
      CTG

CDR1
                                                                          ~~~~~~~~~~~~~~~~~~
        R    L    S    C    A    A    S    G    F    T    F    S    S    Y    G    M    H
    W
   55 AGA  CTC  TCC  TGT  GCA  GCG  TCT  GGA  TTC  ACC  TTC  AGT  AGC  TAT  GGC  ATG  CAC
      TGG

CDR2

~~~~~~~~~~~~~~~~~~~~
        V    R    Q    A    P    G    K    G    L    E    W    V    A    V    I    W    Y
    D
  109 GTC  CGC  CAG  GCT  CCA  GGC  AAG  GGG  CTG  GAG  TGG  GTG  GCA  GTT  ATA  TGG  TAT
      GAT

CDR2
    ~~~~~~~~~~~~~~~~~~~~~~~~~~~~~~~~~~~~~~~~~~~~~~~~~~
        G    S    N    K    Y    Y    A    D    S    V    K    G    R    F    T    I    S
    R
  163 GGA  AGT  AAT  AAA  TAC  TAT  GCA  GAC  TCC  GTG  AAG  GGC  CGA  TTC  ACC  ATC  TCC
      AGA

D    N    S    K    N    T    L    Y    L    Q    M    N    S    L    R    A    E
    D
  217 GAC  AAT  TCC  AAG  AAC  ACG  CTG  TAT  CTG  CAA  ATG  AAC  AGC  CTG  AGA  GCC  GAG
      GAC

CDR3
    ~~~~~~~~~~~~~~~~~~~~~~~~~~~~~~~~~~~~~~~~~~~~
        T    A    V    Y    Y    C    A    R    E    W    A    V    A    S    W    D    Y
    G
  271 ACG  GCT  GTG  TAT  TAC  TGT  GCG  AGA  GAA  TGG  GCA  GTG  GCC  TCC  TGG  GAC  TAC
      GGT

CDR3
    ~~~~~~~~~~~~
        M    D    V    W    G    Q    G    T    T    V    T    V    S    S
  325 ATG  GAC  GTC  TGG  GGC  CAA  GGG  ACC  ACG  GTC  ACC  GTC  TCC  TCA
```

FIGURE 2A

Anti- LAG3 26H10 VK

```
V segment:     A27
J segment:     JK3
```

```
      E   I   V   L   T   Q   S   P   G   T   L   S   L   S   P   G   E
  R
  1 GAA ATT GTG TTG ACG CAG TCT CCA GGC ACC CTG TCT TTG TCT CCA GGG GAA
    AGA
                                              CDR1
                                         ~~~~~~~~~~~~~~~~~~~~~~~~~~~~~~~~~~~~~
      A   T   L   S   C   R   A   S   Q   S   V   S   S   S   Y   L   A
  W
 55 GCC ACC CTC TCC TGC AGG GCC AGT CAG AGT GTT AGC AGC AGC TAC TTA GCC
    TGG
                                                                   CDR2
    ~~~~~~~~~~~~~~~~~
      Y   Q   Q   K   P   G   Q   A   P   R   L   L   I   Y   G   A   S
  S
109 TAC CAG CAG AAA CCT GGC CAG GCT CCC AGG CTC CTC ATC TAT GGT GCA TCC
    AGC
        CDR2
    ~~~~~~~~~~~~
      R   A   T   G   I   P   D   R   F   S   G   S   G   S   G   T   D
  F
163 AGG GCC ACT GGC ATC CCA GAC AGG TTC AGT GGC AGT GGG TCT GGG ACA GAC
    TTC

CDR3
    ~~~
      T   L   T   I   S   R   L   E   P   E   D   F   A   V   Y   Y   C
  Q
217 ACT CTC ACC ATC AGC AGA CTG GAG CCT GAA GAT TTT GCA GTG TAT TAC TGT
    CAG
              CDR3
    ~~~~~~~~~~~~~~~~~~~~~~~~~~~~~~~~~
      Q   Y   G   S   S   P   F   T   F   G   P   G   T   K   V   D   I
  K
271 CAG TAT GGT AGC TCA CCA TTC ACT TTC GGC CCT GGG ACC AAA GTG GAT ATC
    AAA
```

FIGURE 2B

Anti-LAG3 25E3 VH

V segment:       3-20
    D segment:       ND
    J segment:       JH4b

```
        E   V   Q   L   V   E   S   G   G   G   V   V   R   P   G   G   S
    L
  1 GAG GTG CAG TTG GTG GAG TCT GGG GGA GGT GTG GTA CGG CCT GGG GGG TCC
    CTG

CDR 1
                                                              ~~~~~~~~~~~~~~~~~~~~
        R   L   S   C   A   A   S   G   F   T   F   D   D   Y   G   M   S
    W
 55 AGA CTC TCC TGT GCA GCC TCT GGA TTC ACC TTT GAT GAT TAT GGC ATG AGC
    TGG

CDR 2
    ~~~~~~~~~~~~~~~~~~~~
        V   R   Q   A   P   G   K   G   L   E   W   V   S   G   I   N   W
    N
109 GTC CGC CAA GCT CCA GGG AAG GGG CTG GAG TGG GTC TCT GGT ATT AAT TGG
    AAT

CDR 2
    ~~~~~~~~~~~~~~~~~~~~~~~~~~~~~~~~~~~~~~~~~~~~~~~~
        G   G   S   T   Y   Y   A   D   S   V   K   G   R   F   T   I   S
    G
163 GGT GGT AGC ACA TAT TAT GCA GAC TCT GTG AAG GGC CGA TTC ACC ATC TCC
    GGA

D   N   A   K   N   S   L   Y   L   Q   M   N   S   L   R   A   E
    D
217 GAC AAC GCC AAG AAC TCC CTG TAT CTG CAA ATG AAC AGT CTG AGA GCC GAG
    GAC

CDR 3
                                      ~~~~~~~~~~~~
        T   A   L   Y   Y   C   T   T   G   G   Y   W   G   Q   G   T   L
    V
271 ACG GCC TTG TAT TAC TGT ACC ACT GGG GGC TAC TGG GGC CAG GGA ACC CTG
    GTC

T   V   S   S
325 ACC GTC TCC TCA
```

FIGURE 3A

Anti-LAG3 25E3 VK

V segment:       L18
    J segment:       JK2

```
       A   I   Q   L   T   Q   S   P   S   S   L   S   A   S   V   G   D
       R
     1 GCC ATC CAG TTG ACC CAG TCT CCA TCC TCC CTG TCT GCA TCT GTA GGA GAC
       AGA

CDR 1
                              ~~~~~~~~~~~~~~~~~~~~~~~~~~~~~~~~~~~~~~~~~~~
       V   T   I   T   C   R   A   S   Q   G   I   R   S   A   L   A   W
       Y
    55 GTC ACC ATC ACT TGC CGG GCA AGT CAG GGC ATT AGG AGT GCT TTA GCC TGG
       TAT

CDR 2
       ~~~~~~~~~~~~~~~~~~~~~
       Q   Q   K   P   G   K   A   P   K   L   L   I   Y   D   A   S   S
       L
   109 CAG CAG AAA CCA GGG AAA GCT CCT AAG CTC CTG ATC TAT GAT GCC TCC AGT
       TTG

CDR 2
       ~~~~~~~~
       E   S   G   V   P   S   R   F   S   G   S   G   S   G   T   D   F
       T
   163 GAA AGT GGG GTC CCA TCA AGG TTC AGC GGC AGT GGA TCT GGG ACA GAT TTC
       ACT

CDR
       3

~~~~~~~~
       L   T   I   S   S   L   Q   P   E   D   F   A   T   Y   Y   C   Q
       Q
   217 CTC ACC ATC AGC AGC CTG CAG CCT GAA GAT TTT GCA ACT TAT TAC TGT CAA
       CAG

CDR 3
       ~~~~~~~~~~~~~~~~~~~~~~~~~~~~~
       F   N   S   Y   P   Y   T   F   G   Q   G   T   K   L   E   I   K
   271 TTT AAT AGT TAC CCG TAC ACT TTT GGC CAG GGG ACC AAG CTG GAG ATC AAA
```

FIGURE 3B

```
Anti-LAG3 8B7 VH

V segment:    4-34
  D segment:    3-9
  J segment:    JH5b

Q   V   Q   L   Q   Q   W   G   A   G   L   L   K   P   S   E   T
    L
  1 CAG GTG CAG CTA CAG CAG TGG GGC GCA GGA CTG TTG AAG CCA TCG GAA ACC
    CTG

CDR1
                                                                    ~~~~~~~~~~~~~~~~~~~~
       S   L   T   C   A   V   Y   G   G   S   F   S   G   Y   Y   W   S
    W
 55 TCC CTC ACC TGC GCT GTC TAT GGT GGG TCC TTC AGT GGT TAC TAC TGG AGC
    TGG

CDR2

~~~~~~~~~~~~~~~~~~~~
       I   R   Q   P   P   G   K   G   L   E   W   I   G   E   I   N   H
    R
109 ATC CGC CAG CCC CCA GGG AAG GGG CTG GAG TGG ATT GGG GAA ATC AAT CAT
    CGT

CDR2
    ~~~~~~~~~~~~~~~~~~~~~~~~~~~~~~~~~~~~~~~~~~~~
       G   N   T   N   C   N   P   S   L   K   S   R   V   T   I   S   G
    D
163 GGA AAC ACC AAC TGC AAC CCG TCC CTC AAG AGT CGA GTC ACC ATA TCA GGA
    GAT

T   S   K   K   Q   F   A   L   K   L   N   S   V   T   A   A   D
    T
217 ACG TCC AAG AAA CAG TTC GCC CTG AAG CTG AAC TCT GTG ACC GCC GCG GAC
    ACG

CDR3

~~~~~~~~~~~~~~~~~~~~~~~~~~~~~~~~~~~~~~~~~~~~
       A   V   Y   Y   C   A   R   G   Y   D   I   L   T   G   Y   Y   E
    D
271 GCT GTC TAT TAC TGT GCG AGA GGA TAC GAT ATT TTG ACT GGT TAT TAT GAG
    GAC

CDR3
    ~~~
       S   W   G   P   G   T   L   V   T   V   S   S
325 TCC TGG GGC CCG GGA ACC CTG GTC ACC GTC TCC TCA
```

FIGURE 4A

Anti-LAG3 8B7 VK

```
V segment:    L6
J segment:    JK4
```

```
      E   I   V   L   T   Q   S   P   A   T   L   S   L   S   P   G   E
  R
1   GAA ATT GTG TTG ACA CAG TCT CCA GCC ACC CTG TCT TTG TCT CCA GGG GAA
    AGA
```

```
                                              CDR1
                            ~~~~~~~~~~~~~~~~~~~~~~~~~~~~~~~~~~~~~~~~~~
      A   T   L   S   C   R   A   S   Q   S   V   S   S   Y   L   A   W
  Y
55  GCC ACC CTC TCC TGC AGG GCC AGT CAG AGT GTT AGC AGC TAC TTA GCC TGG
    TAC
```

```
                                                                  CDR2
    ~~~~~~~~~~~~~~~~~~~~
      Q   Q   K   P   G   Q   A   P   R   L   L   I   Y   N   A   S   N
  R
109 CAA CAG AAA CCT GGC CAG GCT CCC AGG CTC CTC ATC TAT AAT GCA TCC AAC
    AGG
```

```
      CDR2
    ~~~~~~~~
      A   T   G   I   P   A   R   F   S   G   S   G   S   G   T   D   F
  T
163 GCC ACT GGC ATC CCA GCC AGG TTC AGT GGC AGT GGG TCT GGG ACA GAC TTC
    ACT
```

```
      CDR3
    ~~~~~~~~
      L   T   I   S   S   L   E   P   E   D   F   A   V   Y   Y   C   Q
  Q
217 CTC ACC ATC AGC AGC CTA GAG CCT GAA GAT TTT GCA GTT TAT TAC TGT CAG
    CAG
```

```
              CDR3
    ~~~~~~~~~~~~~~~~~~~~~~~~~~~~
      R   S   N   W   P   L   T   F   G   G   G   T   K   V   E   I   K
271 CGT AGC AAC TGG CCG CTC ACT TTC GGC GGA GGG ACC AAG GTG GAG ATC AAA
```

FIGURE 4B

Anti- LAG3 11F2 VH

V segment:       1-24
    D segment:       2-15
    J segment:       JH4b

```
          T   H   D   Q   V   Q   L   V   Q   S   G   A   E   V   K   K   P
G
    1 ACC CAC GAC CAG GTC CAG CTG GTA CAG TCT GGG GCT GAG GTG AAG AAG CCT
      GGG

CDR 1
      ~~~~~~~~~~~
          A   S   V   K   V   S   C   K   V   S   G   Y   T   L   T   E   V
S
   55 GCC TCA GTG AAG GTC TCC TGC AAG GTT TCC GGA TAC ACC CTC ACT GAA GTA
      TCC

CDR 1                                                              CDR
                                                                         2
      ~~~~~~~
      ~~~~~~~
          M   H   W   V   R   Q   A   P   G   K   G   L   E   W   M   G   G
F
  109 ATG CAC TGG GTG CGA CAG GCT CCT GGA AAA GGG CTT GAG TGG ATG GGA GGT
      TTT

CDR 2
      ~~~~~~~~~~~~~~~~~~~~~~~~~~~~~~~~~~~~~~~~~~~~~~~~~~~~~~~~~~~~~~~~~~~
          D   P   E   D   G   E   T   I   Y   A   Q   K   F   Q   G   R   V
T
  163 GAT CCT GAA GAT GGT GAA ACA ATC TAC GCA CAG AAG TTC CAG GGC AGA GTC
      ACC

M   T   E   D   T   S   T   D   T   A   Y   M   E   L   S   S   L
R
  217 ATG ACC GAG GAC ACA TCT ACA GAC ACA GCC TAC ATG GAG CTG AGC AGC CTG
      AGA

CDR 3
      ~~~~~~~~~~~~~~~~~~~~~~~~~~~~~
          S   E   D   T   A   V   Y   Y   C   A   T   A   F   V   V   V   V
A
  271 TCT GAG GAC ACG GCC GTG TAT TAC TGT GCA ACA GCC TTT GTA GTG GTG GTA
      GCT

CDR 3
      ~~~~~~~~~~~~~~~~
          A   S   D   Y   W   G   Q   G   T   L   V   T   V   S   S
  325 GCT TCT GAC TAC TGG GGC CAG GGA ACC CTG GTC ACC GTC TCC TCA
```

FIGURE 5A

Anti-LAG3 11F2 VK

V segment:      L6
   J segment:      JK1

```
         E   I   V   L   T   Q   S   P   A   T   L   S   L   S   P   G   E
       R
     1 GAA ATT GTG TTG ACA CAG TCT CCA GCC ACC CTG TCT TTG TCT CCA GGG GAA
       AGA

CDR 1
                              ~~~~~~~~~~~~~~~~~~~~~~~~~~~~~~~~~~~~~~~~~~~~~
         A   T   L   S   C   R   A   S   Q   S   V   S   S   Y   L   A   W
       Y
    55 GCC ACC CTC TCC TGC AGG GCC AGT CAG AGT GTT AGC AGC TAC TTA GCC TGG
       TAC

CDR 2

~~~~~~~~~~~~~~~~~~~~~
         Q   Q   K   P   G   Q   A   P   R   L   L   I   Y   D   A   S   N
       R
   109 CAA CAG AAA CCT GGC CAG GCT CCC AGG CTC CTC ATC TAT GAT GCA TCC AAC
       AGG

CDR 2
       ~~~~~~~~
         A   T   G   I   P   A   R   F   S   G   S   G   S   G   T   D   F
       T
   163 GCC ACT GGC ATC CCA GCC AGG TTC AGT GGC AGT GGG TCT GGG ACA GAC TTC
       ACT

CDR
       3

~~~~~~~~
         L   T   I   S   S   L   E   P   E   D   F   A   V   Y   Y   C   Q
       Q
   217 CTC ACC ATC AGC AGC CTA GAG CCT GAA GAT TTT GCA GTT TAT TAC TGT CAG
       CAG

CDR 3
       ~~~~~~~~~~~~~~~~~~~~~~~~~~~~~
         R   S   N   W   P   W   T   F   G   Q   G   T   K   V   E   I   K
   271 CGT AGC AAC TGG CCG TGG ACG TTC GGC CAA GGG ACC AAG GTG AAA ATC AAA
```

FIGURE 5B

Anti-LAG3 17E5 VH

V segment:    3-33
    D segment:    2-2
    J segment:    JH4b

```
      Q   V   H   L   V   E   S   G   G   G   V   V   Q   P   G   R   S
      L
  1 CAG GTG CAC CTG GTG GAG TCT GGG GGA GGC GTG GTC CAG CCT GGG AGG TCC
    CTG
                                                              CDR 1
                                                      ~~~~~~~~~~~~~~~~~~~~
      R   L   S   C   A   A   S   G   F   T   F   S   S   Y   G   M   H
      W
 55 AGA CTC TCC TGT GCA GCG TCT GGA TTC ACC TTC AGT AGC TAT GGC ATG CAC
    TGG
                                                                  CDR 2
    ~~~~~~~~~~~~~~~~~~~~
      V   R   Q   A   P   G   K   G   L   E   W   V   A   V   I   W   Y
      D
109 GTC CGC CAG GCT CCA GGC AAG GGG CTG GAG TGG GTG GCA GTT ATA TGG TAT
    GAT
                  CDR 2
    ~~~~~~~~~~~~~~~~~~~~~~~~~~~~~~~~~~~~~~~~~~~~~
      G   S   N   K   Y   Y   A   D   S   V   K   G   R   F   T   I   S
      R
163 GGA AGT AAT AAA TAC TAT GCA GAC TCC GTG AAG GGC CGA TTC ACC ATC TCC
    AGA
      D   N   S   K   N   T   L   Y   L   Q   M   N   S   L   R   A   E
      D
217 GAC AAT TCC AAG AAC ACG CTG TAT CTG CAA ATG AAC AGC CTG AGA GCC GAG
    GAC
                                                      CDR 3
    ~~~~~~~~~~~~~~~~~~~~~~~~~~~~~~~~~~~~~~~~~~~
      T   A   V   Y   Y   C   A   R   D   P   H   C   S   S   T   N   C
      Y
271 ACG GCT GTG TAT TAC TGT GCG AGA GAT CCC CAT TGT AGT AGT ACC AAC TGC
    TAC
        CDR 3
    ~~~~~~~~~~~~~~~~
      L   F   D   Y   W   G   Q   G   T   L   V   T   V   S   S
325 CTT TTT GAC TAC TGG GGC CAG GGA ACC CTG GTC ACC GTC TCC TCA
```

FIGURE 6A

Anti-LAG3 17E5 VK

V segment:       L6
    J segment:       JK5

```
        E   I   V   L   T   Q   S   P   A   T   L   S   L   S   P   G   E
    R
  1 GAA ATT GTG TTG ACA CAG TCT CCA GCC ACC CTG TCT TTG TCT CCA GGG GAA
    AGA
                                          CDR 1
                             ~~~~~~~~~~~~~~~~~~~~~~~~~~~~~~~~~~~~~~~~~~~
        A   T   L   S   C   R   A   S   Q   S   V   S   S   Y   L   A   W
    Y
 55 GCC ACC CTC TCC TGC AGG GCC AGT CAG AGT GTT AGC AGC TAC TTA GCC TGG
    TAC

CDR 2
    ~~~~~~~~~~~~~~~~~~~~~
        Q   Q   K   P   G   Q   A   P   R   L   L   I   Y   D   A   S   N
    R
109 CAA CAG AAA CCT GGC CAG GCT CCC AGG CTC CTC ATC TAT GAT GCA TCC AAC
    AGG

CDR 2
    ~~~~~~~
        A   T   G   I   P   A   R   F   S   G   S   G   S   G   T   D   F
    T
163 GCC ACT GGC ATC CCA GCC AGG TTC AGT GGC AGT GGG TCT GGG ACA GAC TTC
    ACT
                                                                      CDR
    3

~~~~~~~~
        L   T   I   S   S   L   E   P   E   D   F   A   V   Y   Y   C   Q
    Q
217 CTC ACC ATC AGC AGC CTA GAG CCT GAA GAT TTT GCA GTT TAT TAC TGT CAG
    CAG

CDR 3
    ~~~~~~~~~~~~~~~~~~~~~~~~~~~~~
        R   S   N   W   P   I   T   F   G   Q   G   T   R   L   E   I   K
271 CGT AGC AAC TGG CCT ATC ACC TTC GGC CAA GGG ACA CGA CTG GAG ATT AAA
```

FIGURE 6B

Anti-LAG3 25F7 VH

```
       CDR1
4-34 germline    Q V Q L Q Q W G A G L L K P S E T L S L T C A
V Y G G S F S G Y Y W S W
25F7 VH          - - - - - - - - - - - - - - - - - - - - - - -
- - - - - - - D - - - N -

CDR2
4-34 germline    I R Q P P G K G L E W I G E I N H S G S T N Y
N P S L K S R V T I S V D
25F7 VH          - - - - - - - - - - - - - - - - - N - N - - S
- - - - - - - - - - L - L -

CDR3
4-34 germline    T S K N Q F S L K L S S V T A A D T A V Y Y C
A R
JH5b germline
N W F D
25F7 VH          - - - - - - - - - - R - - - - - - - - - - - -
- F G Y S D Y E Y - - - -

JH5b germline    P W G Q G T L V T V S S
25F7 VH          - - - - - - - - - - - -       (JH5b)
```

FIGURE 7

Anti-LAG3 25F7 VK

```
        ___CDR1_____
L6 germline     E I V L T Q S P A T L S L S P G E R A T L S C
R A S Q S V S S
25F7 VK         - - - - - - - - - - - - - - - - - - - - - - -
- - - - - I - -

___CDR2_____
L6 germline     Y L A W Y Q Q K P G Q A P R L L I Y D A S N R
A T G I P A R F
25F7 VK         - - - - - - - - - - - - - - - - - - - - - - -
- - - - - - - -

_CDR3____
L6 germline     S G S G S G T D F T L T I S S L E P E D F A V
Y Y C Q Q R S N
25F7 VK         - - - - - - - - - - - - - - - - - - - - - - -
- - - - - - - -

L6 germline     W P
JK2 germline        T F G Q G T K L E I K
25F7 VK         - - L - - - - - - N - - - -    (JK2)
```

FIGURE 8

```
Anti-LAG3 26H10 VH

_CDR1____
3-33 germline      Q V Q L V E S G G G V V Q P G R S L R L S C
A A S G F T F S S Y G M H W
26H10 VH           - - - - - - - - - - - - - - - - - - - - -
- - - - - - - - - - - - - -

_CDR2_____
3-33 germline      V R Q A P G K G L E W V A V I W Y D G S N K
Y Y A D S V K G R F T I S R
26H10 VH           - - - - - - - - - - - - - - - - - - - - -
- - - - - - - - - - - - - -

_CDR3_____
3-33 germline      D N S K N T L Y L Q M N S L R A E D T A V Y
Y C A R
JH6b germline
Y G
26H10 VH           - - - - - - - - - - - - - - - - - - - - -
- - - - E W A V A S W D - -

_____
JH6b germline      M D V W G Q G T T V T V S S
26H10 VH           - - - - - - - - - - - - - -
```

FIGURE 9

Anti-LAG3 26H10 VK

```
              _CDR1_____
A27 germline       E I V L T Q S P G T L S L S P G E R A T L S
C R A S Q S V S S S Y L A W
26H10 VK           - - - - - - - - - - - - - - - - - - - - - -
- - - - - - - - - - - - - -
```

```
                                               _CDR2_____
A27 germline       Y Q Q K P G Q A P R L L I Y G A S S R A T G
I P D R F S G S G S G T D F
26H10 VK           - - - - - - - - - - - - - - - - - - - - - - -
- - - - - - - - - - -
```

```
CDR3_____
A27 germline       T L T I S R L E P E D F A V Y Y C Q Q Y G S
S P
JK3 germline
F T F G P G T K V D I K
26H10 VK           - - - - - - - - - - - - - - - - - - - - - - -
- - - - - - - - - - -
```

FIGURE 10

Anti-LAG3 25E3 VH

```
_CDR1____
3-20 germline  E V Q L V E S G G G V V R P G G S L R L S C A A
S G F T F D D Y G M S W
25E3 VH        - - - - - - - - - - - - - - - - - - - - - - - -
- - - - - - - - - - - - -

_CDR2_____
3-20 germline  V R Q A P G K G L E W V S G I N W N G G S T G Y
A D S V K G R F T I S R
25E3 VH        - - - - - - - - - - - - - - - - - - - - - - Y -
- - - - - - - - - - - G CDR 3_
3-20 germline  D N A K N S L Y L Q M N S L R A E D T A L Y H C
A R
JH4b germline
Y W G Q G T L V
25E3 VH        - - - - - - - - - - - - - - - - - - - - - - Y -
T T G G - - - - - - - -

JH4b germline  T V S S
25E3 VH        - - - - (JH4B)
```

FIGURE 11

Anti-LAG3 25E3 VK

```
              ____CDR_1____
L18  germline A I Q L T Q S P S S L S A S V G D R V T I T C R
A S Q G I S S
25E3 VK1      - - - - - - - - - - - - - - - - - - - - - - - -
- - - - - R -

CDR_1
     _CDR2_____
L18  germline A L A W Y Q Q K P G K A P K L L I Y D A S S L E
S G V P S R F
25E3 VK1      - - - - - - - - - - - - - - - - - - - - - - - -
- - - - - - -

_CDR3____
L18  germline S G S G S G T D F T L T I S S L Q P E D F A T Y
Y C Q Q F N S
25E3 VK1      - - - - - - - - - - - - - - - - - - - - - - - -
- - - - - - -

CDR_3__
L18  germline       Y P
JK2  germline         Y T F G Q G T K L E I K (JK2)
```

FIGURE 12

```
Anti-LAG3 8B7 VH

CDR1
4-34 germline      Q V Q L Q Q W G A G L L K P S E T L S L T C
A V Y G G S F S G Y Y W S W
8B7 VH             - - - - - - - - - - - - - - - - - - - - - - -
- - - - - - - - - - - - - -

CDR2
4-34 germline      I R Q P P G K G L E W I G E I N H S G S T N
Y N P S L K S R V T I S V D
8B7 VH             - - - - - - - - - - - - - - - - - - R - N - -
C - - - - - - - - - - - G -

CDR3
4-34 germline      T S K N Q F S L K L S S V T A A D T A V Y Y
C A R G
JH5b germline
D
8B7 VH             - - - K - - A - - - N - - - - - - - - - - -
- - - - - - - - - - - E -

JH5b germline      P W G Q G T L V T V S S
8B7 VH             S - - P - - - - - - - -
```

FIGURE 13

Anti-LAG3 8B7 VK

```
_CDR1_____
L6 germline           E I V L T Q S P A T L S L S P G E R A T L S
C R A S Q S V S S
8B7 VK                - - - - - - - - - - - - - - - - - - - - - -
- - - - - - - - -

_CDR2_____                  _____
L6 germline           Y L A W Y Q Q K P G Q A P R L L I Y D A S N
R A T G I P A R F
8B7 VK                - - - - - - - - - - - - - - - - - - - N - - -
- - - - - - - - -

_CDR3____
L6 germline           S G S G S G T D F T L T I S S L E P E D F A
V Y Y C Q Q R S N
8B7 VK                - - - - - - - - - - - - - - - - - - - - - -
- - - - - - - - -

_____
L6 germline           W P
JK4 germline              L T F G G G T K V E I K
8B7 VK                - - - - - - - - - - - - - - -
```

FIGURE 14

Anti-LAG3 11F2 VH

```
_CDR1____
1-24 germline      (T H A) Q V Q L V Q S G A E V K K P G A S V
K V S C K V S G Y T L T E L S M H W
11F2.6 VH          - - D - - - - - - - - - - - - - - - - - -
- - - - - - - - - - - - - V - - - -

_CDR2_____
1-24 germline      V R Q A P G K G L E W M G G F D P E D G E
T I Y A Q K F Q G R V T M T E
11F2.6 VH          - - - - - - - - - - - - - - - - - - - - -
- - - - - - - - - - - - - - -

_CDR3_____
1-24 germline      D T S T D T A Y M E L S S L R S E D T A V
Y Y C A T
JH4b germline
D
11F2.6 VH          - - - - - - - - - - - - - - - - - - - - -
- - - - - A F V V V A A S -

JH4b germline      Y W G Q G T L V T V S S
11F2.6 VH          - - - - - - - - - - - - (JH4b)

Please note: THA is from the predicted leader sequence of VH
1-24
```

FIGURE 15

Anti-LAG3 11F2 VK

```
         CDR1
L6 germline            E I V L T Q S P A T L S L S P G E R A T
L S C R A S Q S V S S
11F2.6 VK              - - - - - - - - - - - - - - - - - - - -
- - - - - - - - - - -

CDR2
L6 germline            Y L A W Y Q Q K P G Q A P R L L I Y D A
S N R A T G I P A R F
11F2.6 VK              - - - - - - - - - - - - - - - - - - - -
- - - - - - - - - - -

CDR3
L6 germline            S G S G S G T D F T L T I S S L E P E D
F A V Y Y C Q Q R S N
11F2.6 VK              - - - - - - - - - - - - - - - - - - - -
- - - - - - - - - - -

L6  germline           W P
JK1 germline              W T F G Q G T K V E I K
11F2.6 VK              - - - - - - - - - - - - - -(JK1)
```

FIGURE 16

Anti-LAG3 17E5 VH

```
_CDR1____
3-33 germline      Q V Q L V E S G G G V V Q P G R S L R L S
C A A S G F T F S S Y G M H W
17E5 VH            - - H - - - - - - - - - - - - - - - - -
- - - - - - - - - - - - - -

_CDR2_____
3-33 germline      V R Q A P G K G L E W V A V I W Y D G S N
K Y Y A D S V K G R F T I S R
17E5 VH            - - - - - - - - - - - - - - - - - - - -
- - - - - - - - - - - - - -

_CDR3_____
3-33 germline      D N S K N T L Y L Q M N S L R A E D T A V
Y Y C A R
2-2  germline
C S S T S C Y
17E5 VH            - - - - - - - - - - - - - - - - - - - - -
- - - - - D P H - - - - N - -

_____
2-2  germline          T
JH4b germline        F D Y W G Q G T L V T V S S
17E5 VH              L - - - - - - - - - - - - -
```

FIGURE 17

Anti-LAG3 17E5 VK

```
         _CDR1_____
L6 germline          E I V L T Q S P A T L S L S P G E R A T L S
C R A S Q S V S S
17E5 VK              - - - - - - - - - - - - - - - - - - - - - -
- - - - - - - - -

_CDR2_____
L6 germline          Y L A W Y Q Q K P G Q A P R L L I Y D A S N
R A T G I P A R F
17E5 VK              - - - - - - - - - - - - - - - - - - - - - -
- - - - - - - - -

_CDR3____
L6 germline          S G S G S G T D F T L T I S S L E P E D F A
V Y Y C Q Q R S N
17E5 VK              - - - - - - - - - - - - - - - - - - - - - -
- - - - - - - - -

L6   germline        W P
JK5 germline             I T F G Q G T R L E I K
17E5 VK              - - - - - - - - - - - - - -
```

FIGURE 18

```
                                               1
50
Rhesus LAG-3 (XM_001108923)    (1)
MWEAQFLGLLFLQPLWVAPVKPPQPGAEISVVWAQEGAPAQLPCSPTIPL
          cDNA Clone pa23-5    (1)
MWEAQFLGLLFLQPLWVAPVKPPQPGAEISVVWAQEGAPAQLPCSPTIPL
                                              51
100
Rhesus LAG-3 (XM_001108923)    (51)
QDLSLLRRAGVTWQHQPDSGPPAPAPGHPPAPGHRPAAPYSWGPRPRRYT
          cDNA Clone pa23-5    (51)
QDLSLLRRAGVTWQHQPDSGPPAPAPGHPPAPGHRPAAPYSWGPRPRRYT
         extra loop peptide
                                             101
150
Rhesus LAG-3 (XM_001108923)    (101)
VLSVGPGGLRSGRLPLQPRVQLDERGRQRGDFSLWLRPARRADAGEYRAT
          cDNA Clone pa23-5    (101)
VLSVGPGGLRSGRLPLQPRVQLDERGRQRGDFSLWLRPARRADAGEYRAT
                                             151
200
Rhesus LAG-3 (XM_001108923)    (151)
VHLRDRALSCRLRLRVGQASMTASPPGSLRTSDWVILNCSFSRPDRPASV
          cDNA Clone pa23-5    (151)
VHLRDRALSCRLRLRVGQASMTASPPGSLRTSDWVILNCSFSRPDRPASV
                                             201
250
Rhesus LAG-3 (XM_001108923)    (201)
HWFRSRGQGRVPVQGSPHHHLAESFLFLPHVGPMDSGLWGCILTYRDGFN
          cDNA Clone pa23-5    (201)
HWFRSRGQGRVPVQGSPHHHLAESFLFLPHVGPMDSGLWGCILTYRDGFN
                                             251
300
Rhesus LAG-3 (XM_001108923)    (251)
VSIMYNLTVLGLEPATPLTVYAGAGSRVELPCRLPPAVGTQSFLTAKWAP
          cDNA Clone pa23-5    (251)
VSIMYNLTVLGLEPATPLTVYAGAGSRVELPCRLPPAVGTQSFLTAKWAP
                                             301
350
Rhesus LAG-3 (XM_001108923)    (301)
PGGGPDLLVAGDNGDFTLRLEDVSQAQAGTYICHIRLQGQQLNATVTLAI
          cDNA Clone pa23-5    (301)
PGGGPDLLVAGDNGDFTLRLEDVSQAQAGTYICHIRLQGQQLNATVTLAI
                                             351
400
Rhesus LAG-3 (XM_001108923)    (351)
ITVTPKSFGSPGSLGKLLCEVTPASGQEHFVWSPLNTPSQRSFSGPWLEA
          cDNA Clone pa23-5    (351)
ITVTPKSFGSPGSLGKLLCEVTPASGQEHFVWSPLNTPSQRSFSGPWLEA
                                             401
```

FIGURE 19A

```
                                                  450
Rhesus LAG-3 (XM_001108923)   (401)
QEAQLLSQPWQCQLHQGETLLGAAVYFTELSSPGAQRSGRAPGALRAGHL
           cDNA Clone pa23-5  (401)
QEAQLLSQPWQCQLHQGERLLGAAVYFTELSSPGAQRSGRAPGALRAGHL
                                         451
                                                  500
Rhesus LAG-3 (XM_001108923)   (451)
PLFLILGVLFLLLLVTGAFGFHLWRRQWRPRRFSALEQGIHPPQAQSKIE
           cDNA Clone pa23-5  (451)
PLFLILGVLFLLLLVTGAFGFHLWRRQWRPRRFSALEQGIHPPQAQSKIE
                                       Transmembrane Domain
                                         501
                                                  534
Rhesus LAG-3 (XM_001108923)   (501)
ELEQEPELEPEPELERELGPEPEPGPEPEPEQL-
           cDNA Clone pa23-5  (501)
ELEQEPELEPEPELERELGPEPEPGPEPEPEQL-
```

FIGURE 19B

SEQUENCE LISTING

<160> NUMBER OF SEQ ID NOS: 95

<210> SEQ ID NO 1
<211> LENGTH: 5
<212> TYPE: PRT
<213> ORGANISM: Homo sapiens

<400> SEQUENCE: 1

Asp Tyr Tyr Trp Asn
1               5

<210> SEQ ID NO 2
<211> LENGTH: 5
<212> TYPE: PRT
<213> ORGANISM: Homo sapiens

<400> SEQUENCE: 2

Ser Tyr Gly Met His
1               5

<210> SEQ ID NO 3
<211> LENGTH: 5
<212> TYPE: PRT
<213> ORGANISM: Homo sapiens

<400> SEQUENCE: 3

Asp Tyr Gly Met Ser
1               5

<210> SEQ ID NO 4
<211> LENGTH: 5
<212> TYPE: PRT
<213> ORGANISM: Homo sapiens

<400> SEQUENCE: 4

Gly Tyr Tyr Trp Ser
1               5

<210> SEQ ID NO 5
<211> LENGTH: 5
<212> TYPE: PRT
<213> ORGANISM: Homo sapiens

<400> SEQUENCE: 5

Glu Val Ser Met His
1               5

<210> SEQ ID NO 6

```
<211> LENGTH: 5
<212> TYPE: PRT
<213> ORGANISM: Homo sapiens

<400> SEQUENCE: 6

Ser Tyr Gly Met His
1               5

<210> SEQ ID NO 7
<211> LENGTH: 16
<212> TYPE: PRT
<213> ORGANISM: Homo sapiens

<400> SEQUENCE: 7

Glu Ile Asn His Asn Gly Asn Thr Asn Ser Asn Pro Ser Leu Lys Ser
1               5                   10                  15

<210> SEQ ID NO 8
<211> LENGTH: 17
<212> TYPE: PRT
<213> ORGANISM: Homo sapiens

<400> SEQUENCE: 8

Val Ile Trp Tyr Asp Gly Ser Asn Lys Tyr Tyr Ala Asp Ser Val Lys
1               5                   10                  15

Gly

<210> SEQ ID NO 9
<211> LENGTH: 17
<212> TYPE: PRT
<213> ORGANISM: Homo sapiens

<400> SEQUENCE: 9

Gly Ile Asn Trp Asn Gly Gly Ser Thr Tyr Tyr Ala Asp Ser Val Lys
1               5                   10                  15

Gly

<210> SEQ ID NO 10
<211> LENGTH: 16
<212> TYPE: PRT
<213> ORGANISM: Homo sapiens

<400> SEQUENCE: 10

Glu Ile Asn His Arg Gly Asn Thr Asn Cys Asn Pro Ser Leu Lys Ser
1               5                   10                  15

<210> SEQ ID NO 11
<211> LENGTH: 17
<212> TYPE: PRT
<213> ORGANISM: Homo sapiens

<400> SEQUENCE: 11

Gly Phe Asp Pro Glu Asp Gly Glu Thr Ile Tyr Ala Gln Lys Phe Gln
1               5                   10                  15

Gly

<210> SEQ ID NO 12
<211> LENGTH: 17
<212> TYPE: PRT
<213> ORGANISM: Homo sapiens

<400> SEQUENCE: 12

Val Ile Trp Tyr Asp Gly Ser Asn Lys Tyr Tyr Ala Asp Ser Val Lys
```

```
1               5                   10                  15
Gly

<210> SEQ ID NO 13
<211> LENGTH: 12
<212> TYPE: PRT
<213> ORGANISM: Homo sapiens

<400> SEQUENCE: 13

Gly Tyr Ser Asp Tyr Glu Tyr Asn Trp Phe Asp Pro
1               5                   10

<210> SEQ ID NO 14
<211> LENGTH: 13
<212> TYPE: PRT
<213> ORGANISM: Homo sapiens

<400> SEQUENCE: 14

Glu Trp Ala Val Ala Ser Trp Asp Tyr Gly Met Asp Val
1               5                   10

<210> SEQ ID NO 15
<211> LENGTH: 5
<212> TYPE: PRT
<213> ORGANISM: Homo sapiens

<400> SEQUENCE: 15

Pro Val Gly Val Val
1               5

<210> SEQ ID NO 16
<211> LENGTH: 12
<212> TYPE: PRT
<213> ORGANISM: Homo sapiens

<400> SEQUENCE: 16

Gly Tyr Asp Ile Leu Thr Gly Tyr Tyr Glu Asp Ser
1               5                   10

<210> SEQ ID NO 17
<211> LENGTH: 11
<212> TYPE: PRT
<213> ORGANISM: Homo sapiens

<400> SEQUENCE: 17

Ala Phe Val Val Val Val Ala Ala Ser Asp Tyr
1               5                   10

<210> SEQ ID NO 18
<211> LENGTH: 14
<212> TYPE: PRT
<213> ORGANISM: Homo sapiens

<400> SEQUENCE: 18

Asp Pro His Cys Ser Ser Thr Asn Cys Tyr Leu Phe Asp Tyr
1               5                   10

<210> SEQ ID NO 19
<211> LENGTH: 11
<212> TYPE: PRT
<213> ORGANISM: Homo sapiens

<400> SEQUENCE: 19

Arg Ala Ser Gln Ser Ile Ser Ser Tyr Leu Ala
```

-continued

```
1               5                   10
```

<210> SEQ ID NO 20
<211> LENGTH: 12
<212> TYPE: PRT
<213> ORGANISM: Homo sapiens

<400> SEQUENCE: 20

```
Arg Ala Ser Gln Ser Val Ser Ser Ser Tyr Leu Ala
1               5                   10
```

<210> SEQ ID NO 21
<211> LENGTH: 11
<212> TYPE: PRT
<213> ORGANISM: Homo sapiens

<400> SEQUENCE: 21

```
Arg Ala Ser Gln Gly Ile Arg Ser Ala Leu Ala
1               5                   10
```

<210> SEQ ID NO 22
<211> LENGTH: 11
<212> TYPE: PRT
<213> ORGANISM: Homo sapiens

<400> SEQUENCE: 22

```
Arg Ala Ser Gln Ser Val Ser Ser Tyr Leu Ala
1               5                   10
```

<210> SEQ ID NO 23
<211> LENGTH: 11
<212> TYPE: PRT
<213> ORGANISM: Homo sapiens

<400> SEQUENCE: 23

```
Arg Ala Ser Gln Ser Val Ser Ser Tyr Leu Ala
1               5                   10
```

<210> SEQ ID NO 24
<211> LENGTH: 11
<212> TYPE: PRT
<213> ORGANISM: Homo sapiens

<400> SEQUENCE: 24

```
Arg Ala Ser Gln Ser Val Ser Ser Tyr Leu Ala
1               5                   10
```

<210> SEQ ID NO 25
<211> LENGTH: 7
<212> TYPE: PRT
<213> ORGANISM: Homo sapiens

<400> SEQUENCE: 25

```
Asp Ala Ser Asn Arg Ala Thr
1               5
```

<210> SEQ ID NO 26
<211> LENGTH: 7
<212> TYPE: PRT
<213> ORGANISM: Homo sapiens

<400> SEQUENCE: 26

```
Gly Ala Ser Ser Arg Ala Thr
1               5
```

<210> SEQ ID NO 27
<211> LENGTH: 7
<212> TYPE: PRT
<213> ORGANISM: Homo sapiens

<400> SEQUENCE: 27

Asp Ala Ser Ser Leu Glu Ser
1               5

<210> SEQ ID NO 28
<211> LENGTH: 7
<212> TYPE: PRT
<213> ORGANISM: Homo sapiens

<400> SEQUENCE: 28

Asn Ala Ser Asn Arg Ala Thr
1               5

<210> SEQ ID NO 29
<211> LENGTH: 7
<212> TYPE: PRT
<213> ORGANISM: Homo sapiens

<400> SEQUENCE: 29

Asp Ala Ser Asn Arg Ala Thr
1               5

<210> SEQ ID NO 30
<211> LENGTH: 7
<212> TYPE: PRT
<213> ORGANISM: Homo sapiens

<400> SEQUENCE: 30

Asp Ala Ser Asn Arg Ala Thr
1               5

<210> SEQ ID NO 31
<211> LENGTH: 9
<212> TYPE: PRT
<213> ORGANISM: Homo sapiens

<400> SEQUENCE: 31

Gln Gln Arg Ser Asn Trp Pro Leu Thr
1               5

<210> SEQ ID NO 32
<211> LENGTH: 9
<212> TYPE: PRT
<213> ORGANISM: Homo sapiens

<400> SEQUENCE: 32

Gln Gln Tyr Gly Ser Ser Pro Phe Thr
1               5

<210> SEQ ID NO 33
<211> LENGTH: 9
<212> TYPE: PRT
<213> ORGANISM: Homo sapiens

<400> SEQUENCE: 33

Gln Gln Phe Asn Ser Tyr Pro Tyr Thr
1               5

<210> SEQ ID NO 34

```
<211> LENGTH: 9
<212> TYPE: PRT
<213> ORGANISM: Homo sapiens

<400> SEQUENCE: 34

Gln Gln Arg Ser Asn Trp Pro Leu Thr
1               5

<210> SEQ ID NO 35
<211> LENGTH: 9
<212> TYPE: PRT
<213> ORGANISM: Homo sapiens

<400> SEQUENCE: 35

Gln Gln Arg Ser Asn Trp Pro Trp Thr
1               5

<210> SEQ ID NO 36
<211> LENGTH: 9
<212> TYPE: PRT
<213> ORGANISM: Homo sapiens

<400> SEQUENCE: 36

Gln Gln Arg Ser Asn Trp Pro Ile Thr
1               5

<210> SEQ ID NO 37
<211> LENGTH: 120
<212> TYPE: PRT
<213> ORGANISM: Homo sapiens

<400> SEQUENCE: 37

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Asn Gly Asn Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser
        115                 120

<210> SEQ ID NO 38
<211> LENGTH: 122
<212> TYPE: PRT
<213> ORGANISM: Homo sapiens

<400> SEQUENCE: 38

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45
```

Ala Val Ile Trp Tyr Asp Gly Ser Asn Lys Tyr Tyr Ala Asp Ser Val
                50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg Glu Trp Ala Val Ala Ser Trp Asp Tyr Gly Met Asp Val Trp
                100                 105                 110

Gly Gln Gly Thr Thr Val Thr Val Ser Ser
                115                 120

<210> SEQ ID NO 39
<211> LENGTH: 112
<212> TYPE: PRT
<213> ORGANISM: Homo sapiens

<400> SEQUENCE: 39

Glu Val Gln Leu Val Glu Ser Gly Gly Gly Val Val Arg Pro Gly Gly
  1               5                  10                  15

Ser Leu Arg Leu Ser Cys Ala Ala Ser Gly Phe Thr Phe Asp Asp Tyr
                 20                  25                  30

Gly Met Ser Trp Val Arg Gln Ala Pro Gly Lys Gly Leu Glu Trp Val
             35                  40                  45

Ser Gly Ile Asn Trp Asn Gly Ser Thr Tyr Tyr Ala Asp Ser Val
         50                  55                  60

Lys Gly Arg Phe Thr Ile Ser Gly Asp Asn Ala Lys Asn Ser Leu Tyr
 65                  70                  75                  80

Leu Gln Met Asn Ser Leu Arg Ala Glu Asp Thr Ala Leu Tyr Tyr Cys
                    85                  90                  95

Thr Thr Gly Gly Tyr Trp Gly Gln Gly Thr Leu Val Thr Val Ser Ser
                100                 105                 110

<210> SEQ ID NO 40
<211> LENGTH: 120
<212> TYPE: PRT
<213> ORGANISM: Homo sapiens

<400> SEQUENCE: 40

Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Gly Tyr
                 20                  25                  30

Tyr Trp Ser Trp Ile Arg Gln Pro Pro Gly Lys Gly Leu Glu Trp Ile
             35                  40                  45

Gly Glu Ile Asn His Arg Gly Asn Thr Asn Cys Asn Pro Ser Leu Lys
         50                  55                  60

Ser Arg Val Thr Ile Ser Gly Asp Thr Ser Lys Lys Gln Phe Ala Leu
 65                  70                  75                  80

Lys Leu Asn Ser Val Thr Ala Ala Asp Thr Ala Val Tyr Tyr Cys Ala
                    85                  90                  95

Arg Gly Tyr Asp Ile Leu Thr Gly Tyr Tyr Glu Asp Ser Trp Gly Pro
                100                 105                 110

Gly Thr Leu Val Thr Val Ser Ser
                115                 120

<210> SEQ ID NO 41

```
<211> LENGTH: 123
<212> TYPE: PRT
<213> ORGANISM: Homo sapiens

<400> SEQUENCE: 41

Thr His Asp Gln Val Gln Leu Val Gln Ser Gly Ala Glu Val Lys Lys
1               5                   10                  15

Pro Gly Ala Ser Val Lys Val Ser Cys Lys Val Ser Gly Tyr Thr Leu
            20                  25                  30

Thr Glu Val Ser Met His Trp Val Arg Gln Ala Pro Gly Lys Gly Leu
        35                  40                  45

Glu Trp Met Gly Gly Phe Asp Pro Glu Asp Gly Glu Thr Ile Tyr Ala
    50                  55                  60

Gln Lys Phe Gln Gly Arg Val Thr Met Thr Glu Asp Thr Ser Thr Asp
65                  70                  75                  80

Thr Ala Tyr Met Glu Leu Ser Ser Leu Arg Ser Glu Asp Thr Ala Val
                85                  90                  95

Tyr Tyr Cys Ala Thr Ala Phe Val Val Val Ala Ala Ser Asp Tyr
            100                 105                 110

Trp Gly Gln Gly Thr Leu Val Thr Val Ser Ser
            115                 120

<210> SEQ ID NO 42
<211> LENGTH: 123
<212> TYPE: PRT
<213> ORGANISM: Homo sapiens

<400> SEQUENCE: 42

Gln Val His Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro His Cys Ser Ser Thr Asn Cys Tyr Leu Phe Asp Tyr
            100                 105                 110

Trp Gly Gln Gly Thr Leu Val Thr Val Ser Ser
            115                 120

<210> SEQ ID NO 43
<211> LENGTH: 107
<212> TYPE: PRT
<213> ORGANISM: Homo sapiens

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45
```

Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gln Gly Thr Asn Leu Glu Ile Lys
                100                 105

<210> SEQ ID NO 44
<211> LENGTH: 108
<212> TYPE: PRT
<213> ORGANISM: Homo sapiens

<400> SEQUENCE: 44

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Phe Thr Phe Gly Pro Gly Thr Lys Val Asp Ile Lys
                100                 105

<210> SEQ ID NO 45
<211> LENGTH: 107
<212> TYPE: PRT
<213> ORGANISM: Homo sapiens

<400> SEQUENCE: 45

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Arg Ser Ala
                 20                  25                  30

Leu Ala Trp Tyr Gln Gln Lys Pro Gly Lys Ala Pro Lys Leu Leu Ile
             35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Tyr
                 85                  90                  95

Thr Phe Gly Gln Gly Thr Lys Leu Glu Ile Lys
                100                 105

<210> SEQ ID NO 46
<211> LENGTH: 107
<212> TYPE: PRT
<213> ORGANISM: Homo sapiens

<400> SEQUENCE: 46

Glu Ile Val Leu Thr Gln Ser Pro Ala Thr Leu Ser Leu Ser Pro Gly

```
                1               5                  10                 15
Glu Arg Ala Thr Leu Ser Cys Arg Ala Ser Gln Ser Val Ser Ser Tyr
            20                  25                 30

Leu Ala Trp Tyr Gln Gln Lys Pro Gly Gln Ala Pro Arg Leu Leu Ile
            35                  40                 45

Tyr Asn Ala Ser Asn Arg Ala Thr Gly Ile Pro Ala Arg Phe Ser Gly
        50                  55                 60

Ser Gly Ser Gly Thr Asp Phe Thr Leu Thr Ile Ser Ser Leu Glu Pro
65                  70                  75                 80

Glu Asp Phe Ala Val Tyr Tyr Cys Gln Gln Arg Ser Asn Trp Pro Leu
                85                  90                 95

Thr Phe Gly Gly Gly Thr Lys Val Glu Ile Lys
            100                 105
```

<210> SEQ ID NO 47
<211> LENGTH: 107
<212> TYPE: PRT
<213> ORGANISM: Homo sapiens

<400> SEQUENCE: 47

```
Glu Ile Val Leu Thr Gln Ser Pro Ala Thr Leu Ser Leu Ser Pro Gly
1               5                   10                 15

Glu Arg Ala Thr Leu Ser Cys Arg Ala Ser Gln Ser Val Ser Ser Tyr
            20                  25                 30

Leu Ala Trp Tyr Gln Gln Lys Pro Gly Gln Ala Pro Arg Leu Leu Ile
            35                  40                 45

Tyr Asp Ala Ser Asn Arg Ala Thr Gly Ile Pro Ala Arg Phe Ser Gly
        50                  55                 60

Ser Gly Ser Gly Thr Asp Phe Thr Leu Thr Ile Ser Ser Leu Glu Pro
65                  70                  75                 80

Glu Asp Phe Ala Val Tyr Tyr Cys Gln Gln Arg Ser Asn Trp Pro Trp
                85                  90                 95

Thr Phe Gly Gln Gly Thr Lys Val Glu Ile Lys
            100                 105
```

<210> SEQ ID NO 48
<211> LENGTH: 107
<212> TYPE: PRT
<213> ORGANISM: Homo sapiens

<400> SEQUENCE: 48

```
Glu Ile Val Leu Thr Gln Ser Pro Ala Thr Leu Ser Leu Ser Pro Gly
1               5                   10                 15

Glu Arg Ala Thr Leu Ser Cys Arg Ala Ser Gln Ser Val Ser Ser Tyr
            20                  25                 30

Leu Ala Trp Tyr Gln Gln Lys Pro Gly Gln Ala Pro Arg Leu Leu Ile
            35                  40                 45

Tyr Asp Ala Ser Asn Arg Ala Thr Gly Ile Pro Ala Arg Phe Ser Gly
        50                  55                 60

Ser Gly Ser Gly Thr Asp Phe Thr Leu Thr Ile Ser Ser Leu Glu Pro
65                  70                  75                 80

Glu Asp Phe Ala Val Tyr Tyr Cys Gln Gln Arg Ser Asn Trp Pro Ile
                85                  90                 95

Thr Phe Gly Gln Gly Thr Arg Leu Glu Ile Lys
            100                 105
```

```
<210> SEQ ID NO 49
<211> LENGTH: 360
<212> TYPE: DNA
<213> ORGANISM: Homo sapiens

<400> SEQUENCE: 49
caggtgcagc tacagcagtg gggcgcagga ctgttgaagc cttcggagac cctgtccctc      60
acctgcgctg tctatggtgg gtccttcagt gattactact ggaactggat ccgccagccc     120
ccagggaagg ggctggagtg gattggggaa atcaatcata tggaaacac caactccaac      180 ccgtccctca agagtcgagt caccctatca ctagacacgt ccaagaacca gttctccctg     240
aagctgaggt ctgtgaccgc cgcggacacg gctgtgtatt actgtgcgtt tggatatagt     300
gactacgagt acaactggtt cgaccctggg gccagggaa ccctggtcac cgtctcctca      360

<210> SEQ ID NO 50
<211> LENGTH: 366
<212> TYPE: DNA
<213> ORGANISM: Homo sapiens

<400> SEQUENCE: 50
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg gtggcagtt atatggtatg atggaagtaa taaatactat      180
gcagactccg tgaagggccg attcaccatc tccagagaca attccaagaa cacgctgtat     240
ctgcaaatga acagcctgag agccgaggac acggctgtgt attactgtgc gagagaatgg     300
gcagtggcct cctgggacta cggtatggac gtctggggcc aagggaccac ggtcaccgtc     360
tcctca                                                                 366

<210> SEQ ID NO 51
<211> LENGTH: 336
<212> TYPE: DNA
<213> ORGANISM: Homo sapiens

<400> SEQUENCE: 51
gaggtgcagt tggtggagtc tgggggaggt gtggtacggc ctggggggtc cctgagactc      60
tcctgtgcag cctctggatt cacctttgat gattatggca tgagctgggt ccgccaagct     120
ccagggaagg ggctggagtg gtctctggt attaattgga tggtggtag cacatatat      180 gcagactctg tgaagggccg attcaccatc tccggagaca acgccaagaa ctccctgtat     240
ctgcaaatga acagtctgag agccgaggac acggccttgt attactgtac cactggggc      300 tactggggcc agggaaccct ggtcaccgtc tcctca                               336

<210> SEQ ID NO 52
<211> LENGTH: 360
<212> TYPE: DNA
<213> ORGANISM: Homo sapiens

<400> SEQUENCE: 52
caggtgcagc tacagcagtg gggcgcagga ctgttgaagc catcggaaac cctgtccctc      60
acctgcgctg tctatggtgg gtccttcagt ggttactact ggagctggat ccgccagccc     120
ccagggaagg ggctggagtg gattggggaa atcaatcatc gtggaaacac caactgcaac     180
ccgtccctca agagtcgagt caccatatca ggagatacgt ccaagaaaca gttcgccctg     240
aagctgaact ctgtgaccgc cgcggacacg gctgtctatt actgtgcgag aggatacgat     300
```

```
attttgactg gttattatga ggactcctgg ggcccgggaa ccctggtcac cgtctcctca      360
```

<210> SEQ ID NO 53
<211> LENGTH: 369
<212> TYPE: DNA
<213> ORGANISM: Homo sapiens

<400> SEQUENCE: 53

```
acccacgacc aggtccagct ggtacagtct ggggctgagg tgaagaagcc tggggcctca      60
gtgaaggtct cctgcaaggt ttccggatac accctcactg aagtatccat gcactgggtg     120
cgacaggctc ctggaaaagg gcttgagtgg atgggaggtt ttgatcctga agatggtgaa     180
acaatctacg cacagaagtt ccagggcaga gtcaccatga ccgaggacac atctacagac     240
acagcctaca tggagctgag cagcctgaga tctgaggaca cggccgtgta ttactgtgca     300
acagcctttg tagtggtggt agctgcttct gactactggg gccagggaac cctggtcacc     360
gtctcctca                                                             369
```

<210> SEQ ID NO 54
<211> LENGTH: 369
<212> TYPE: DNA
<213> ORGANISM: Homo sapiens

<400> SEQUENCE: 54

```
caggtgcacc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagatccc     300
cattgtagta gtaccaactg ctaccttttt gactactggg gccagggaac cctggtcacc     360
gtctcctca                                                             369
```

<210> SEQ ID NO 55
<211> LENGTH: 321
<212> TYPE: DNA
<213> ORGANISM: Homo sapiens

<400> SEQUENCE: 55

```
gaaattgtgt tgacacagtc tccagccacc ctgtctttgt ctccagggga aagagccacc      60
ctctcctgca gggccagtca gagtattagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctctcac ttttggccag     300
gggaccaacc tggagatcaa a                                               321
```

<210> SEQ ID NO 56
<211> LENGTH: 324
<212> TYPE: DNA
<213> ORGANISM: Homo sapiens

<400> SEQUENCE: 56

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
```

```
gacaggttca gtggcagtgg gtctgggaca gacttcactc tcaccatcag cagactggag      240
cctgaagatt ttgcagtgta ttactgtcag cagtatggta gctcaccatt cactttcggc      300
cctgggacca aagtggatat caaa                                             324
```

<210> SEQ ID NO 57
<211> LENGTH: 321
<212> TYPE: DNA
<213> ORGANISM: Homo sapiens

<400> SEQUENCE: 57

```
gccatccagt tgacccagtc tccatcctcc ctgtctgcat ctgtaggaga cagagtcacc       60
atcacttgcc gggcaagtca gggcattagg agtgctttag cctggtatca gcagaaacca      120
gggaaagctc ctaagctcct gatctatgat gcctccagtt tggaaagtgg ggtcccatca      180
aggttcagcg gcagtggatc tgggacagat ttcactctca ccatcagcag cctgcagcct      240
gaagattttg caacttatta ctgtcaacag tttaatagtt acccgtacac ttttggccag      300
gggaccaagc tggagatcaa a                                                321
```

<210> SEQ ID NO 58
<211> LENGTH: 321
<212> TYPE: DNA
<213> ORGANISM: Homo sapiens

<400> SEQUENCE: 58

```
gaaattgtgt tgacacagtc tccagccacc ctgtctttgt ctccagggga aagagccacc       60
ctctcctgca gggccagtca gagtgttagc agctacttag cctggtacca acagaaacct      120
ggccaggctc ccaggctcct catctataat gcatccaaca gggccactgg catcccagcc      180
aggttcagtg gcagtgggtc tgggacagac ttcactctca ccatcagcag cctagagcct      240
gaagattttg cagtttatta ctgtcagcag cgtagcaact ggccgctcac tttcggcgga      300
gggaccaagg tggagatcaa a                                                321
```

<210> SEQ ID NO 59
<211> LENGTH: 321
<212> TYPE: DNA
<213> ORGANISM: Homo sapiens

<400> SEQUENCE: 59

```
gaaattgtgt tgacacagtc tccagccacc ctgtctttgt ctccagggga aagagccacc       60
ctctcctgca gggccagtca gagtgttagc agctacttag cctggtacca acagaaacct      120
ggccaggctc ccaggctcct catctatgat gcatccaaca gggccactgg catcccagcc      180
aggttcagtg gcagtgggtc tgggacagac ttcactctca ccatcagcag cctagagcct      240
gaagattttg cagtttatta ctgtcagcag cgtagcaact ggccgtggac gttcggccaa      300
gggaccaagg tggaaatcaa a                                                321
```

<210> SEQ ID NO 60
<211> LENGTH: 321
<212> TYPE: DNA
<213> ORGANISM: Homo sapiens

<400> SEQUENCE: 60

```
gaaattgtgt tgacacagtc tccagccacc ctgtctttgt ctccagggga aagagccacc       60
ctctcctgca gggccagtca gagtgttagc agctacttag cctggtacca acagaaacct      120
```

```
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctatcac cttcggccaa    300
gggacacgac tggagattaa a                                              321
```

<210> SEQ ID NO 61
<211> LENGTH: 98
<212> TYPE: PRT
<213> ORGANISM: Homo sapiens
<220> FEATURE:
<221> NAME/KEY: MISC_FEATURE
<222> LOCATION: (98)..(98)
<223> OTHER INFORMATION: Residue 98 is presented only in a subset of
      figures.

<400> SEQUENCE: 61

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly

<210> SEQ ID NO 62
<211> LENGTH: 16
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: Residues 1-3 are presented only in a subset of
      figures.

<400> SEQUENCE: 62

Asn Trp Phe Asp Pro Trp Gly Gln Gly Thr Leu Val Thr Val Ser Ser
1               5                   10                  15

<210> SEQ ID NO 63
<211> LENGTH: 95
<212> TYPE: PRT
<213> ORGANISM: Homo sapiens

<400> SEQUENCE: 63

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 64
<211> LENGTH: 12
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Residue 1 is presented only in a subset of
      figures.

<400> SEQUENCE: 64

Tyr Thr Phe Gly Gln Gly Thr Lys Leu Glu Ile Lys
1               5                   10

<210> SEQ ID NO 65
<211> LENGTH: 98
<212> TYPE: PRT
<213> ORGANISM: Homo sapiens

<400> SEQUENCE: 65

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 66
<211> LENGTH: 16
<212> TYPE: PRT
<213> ORGANISM: Homo sapiens

<400> SEQUENCE: 66

Tyr Gly Met Asp Val Trp Gly Gln Gly Thr Thr Val Thr Val Ser Ser
1               5                   10                  15

<210> SEQ ID NO 67
<211> LENGTH: 96
<212> TYPE: PRT
<213> ORGANISM: Homo sapiens

<400> SEQUENCE: 67

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 68
<211> LENGTH: 12
<212> TYPE: PRT
<213> ORGANISM: Homo sapiens

<400> SEQUENCE: 68

Phe Thr Phe Gly Pro Gly Thr Lys Val Asp Ile Lys
1               5                   10

<210> SEQ ID NO 69
<211> LENGTH: 98
<212> TYPE: PRT
<213> ORGANISM: Homo sapiens

<400> SEQUENCE: 69

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg

<210> SEQ ID NO 70
<211> LENGTH: 14
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: Residues 1-2 are only presented in a subset of
      figures.

<400> SEQUENCE: 70

Phe Asp Tyr Trp Gly Gln Gly Thr Leu Val Thr Val Ser Ser
1               5                   10

<210> SEQ ID NO 71
<211> LENGTH: 95
<212> TYPE: PRT
<213> ORGANISM: Homo sapiens

<400> SEQUENCE: 71

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro
                 85                  90                  95
```

<210> SEQ ID NO 72
<211> LENGTH: 12
<212> TYPE: PRT
<213> ORGANISM: Homo sapiens

<400> SEQUENCE: 72

```
Leu Thr Phe Gly Gly Gly Thr Lys Val Glu Ile Lys
 1               5                  10
```

<210> SEQ ID NO 73
<211> LENGTH: 101
<212> TYPE: PRT
<213> ORGANISM: Homo sapiens

<400> SEQUENCE: 73

```
Thr His Ala Gln Val Gln Leu Val Gln Ser Gly Ala Glu Val Lys Lys
 1               5                  10                  15

Pro Gly Ala Ser Val Lys Val Ser Cys Lys Val Ser Gly Tyr Thr Leu
                20                  25                  30

Thr Glu Leu Ser Met His Trp Val Arg Gln Ala Pro Gly Lys Gly Leu
             35                  40                  45

Glu Trp Met Gly Gly Phe Asp Pro Glu Asp Gly Glu Thr Ile Tyr Ala
         50                  55                  60

Gln Lys Phe Gln Gly Arg Val Thr Met Thr Glu Asp Thr Ser Thr Asp
 65                  70                  75                  80

Thr Ala Tyr Met Glu Leu Ser Ser Leu Arg Ser Glu Asp Thr Ala Val
                 85                  90                  95

Tyr Tyr Cys Ala Thr
             100
```

<210> SEQ ID NO 74
<211> LENGTH: 12
<212> TYPE: PRT
<213> ORGANISM: Homo sapiens

<400> SEQUENCE: 74

```
Trp Thr Phe Gly Gln Gly Thr Lys Val Glu Ile Lys
 1               5                  10
```

<210> SEQ ID NO 75
<211> LENGTH: 12
<212> TYPE: PRT
<213> ORGANISM: Homo sapiens

<400> SEQUENCE: 75

```
Ile Thr Phe Gly Gln Gly Thr Arg Leu Glu Ile Lys
 1               5                  10
```

<210> SEQ ID NO 76
<211> LENGTH: 8
<212> TYPE: PRT
<213> ORGANISM: Homo sapiens

<400> SEQUENCE: 76

```
Pro Gly His Pro Leu Ala Pro Gly
```

```
<210> SEQ ID NO 77
<211> LENGTH: 8
<212> TYPE: PRT
<213> ORGANISM: Homo sapiens

<400> SEQUENCE: 77

His Pro Ala Ala Pro Ser Ser Trp
1               5

<210> SEQ ID NO 78
<211> LENGTH: 8
<212> TYPE: PRT
<213> ORGANISM: Homo sapiens

<400> SEQUENCE: 78

Pro Ala Ala Pro Ser Ser Trp Gly
1               5

<210> SEQ ID NO 79
<211> LENGTH: 30
<212> TYPE: PRT
<213> ORGANISM: Homo sapiens

<400> SEQUENCE: 79

Gly Pro Pro Ala Ala Ala Pro Gly His Pro Leu Ala Pro Gly Pro His
1               5                   10                  15

Pro Ala Ala Pro Ser Ser Trp Gly Pro Arg Pro Arg Arg Tyr
            20                  25                  30

<210> SEQ ID NO 80
<211> LENGTH: 12
<212> TYPE: PRT
<213> ORGANISM: Homo sapiens

<400> SEQUENCE: 80

Gly Pro Pro Ala Ala Ala Pro Gly His Pro Leu Ala
1               5                   10

<210> SEQ ID NO 81
<211> LENGTH: 12
<212> TYPE: PRT
<213> ORGANISM: Homo sapiens

<400> SEQUENCE: 81

Pro Ala Ala Ala Pro Gly His Pro Leu Ala Pro Gly
1               5                   10

<210> SEQ ID NO 82
<211> LENGTH: 12
<212> TYPE: PRT
<213> ORGANISM: Homo sapiens

<400> SEQUENCE: 82

Ala Ala Pro Gly His Pro Leu Ala Pro Gly Pro His
1               5                   10

<210> SEQ ID NO 83
<211> LENGTH: 12
<212> TYPE: PRT
<213> ORGANISM: Homo sapiens

<400> SEQUENCE: 83
```

-continued

Pro Gly His Pro Leu Ala Pro Gly Pro His Pro Ala
1               5                   10

<210> SEQ ID NO 84
<211> LENGTH: 12
<212> TYPE: PRT
<213> ORGANISM: Homo sapiens

<400> SEQUENCE: 84

His Pro Leu Ala Pro Gly Pro His Pro Ala Ala Pro
1               5                   10

<210> SEQ ID NO 85
<211> LENGTH: 12
<212> TYPE: PRT
<213> ORGANISM: Homo sapiens

<400> SEQUENCE: 85

Leu Ala Pro Gly Pro His Pro Ala Ala Pro Ser Ser
1               5                   10

<210> SEQ ID NO 86
<211> LENGTH: 12
<212> TYPE: PRT
<213> ORGANISM: Homo sapiens

<400> SEQUENCE: 86

Pro Gly Pro His Pro Ala Ala Pro Ser Ser Trp Gly
1               5                   10

<210> SEQ ID NO 87
<211> LENGTH: 12
<212> TYPE: PRT
<213> ORGANISM: Homo sapiens

<400> SEQUENCE: 87

Pro His Pro Ala Ala Pro Ser Ser Trp Gly Pro Arg
1               5                   10

<210> SEQ ID NO 88
<211> LENGTH: 12
<212> TYPE: PRT
<213> ORGANISM: Homo sapiens

<400> SEQUENCE: 88

Pro Ala Ala Pro Ser Ser Trp Gly Pro Arg Pro Arg
1               5                   10

<210> SEQ ID NO 89
<211> LENGTH: 12
<212> TYPE: PRT
<213> ORGANISM: Homo sapiens

<400> SEQUENCE: 89

Ala Pro Ser Ser Trp Gly Pro Arg Pro Arg Arg Tyr
1               5                   10

<210> SEQ ID NO 90
<211> LENGTH: 30
<212> TYPE: PRT
<213> ORGANISM: Macaca sp.

<400> SEQUENCE: 90

Gly Pro Pro Ala Pro Ala Pro Gly His Pro Pro Ala Pro Gly His Arg
1               5                   10                  15

```
Pro Ala Ala Pro Tyr Ser Trp Gly Pro Arg Pro Arg Arg Tyr
            20                  25                  30

<210> SEQ ID NO 91
<211> LENGTH: 21
<212> TYPE: DNA
<213> ORGANISM: Artificial
<220> FEATURE:
<223> OTHER INFORMATION: 5Mcyn1408 primer

<400> SEQUENCE: 91
atgtgggagg ctcagttcct g                                              21

<210> SEQ ID NO 92
<211> LENGTH: 19
<212> TYPE: DNA
<213> ORGANISM: Artificial
<220> FEATURE:
<223> OTHER INFORMATION: 3Mcyn1408a primer

<400> SEQUENCE: 92
gtcagagctg ctccggctc                                                 19

<210> SEQ ID NO 93
<211> LENGTH: 532
<212> TYPE: PRT
<213> ORGANISM: Macaca mulatta

<400> SEQUENCE: 93

Met Trp Glu Ala Gln Phe Leu Gly Leu Leu Phe Leu Gln Pro Leu Trp
1               5                   10                  15

Val Ala Pro Val Lys Pro Pro Gln Pro Gly Ala Glu Ile Ser Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Pro Ala Pro Gly His Pro Pro
65                  70                  75                  80

Ala Pro Gly His Arg Pro Ala Ala Pro Tyr Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Thr Val His Leu Arg Asp Arg Ala Leu Ser Cys
145                 150                 155                 160

Arg Leu Arg Leu Arg Val Gly Gln Ala Ser Met Thr Ala Ser Pro Pro
                165                 170                 175

Gly Ser Leu Arg Thr Ser Asp Trp Val Ile Leu Asn Cys Ser Phe Ser
            180                 185                 190

Arg Pro Asp Arg Pro Ala Ser Val His Trp Phe Arg Ser Arg Gly Gln
        195                 200                 205

Gly Arg Val Pro Val Gln Gly Ser Pro His His Leu Ala Glu Ser
    210                 215                 220

Phe Leu Phe Leu Pro His Val Gly Pro Met Asp Ser Gly Leu Trp Gly
```

```
                225                 230                 235                 240
        Cys Ile Leu Thr Tyr Arg Asp Gly Phe Asn Val Ser Ile Met Tyr Asn
                        245                 250                 255

Leu Thr Val Leu Gly Leu Glu Pro Ala Thr Pro Leu Val Tyr Ala Gly
                        260                 265                 270

Ala Gly Ser Arg Val Glu Leu Pro Cys Arg Leu Pro Pro Ala Val Gly
                        275                 280                 285

Thr Gln Ser Phe Leu Thr Ala Lys Trp Ala Pro Pro Gly Gly Gly Pro
                        290                 295                 300

Asp Leu Leu Val Ala Gly Asp Asn Gly Asp Phe Thr Leu Arg Leu Glu
        305                 310                 315                 320

Asp Val Ser Gln Ala Gln Ala Gly Thr Tyr Ile Cys His Ile Arg Leu
                        325                 330                 335

Gln Gly Gln Gln Leu Asn Ala Thr Val Thr Leu Ala Ile Ile Thr Val
                        340                 345                 350

Thr Pro Lys Ser Phe Gly Ser Pro Gly Ser Leu Gly Lys Leu Leu Cys
                        355                 360                 365

Glu Val Thr Pro Ala Ser Gly Gln Glu His Phe Val Trp Ser Pro Leu
                        370                 375                 380

Asn Thr Pro Ser Gln Arg Ser Phe Ser Gly Pro Trp Leu Glu Ala Gln
        385                 390                 395                 400

Glu Ala Gln Leu Leu Ser Gln Pro Trp Gln Cys Gln Leu His Gln Gly
                        405                 410                 415

Glu Arg Leu Leu Gly Ala Ala Val Tyr Phe Thr Glu Leu Ser Ser Pro
                        420                 425                 430

Gly Ala Gln Arg Ser Gly Arg Ala Pro Gly Ala Leu Arg Ala Gly His
                        435                 440                 445

Leu Pro Leu Phe Leu Ile Leu Gly Val Leu Phe Leu Leu Leu Leu Val
                        450                 455                 460

Thr Gly Ala Phe Gly Phe His Leu Trp Arg Arg Gln Trp Arg Pro Arg
        465                 470                 475                 480

Arg Phe Ser Ala Leu Glu Gln Gly Ile His Pro Pro Gln Ala Gln Ser
                        485                 490                 495

Lys Ile Glu Glu Leu Glu Gln Glu Pro Glu Leu Glu Pro Glu Pro Glu
                        500                 505                 510

Leu Glu Arg Glu Leu Gly Pro Glu Pro Glu Pro Gly Pro Glu Pro Glu
                        515                 520                 525

Pro Glu Gln Leu
            530

<210> SEQ ID NO 94
<211> LENGTH: 533
<212> TYPE: PRT
<213> ORGANISM: Macaca mulatta

<400> SEQUENCE: 94

Met Trp Glu Ala Gln Phe Leu Gly Leu Leu Phe Leu Gln Pro Leu Trp
1               5                   10                  15

Val Ala Pro Val Lys Pro Pro Gln Pro Gly Ala Glu Ile Ser Val Val
                20                  25                  30

Trp Ala Gln Glu Gly Ala Pro Ala Gln Leu Pro Cys Ser Pro Thr Ile
                35                  40                  45

Pro Leu Gln Asp Leu Ser Leu Leu Arg Arg Ala Gly Val Thr Trp Gln
            50                  55                  60
```

```
His Gln Pro Asp Ser Gly Pro Pro Ala Pro Ala Pro Gly His Pro Pro
 65                  70                  75                  80

Ala Pro Gly His Arg Pro Ala Ala Pro Tyr Ser Trp Gly Pro Arg Pro
                 85                  90                  95

Arg Arg Tyr Thr Val Leu Ser Val Gly Pro Gly Leu Arg Ser Gly
            100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Ala Asp Ala
130                 135                 140

Gly Glu Tyr Arg Ala Thr Val His Leu Arg Asp Arg Ala Leu Ser Cys
145                 150                 155                 160

Arg Leu Arg Leu Arg Val Gly Gln Ala Ser Met Thr Ala Ser Pro Pro
                165                 170                 175

Gly Ser Leu Arg Thr Ser Asp Trp Val Ile Leu Asn Cys Ser Phe Ser
            180                 185                 190

Arg Pro Asp Arg Pro Ala Ser Val His Trp Phe Arg Ser Arg Gly Gln
            195                 200                 205

Gly Arg Val Pro Val Gln Gly Ser Pro His His Leu Ala Glu Ser
210                 215                 220

Phe Leu Phe Leu Pro His Val Gly Pro Met Asp Ser Gly Leu Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Ala Thr Pro Leu Thr Val Tyr Ala
            260                 265                 270

Gly Ala Gly Ser Arg Val Glu Leu Pro Cys Arg Leu Pro Pro Ala Val
            275                 280                 285

Gly Thr Gln Ser Phe Leu Thr Ala Lys Trp Ala Pro Pro Gly Gly Gly
            290                 295                 300

Pro Asp Leu Leu Val Ala Gly Asp Asn Gly Asp Phe Thr Leu Arg Leu
305                 310                 315                 320

Glu Asp Val Ser Gln Ala Gln Ala Gly Thr Tyr Ile Cys His Ile Arg
                325                 330                 335

Leu Gln Gly Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
            355                 360                 365

Cys Glu Val Thr Pro Ala Ser Gly Gln Glu His Phe Val Trp Ser Pro
370                 375                 380

Leu Asn Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu His Gln
                405                 410                 415

Gly Glu Thr Leu Leu Gly Ala Ala Val Tyr Phe Thr Glu Leu Ser Ser
            420                 425                 430

Pro Gly Ala Gln Arg Ser Gly Arg Ala Pro Gly Ala Leu Arg Ala Gly
            435                 440                 445

His Leu Pro Leu Phe Leu Ile Leu Gly Val Leu Phe Leu Leu Leu Leu
            450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
```

```
                        485                 490                 495
Ser Lys Ile Glu Glu Leu Glu Gln Glu Pro Glu Leu Pro Glu Pro
                    500                 505                 510

Glu Leu Glu Arg Glu Leu Gly Pro Glu Pro Glu Pro Gly Pro Glu Pro
                515                 520                 525

Glu Pro Glu Gln Leu
        530

<210> SEQ ID NO 95
<211> LENGTH: 525
<212> TYPE: PRT
<213> ORGANISM: Homo sapiens

<400> SEQUENCE: 95

Met Trp Glu Ala Gln Phe Leu Gly Leu Phe Leu Gln Pro Leu Trp
 1               5                  10                  15

Val Ala Pro Val Lys Pro Leu Gln Pro Gly Ala Glu Val Pro Val Val
                 20                  25                  30

Trp Ala Gln Glu Gly Ala Pro Ala Gln Leu Pro Cys Ser Pro Thr Ile
             35                  40                  45

Pro Leu Gln Asp Leu Ser Leu Leu Arg Arg Ala Gly Val Thr Trp Gln
 50                  55                  60

His Gln Pro Asp Ser Gly Pro Pro Ala Ala Ala Pro Gly His Pro Leu
 65                  70                  75                  80

Ala Pro Gly Pro His Pro Ala Ala Pro Ser Ser Trp Gly Pro Arg Pro
                 85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
        290                 295                 300

Pro Asp Leu Leu Val Thr Gly Asp Asn Gly Asp Phe Thr Leu Arg Leu
305                 310                 315                 320
```

```
Glu Asp Val Ser Gln Ala Gln Ala Gly Thr Tyr Thr Cys His Ile His
                325             330                 335

Leu Gln Glu Gln Gln Leu Asn Ala Thr Val Thr Leu Ala Ile Ile Thr
            340             345                 350

Val Thr Pro Lys Ser Phe Gly Ser Pro Gly Ser Leu Gly Lys Leu Leu
            355             360             365

Cys Glu Val Thr Pro Val Ser Gly Gln Glu Arg Phe Val Trp Ser Ser
    370             375             380

Leu Asp Thr Pro Ser Gln Arg Ser Phe Ser Gly Pro Trp Leu Glu Ala
385             390             395                         400

Gln Glu Ala Gln Leu Leu Ser Gln Pro Trp Gln Cys Gln Leu Tyr Gln
            405             410                 415

Gly Glu Arg Leu Leu Gly Ala Ala Val Tyr Phe Thr Glu Leu Ser Ser
            420             425             430

Pro Gly Ala Gln Arg Ser Gly Arg Ala Pro Gly Ala Leu Pro Ala Gly
            435             440             445

His Leu Leu Leu Phe Leu Ile Leu Gly Val Leu Ser Leu Leu Leu Leu
    450             455             460

Val Thr Gly Ala Phe Gly Phe His Leu Trp Arg Arg Gln Trp Arg Pro
465             470             475                         480

Arg Arg Phe Ser Ala Leu Glu Gln Gly Ile His Pro Pro Gln Ala Gln
                485             490                 495

Ser Lys Ile Glu Glu Leu Glu Gln Glu Pro Glu Pro Glu Pro Glu Pro
            500             505                 510

Glu Pro Glu Pro Glu Pro Glu Pro Glu Pro Glu Gln Leu
            515             520             525
```

HUMAN ANTIBODIES THAT BIND LYMPHOCYTE ACTIVATION GENE-3 (LAG-3), AND USES THEREOF

CROSS-REFERENCE TO RELATED APPLICATIONS

This application is a continuation of application Ser. No. 17/226,624, filed Apr. 9, 2021, now U.S. Pat. No. 11,236,165, which is a continuation of U.S. application Ser. No. 16/999,488, filed Aug. 21, 2020, now U.S. Pat. No. 11,001,630, which is a continuation of U.S. application Ser. No. 16/419,938, filed May 22, 2019, now U.S. Pat. No. 10,988,535, which is a divisional of U.S. application Ser. No. 15/730,363, filed Oct. 11, 2017, now U.S. Pat. No. 10,344,089, which is a divisional of U.S. application Ser. No. 13/058,492, 371(c) date Feb. 10, 2011, which is the National Stage of International Application No. PCT/US2009/053405, filed Aug. 11, 2009, which claims the benefit under 35 U.S.C. § 119(e) of U.S. Provisional Application No. 61/188,548, filed Aug. 11, 2008; the disclosures of each of which are incorporated herein by reference.

REFERENCE TO SEQUENCE LISTING SUBMITTED ELECTRONICALLY VIA EFS-WEB

The content of the electronically submitted sequence listing (Name: 3338_077000B_Seqlisting_ST25.txt; Size: 50,697 bytes; and Date of Creation: Jan. 24, 2022) is herein incorporated by reference in its entirety.

BACKGROUND OF THE INVENTION

Lymphocyte Activation Gene-3, or LAG-3 (also know as CD223), is a member of the immunoglobulin supergene family and is structurally and genetically related to CD4. LAG-3 is not expressed on resting peripheral blood lymphocytes but is expressed on activated T cells and NK cells. LAG-3 is a membrane protein encoded by a gene located on the distal part of the short arm of chromosome 12, near the CD4 gene, suggesting that the LAG-3 gene may have evolved through gene duplication (Triebel et al. (1990) *J. Exp. Med.* 171:1393-1405).

Similar to CD4, LAG-3 has been demonstrated to interact with MHC Class II molecules but, unlike CD4, LAG-3 does not interact with the human immunodeficiency virus gp120 protein (Baixeras et al. (1992) *J. Exp. Med.* 176:327-337). Studies using a soluble LAG-3 immunoglobulin fusion protein (sLAG-3Ig) demonstrated direct and specific binding of LAG-3 to MHC class II on the cell surface (Huard et al. (1996) *Eur. J. Immunol.* 26:1180-1186).

In in vitro studies of antigen-specific T cell responses, the addition of anti-LAG-3 antibodies led to increased T cell proliferation, higher expression of activation antigens such as CD25, and higher concentrations of cytokines such as interferon-gamma and interleukin-4, supporting a role for the LAG-/MHC class II interaction in down-regulating antigen-dependent stimulation of $CD4^+$ T lymphocytes (Huard et al. (1994) *Eur. J. Immunol.* 24:3216-3221). The intra-cytoplasmic region of LAG-3 has been demonstrated to interact with a protein termed LAP, which is thought to be a signal transduction molecule involved in the downregulation of the CD3/TCR activation pathway (Iouzalen et al. (2001) *Eur. J. Immunol.* 31:2885-2891). Furthermore, $CD4^+$ $CD25^+$ regulatory T cells ($T_{reg}$) have been shown to express LAG-3 upon activation and antibodies to LAG-3 inhibit suppression by induced $T_{reg}$ cells, both in vitro and in vivo, suggesting that LAG-3 contributes to the suppressor activity of $T_{reg}$ cells (Huang, C. et al. (2004) *Immunity* 21:503-513). Still further, LAG-3 has been shown to negatively regulate T cell homeostasis by regulatory T cells in both T cell-dependent and independent mechanisms (Workman, C. J. and Vignali, D. A. (2005) *J. Immunol.* 174:688-695).

In certain circumstances, LAG-3 also has been shown to have immunostimulatory effects. For example, LAG-3 transfected tumor cells transplanted into syngeneic mice showed marked growth reduction or complete regression as compared to untransfected tumor cells, suggesting that LAG-3 expression on the tumor cells stimulated an anti-tumor response by triggering antigen presenting cells via MHC class II molecules (Prigent et al. (1999) *Eur. J. Immunol.* 29:3867-3876). Additionally, soluble LAG-3 Ig fusion protein has been shown to stimulate both humoral and cellular immune responses when administered to mice together with an antigen, indicating that soluble LAG-3Ig can function as a vaccine adjuvant (El Mir and Triebel (2000) *J. Immunol.* 164:5583-5589). Furthermore, soluble human LAG-3Ig has been shown to amplify the in vitro generation of type I tumor-specific immunity (Casati et al. (2006) *Cancer Res.* 66:4450-4460). The functional activity of LAG-3 is reviewed further in Triebel (2003) *Trends Immunol.* 24:619-622. In view of the above, additional agents for modulating the activity of LAG-3 are of interest.

SUMMARY

The present disclosure provides isolated monoclonal antibodies, in particular human monoclonal antibodies, that specifically bind LAG-3 and that have desirable functional properties. These properties include high affinity binding to human LAG-3, binding to human and monkey LAG-3 (e.g., cynomolgus and/or rhesus monkey LAG-3) but not to mouse LAG-3, the ability to inhibit binding of LAG-3 to major histocompatibility (MHC) Class II molecules and/or the ability to stimulate antigen-specific T cell responses. The antibodies of the invention can be used, for example, to detect LAG-3 protein or to stimulate antigen-specific T cell responses, such as in a tumor-bearing subject or a virus-bearing subject.

In one aspect, the invention pertains to an isolated human monoclonal antibody, or an antigen-binding portion thereof, wherein the antibody binds human LAG-3 and exhibits at least one of the following properties:
 (a) binds monkey LAG-3;
 (b) does not bind mouse LAG-3;
 (c) inhibits binding of LAG-3 to major histocompatibility (MHC) class II molecules; and
 (d) stimulates an immune response.
Preferably, the antibody exhibits at least two of properties (a), (b), (c) and (d). More preferably, the antibody exhibits at least three of properties (a), (b), (c) and (d). Even more preferably, the antibody exhibits all four of properties (a), (b), (c) and (d).

In a preferred embodiment, the antibody stimulates an antigen-specific T cell response, such as interleukin-2 (IL-2) production in an antigen-specific T cell response. In other embodiments, the antibody stimulates an immune response such as an anti-tumor response (e.g., inhibits tumor growth in an in vivo tumor graft model) or an autoimmune response (e.g., promotes the development of diabetes in NOD mice). In another preferred embodiment, the antibody binds an epitope of human LAG-3 comprising the amino acid sequence PGHPLAPG (SEQ ID NO: 76). In yet another preferred embodiment, the antibody binds an epitope of human LAG-3 comprising the amino acid sequence HPAAPSSW (SEQ ID NO: 77) or PAAPSSWG (SEQ ID NO: 78). In still other embodiments, the antibody binds to human LAG-3 with a $K_D$ of $1\times10^{-7}$ M or less, or binds to human LAG-3 with a $K_D$ of $1\times10^{-8}$ M or less, or binds to human LAG-3 with a $K_D$ of $5\times10^{-9}$ M or less, or binds to human LAG-3 with a $K_D$ of $1\times10^{-9}$ M or less. In one embodiment, the antibody stains pituitary tissue by immunohistochemistry, whereas in another embodiment, the antibody does not stain pituitary tissue by immunohistochemistry.

In another aspect, the invention pertains to an isolated human monoclonal antibody, or antigen binding portion thereof, wherein the antibody cross-competes for binding to human LAG-3 with a reference antibody, wherein the reference antibody comprises:

(a) a heavy chain variable region comprising the amino acid sequence of SEQ ID NO: 37 and a light chain variable region comprising the amino acid sequence of SEQ ID NO: 43;

(b) a heavy chain variable region comprising the amino acid sequence of SEQ ID NO: 38 and a light chain variable region comprising the amino acid sequence of SEQ ID NO: 44;

(c) a heavy chain variable region comprising the amino acid sequence of SEQ ID NO: 39 and a light chain variable region comprising the amino acid sequence of SEQ ID NO: 45;

(d) a heavy chain variable region comprising the amino acid sequence of SEQ ID NO: 40 and a light chain variable region comprising the amino acid sequence of SEQ ID NO: 46;

(e) a heavy chain variable region comprising the amino acid sequence of SEQ ID NO: 41 and a light chain variable region comprising the amino acid sequence of SEQ ID NO: 47; or (f) a heavy chain variable region comprising the amino acid sequence of SEQ ID NO: 42 and a light chain variable region comprising the amino acid sequence of SEQ ID NO: 48.

In a preferred embodiment, the reference antibody comprises a heavy chain variable region comprising the amino acid sequence of SEQ ID NO: 37 and a light chain variable region comprising the amino acid sequence of SEQ ID NO: 43. In another preferred embodiment, the reference antibody comprises a heavy chain variable region comprising the amino acid sequence of SEQ ID NO: 38 and a light chain variable region comprising the amino acid sequence of SEQ ID NO: 44. In another preferred embodiment, the reference antibody comprises a heavy chain variable region comprising the amino acid sequence of SEQ ID NO: 39 and a light chain variable region comprising the amino acid sequence of SEQ ID NO: 45. In another preferred embodiment, the reference antibody comprises a heavy chain variable region comprising the amino acid sequence of SEQ ID NO: 40 and a light chain variable region comprising the amino acid sequence of SEQ ID NO: 46. In another preferred embodiment, the reference antibody comprises a heavy chain variable region comprising the amino acid sequence of SEQ ID NO: 41 and a light chain variable region comprising the amino acid sequence of SEQ ID NO: 47. In another preferred embodiment, the reference antibody comprises a heavy chain variable region comprising the amino acid sequence of SEQ ID NO: 42 and a light chain variable region comprising the amino acid sequence of SEQ ID NO: 48.

In another aspect, the invention pertains to an isolated monoclonal antibody, or an antigen-binding portion thereof, comprising a heavy chain variable region that is the product of or derived from a human $V_H$ 3-20 gene, a human $V_H$ 4-34 gene, a human $V_H$ 3-33 gene or a human $V_H$ 1-24 gene, wherein the antibody specifically binds human LAG-3. In another aspect, the invention pertains to an isolated monoclonal antibody, or an antigen-binding portion thereof, comprising a light chain variable region that is the product of or derived from a human $V_K$ L18 gene, a human $V_K$ L6 gene or a human $V_K$ A27 gene, wherein the antibody specifically binds human LAG-3. In a preferred embodiment, the invention provides an isolated monoclonal antibody, or an antigen-binding portion thereof, comprising:

(a) a heavy chain variable region that is the product of or derived from a human $V_H$ 4-34 gene and a light chain variable region that is the product of or derived from a human $V_K$ L6 gene;

(b) a heavy chain variable region that is the product of or derived from a human $V_H$ 3-33 gene and a light chain variable region that is the product of or derived from a human $V_K$ A27 gene;

(c) a heavy chain variable region that is the product of or derived from a human $V_H$ 3-20 gene and a light chain variable region that is the product of or derived from a human $V_K$ L18 gene;

(d) a heavy chain variable region that is the product of or derived from a human $V_H$ 1-24 gene and a light chain variable region that is the product of or derived from a human $V_K$ L6 gene; or (e) a heavy chain variable region that is the product of or derived from a human $V_H$ 3-33 gene and a light chain variable region that is the product of or derived from a human $V_K$ L6 gene;

wherein the antibody specifically binds human LAG-3.

In another aspect, the invention pertains to an isolated monoclonal antibody, or antigen binding portion thereof, comprising:

(a) a heavy chain variable region comprising an amino acid sequence selected from the group consisting of SEQ ID NOs: 37-42;

(b) a light chain variable region comprising an amino acid sequence selected from the group consisting of SEQ ID NOs: 43-48;

wherein the antibody specifically binds human LAG-3.

A preferred combination comprises:

(a) a heavy chain variable region comprising the amino acid sequence of SEQ ID NO: 37; and (b) a light chain variable region comprising the amino acid sequence of SEQ ID NO: 43.

Another preferred combination comprises:

(a) a heavy chain variable region comprising the amino acid sequence of SEQ ID NO: 38; and (b) a light chain variable region comprising the amino acid sequence of SEQ ID NO: 44.

Another preferred combination comprises:

(a) a heavy chain variable region comprising the amino acid sequence of SEQ ID NO: 39; and (b) a light chain variable region comprising the amino acid sequence of SEQ ID NO: 45.

Another preferred combination comprises:

(a) a heavy chain variable region comprising the amino acid sequence of SEQ ID NO: 40; and (b) a light chain variable region comprising the amino acid sequence of SEQ ID NO: 46.

Another preferred combination comprises:
(a) a heavy chain variable region comprising the amino acid sequence of SEQ ID NO: 41; and
(b) a light chain variable region comprising the amino acid sequence of SEQ ID NO: 47.

Another preferred combination comprises:
(a) a heavy chain variable region comprising the amino acid sequence of SEQ ID NO: 42; and
(b) a light chain variable region comprising the amino acid sequence of SEQ ID NO: 48.

The antibodies of the invention can be, for example, full-length antibodies, for example of an IgG1, IgG2 or IgG4 isotype. In a preferred embodiment, the antibody is an IgG4 isotype. In another preferred embodiment, the antibody is an IgG4 isotype having a serine to proline mutation in the heavy chain constant region hinge region (at a position corresponding to position 241 as described in Angal et al. (1993) *Mol. Immunol.* 30:105-108), such that inter-heavy chain disulfide bridge heterogeneity is reduced or abolished. Alternatively, the antibodies can be antibody fragments, such as Fab, Fab' or Fab'2 fragments, or single chain antibodies.

This disclosure also provides an immunoconjugate comprising an antibody of the invention, or antigen-binding portion thereof, linked to a therapeutic agent, e.g., a cytotoxin or a radioactive isotope. This disclosure also provides a bispecific molecule comprising an antibody, or antigen-binding portion thereof, of the invention, linked to a second functional moiety having a different binding specificity than said antibody, or antigen binding portion thereof.

Compositions comprising an antibody, or antigen-binding portion thereof, or immunoconjugate or bispecific molecule of the invention and a pharmaceutically acceptable carrier are also provided.

Nucleic acid molecules encoding the antibodies, or antigen-binding portions thereof, of the invention are also encompassed by this disclosure, as well as expression vectors comprising such nucleic acids and host cells comprising such expression vectors. Methods for preparing anti-LAG-3 antibodies using the host cells comprising such expression vectors are also provided and can include the steps of (i) expressing the antibody in the host cell and (ii) isolating the antibody from the host cell.

In another aspect, the invention pertains to methods of stimulating immune responses using the anti-LAG-3 antibodies of the invention. For example, in one embodiment, the invention provides a method of stimulating an antigen-specific T cell response comprising contacting said T cell with an antibody of the invention such that an antigen-specific T cell response is stimulated. In a preferred embodiment, interleukin-2 production by the antigen-specific T cell is stimulated. In another embodiment, the invention provides a method of stimulating an immune response (e.g., an antigen-specific T cell response) in a subject comprising administering an antibody of the invention to the subject such that an immune response (e.g., an antigen-specific T cell response) in the subject is stimulated. In a preferred embodiment, the subject is a tumor-bearing subject and an immune response against the tumor is stimulated. In another preferred embodiment, the subject is a virus-bearing subject and an immune response against the virus is stimulated.

In yet another aspect, the invention provides a method for inhibiting growth of tumor cells in a subject comprising administering to the subject an antibody of the invention such that growth of the tumor is inhibited in the subject. In still another aspect, the invention provides a method for treating viral infection in a subject comprising administering to the subject an antibody of the invention such that the viral infection is treated in the subject.

In yet another aspect, the invention provides a method for stimulating an immune response in a subject comprising administering to the subject an anti-LAG-3 antibody and at least one additional immunostimulatory antibody, such as an anti-PD-1 antibody, an anti-PD-L1 antibody and/or an anti-CTLA-4 antibody, such that an immune response is stimulated in the subject, for example to inhibit tumor growth or to stimulate an anti-viral response. In one embodiment, the subject is administered an anti-LAG-3 antibody and an anti-PD-1 antibody. In another embodiment, the subject is administered an anti-LAG-3 antibody and an anti-PD-L1 antibody. In yet another embodiment, the subject is administered an anti-LAG-3 antibody and an anti-CTLA-4 antibody. In one embodiment, the anti-LAG-3 antibody is a human antibody, such as an antibody of the disclosure. Alternatively, the anti-LAG-3 antibody can be, for example, a chimeric or humanized antibody. In another embodiment, the at least one additional immunostimulatory antibody (e.g., anti-PD-1, anti-PD-L1 and/or anti-CTLA-4 antibody) is a human antibody. Alternatively, the at least one additional immunostimulatory antibody can be, for example, a chimeric or humanized antibody.

In yet another aspect, the invention pertains to a method for preparing an anti-LAG-3 antibody. The method comprises:
(a) providing: (i) a heavy chain variable region antibody sequence comprising a CDR1 sequence selected from the group consisting of SEQ ID NOs: 1-6, a CDR2 sequence selected from the group consisting of SEQ ID NOs: 7-12, and/or a CDR3 sequence selected from the group consisting of SEQ ID NOs: 13-14, GGY and 16-18; and/or (ii) a light chain variable region antibody sequence comprising a CDR1 sequence selected from the group consisting of SEQ ID NOs: 19-24, a CDR2 sequence selected from the group consisting of SEQ ID NOs: 25-30, and/or a CDR3 sequence selected from the group consisting of SEQ ID NOs: 31-36;
(b) altering at least one amino acid residue within the heavy chain variable region antibody sequence and/or the light chain variable region antibody sequence to create at least one altered antibody sequence; and
(c) expressing the altered antibody sequence as a protein.

Other features and advantages of the instant disclosure will be apparent from the following detailed description and examples, which should not be construed as limiting. The contents of all references, Genbank entries, patents and published patent applications cited throughout this application are expressly incorporated herein by reference.

BRIEF DESCRIPTION OF THE DRAWINGS

FIG. 1A shows the nucleotide sequence (SEQ ID NO: 49) and amino acid sequence (SEQ ID NO: 37) of the heavy chain variable region of the 25F7 human monoclonal antibody. The CDR1 (SEQ ID NO: 1), CDR2 (SEQ ID NO: 7) and CDR3 (SEQ ID NO: 13) regions are delineated and the V, D and J germline derivations are indicated.

FIG. 1B shows the nucleotide sequence (SEQ ID NO: 55) and amino acid sequence (SEQ ID NO: 43) of the kappa light chain variable region of the 25F7 human monoclonal antibody. The CDR1 (SEQ ID NO: 19), CDR2 (SEQ ID NO: 25) and CDR3 (SEQ ID NO: 31) regions are delineated and the V and J germline derivations are indicated.

FIG. 2A shows the nucleotide sequence (SEQ ID NO: 50) and amino acid sequence (SEQ ID NO: 38) of the heavy chain variable region of the 26H10 human monoclonal antibody. The CDR1 (SEQ ID NO: 2), CDR2 (SEQ ID NO: 8) and CDR3 (SEQ ID NO: 14) regions are delineated and the V, D and J germline derivations are indicated.

FIG. 2B shows the nucleotide sequence (SEQ ID NO: 56) and amino acid sequence (SEQ ID NO: 44) of the kappa light chain variable region of the 26H10 human monoclonal antibody. The CDR1 (SEQ ID NO: 20), CDR2 (SEQ ID NO: 26) and CDR3 (SEQ ID NO: 32) regions are delineated and the V and J germline derivations are indicated.

FIG. 3A shows the nucleotide sequence (SEQ ID NO: 51) and amino acid sequence (SEQ ID NO: 39) of the heavy chain variable region of the 25E3 human monoclonal antibody. The CDR1 (SEQ ID NO: 3), CDR2 (SEQ ID NO: 9) and CDR3 regions are delineated and the V, D and J germline derivations are indicated.

FIG. 3B shows the nucleotide sequence (SEQ ID NO: 57) and amino acid sequence (SEQ ID NO: 45) of the kappa light chain variable region of the 25E3 human monoclonal antibody. The CDR1 (SEQ ID NO: 21), CDR2 (SEQ ID NO: 27) and CDR3 (SEQ ID NO: 33) regions are delineated and the V and J germline derivations are indicated.

FIG. 4A shows the nucleotide sequence (SEQ ID NO: 52) and amino acid sequence (SEQ ID NO: 40) of the heavy chain variable region of the 8B7 human monoclonal antibody. The CDR1 (SEQ ID NO: 4), CDR2 (SEQ ID NO: 10) and CDR3 (SEQ ID NO: 16) regions are delineated and the V, D and J germline derivations are indicated.

FIG. 4B shows the nucleotide sequence (SEQ ID NO: 58) and amino acid sequence (SEQ ID NO: 46) of the kappa light chain variable region of the 8B7 human monoclonal antibody. The CDR1 (SEQ ID NO: 22), CDR2 (SEQ ID NO: 28) and CDR3 (SEQ ID NO: 34) regions are delineated and the V and J germline derivations are indicated.

FIG. 5A shows the nucleotide sequence (SEQ ID NO: 53) and amino acid sequence (SEQ ID NO: 41) of the heavy chain variable region of the 11F2 human monoclonal antibody. The CDR1 (SEQ ID NO: 5), CDR2 (SEQ ID NO: 11) and CDR3 (SEQ ID NO: 17) regions are delineated and the V, D and J germline derivations are indicated.

FIG. 5B shows the nucleotide sequence (SEQ ID NO: 59) and amino acid sequence (SEQ ID NO: 47) of the kappa light chain variable region of the 11F2 human monoclonal antibody. The CDR1 (SEQ ID NO: 23), CDR2 (SEQ ID NO: 29) and CDR3 (SEQ ID NO: 35) regions are delineated and the V and J germline derivations are indicated.

FIG. 6A shows the nucleotide sequence (SEQ ID NO: 54) and amino acid sequence (SEQ ID NO: 42) of the heavy chain variable region of the 17E5 human monoclonal antibody. The CDR1 (SEQ ID NO: 6), CDR2 (SEQ ID NO: 12) and CDR3 (SEQ ID NO: 18) regions are delineated and the V, D and J germline derivations are indicated.

FIG. 6B shows the nucleotide sequence (SEQ ID NO: 60) and amino acid sequence (SEQ ID NO: 48) of the kappa light chain variable region of the 17E5 human monoclonal antibody. The CDR1 (SEQ ID NO: 24), CDR2 (SEQ ID NO: 30) and CDR3 (SEQ ID NO: 36) regions are delineated and the V and J germline derivations are indicated.

FIG. 7 shows the alignment of the amino acid sequence of the heavy chain variable regions of 25F7 (SEQ ID NO: 37) with the human germline $V_H$ 4-34 and JH5b amino acid sequences (SEQ ID NOS: 61 and 62, respectively).

FIG. 8 shows the alignment of the amino acid sequence of the light chain variable region of 25F7 (SEQ ID NO: 43) with the human germline $V_k$ L6 and JK2 amino acid sequences (SEQ ID NOS: 63 and 64, respectively).

FIG. 9 shows the alignment of the amino acid sequence of the heavy chain variable regions of 26H10 (SEQ ID NO: 38) with the human germline $V_H$ 3-33 and JH6B amino acid sequences (SEQ ID NOS: 65 and 66, respectively).

FIG. 10 shows the alignment of the amino acid sequence of the light chain variable region of 26H10 (SEQ ID NO: 44) with the human germline $V_k$ A27 and JK3 amino acid sequences (SEQ ID NO: 67 and 68, respectively).

FIG. 11 shows the alignment of the amino acid sequence of the heavy chain variable regions of 25E3 (SEQ ID NO: 39) with the human germline $V_H$ 3-20 and JH4b amino acid sequences (SEQ ID NOS: 69 and 70, respectively).

FIG. 12 shows the alignment of the amino acid sequence of the light chain variable region of 25E3 (SEQ ID NO: 45) with the human germline $V_k$ L18 and JK2 amino acid sequences (SEQ ID NOS: 71 and 64, respectively).

FIG. 13 shows the alignment of the amino acid sequence of the heavy chain variable regions of 8B7 (SEQ ID NO: 40) with the human germline $V_H$ 4-34 and JH5b amino acid sequences (SEQ ID NOS: 61 and 62, respectively).

FIG. 14 shows the alignment of the amino acid sequence of the light chain variable region of 8B7 (SEQ ID NO: 46) with the human germline $V_k$ L6 and JK4 amino acid sequences (SEQ ID NOS: 63 and 72, respectively).

FIG. 15 shows the alignment of the amino acid sequence of the heavy chain variable regions of 11F2 (SEQ ID NO: 41) with the human germline $V_H$ 1-24 and JH4b amino acid sequences (SEQ ID NOS: 73 and 70, respectively).

FIG. 16 shows the alignment of the amino acid sequence of the light chain variable region of 11F2 (SEQ ID NO: 47) with the human germline $V_k$ L6 and JK1 amino acid sequences (SEQ ID NOS: 63 and 74, respectively).

FIG. 17 shows the alignment of the amino acid sequence of the heavy chain variable regions of 17E5 (SEQ ID NO: 42) with the human germline $V_H$ 3-33 and 2-2 amino acid sequences (SEQ ID NOS: 65 and 70, respectively).

FIG. 18 shows the alignment of the amino acid sequence of the light chain variable region of 17E5 (SEQ ID NO: 48) with the human germline $V_k$ L6 amino acid sequence (SEQ ID NOS: 63 and 75, respectively).

FIGS. 19A and B show the alignment of the protein sequence encoded by the monkey LAG-3 cDNA clone pa23-5 (SEQ ID NO: 93) with the Genbank deposited rhesus monkey LAG-3 protein sequence (SEQ ID NO: 94) (Genbank Accession No. XM_001108923). The extra loop peptide region and transmembrane domain are underlined. The one amino acid difference between the two sequences (amino acid position 419) is highlighted in bold.

DETAILED DESCRIPTION OF THE INVENTION

The present disclosure relates to isolated monoclonal antibodies, particularly human monoclonal antibodies, which bind to human LAG-3 and that have desirable functional properties. In certain embodiments, the antibodies of the invention are derived from particular heavy and light chain germline sequences and/or comprise particular structural features such as CDR regions comprising particular amino acid sequences. This disclosure provides isolated antibodies, methods of making such antibodies, immunoconjugates and bispecific molecules comprising such antibodies and pharmaceutical compositions containing the antibodies, immunoconjugates or bispecific molecules of the invention. This disclosure also relates to methods of using the antibodies, such as to detect LAG-3 protein, as well as to methods of using the anti-LAG-3 antibodies of the invention to stimulate immune responses, alone or in combination with other immunostimulatory antibodies. Accordingly, this disclosure also provides methods of using the anti-LAG-3 antibodies of the invention to, for example, inhibit tumor growth or treat viral infection.

In order that the present disclosure may be more readily understood, certain terms are first defined. Additional definitions are set forth throughout the detailed description.

The term "LAG-3" refers to Lymphocyte Activation Gene-3. The term "LAG-3" includes variants, isoforms, homologs, orthologs and paralogs. For example, antibodies specific for a human LAG-3 protein may, in certain cases, cross-react with a LAG-3 protein from a species other than human. In other embodiments, the antibodies specific for a human LAG-3 protein may be completely specific for the human LAG-3 protein and may not exhibit species or other types of cross-reactivity, or may cross-react with LAG-3 from certain other species but not all other species (e.g., cross-react with monkey LAG-3 but not mouse LAG-3). The term "human LAG-3" refers to human sequence LAG-3, such as the complete amino acid sequence of human LAG-3 having Genbank Accession No. NP_002277. The term "mouse LAG-3" refers to mouse sequence LAG-3, such as the complete amino acid sequence of mouse LAG-3 having Genbank Accession No. NP_032505. LAG-3 is also known in the art as, for example, CD223. The human LAG-3 sequence may differ from human LAG-3 of Genbank Accession No. NP_002277 by having, e.g., conserved mutations or mutations in non-conserved regions and the LAG-3 has substantially the same biological function as the human LAG-3 of Genbank Accession No. NP_002277. For example, a biological function of human LAG-3 is having an epitope in the extracellular domain of LAG-3 that is specifically bound by an antibody of the instant disclosure or a biological function of human LAG-3 is binding to MHC Class II molecules.

The term "monkey LAG-3" is intended to encompass LAG-3 proteins expressed by Old World and New World monkeys, including but not limited to cynomolgus monkey LAG-3 and rhesus monkey LAG-3. A representative amino acid sequence for monkey LAG-3 is the rhesus monkey LAG-3 amino acid sequence shown in FIG. 19 and SEQ ID NO: 85, which is also deposited as Genbank Accession No. XM_001108923. Another representative amino acid sequence for monkey LAG-3 is the alternative rhesus monkey sequence of clone pa23-5 shown in FIG. 19 and SEQ ID NO: 84, isolated as described in Example 3A, subsection 3. This alternative rhesus sequence exhibits a single amino acid difference, at position 419, as compared to the Genbank-deposited sequence.

A particular human LAG-3 sequence will generally be at least 90% identical in amino acids sequence to human LAG-3 of Genbank Accession No. NP_002277 and contains amino acid residues that identify the amino acid sequence as being human when compared to LAG-3 amino acid sequences of other species (e.g., murine). In certain cases, a human LAG-3 can be at least 95%, or even at least 96%, 97%, 98%, or 99% identical in amino acid sequence to LAG-3 of Genbank Accession No. NP_002277. In certain embodiments, a human LAG-3 sequence will display no more than 10 amino acid differences from the LAG-3 sequence of Genbank Accession No. NP_002277. In certain embodiments, the human LAG-3 can display no more than 5, or even no more than 4, 3, 2, or 1 amino acid difference from the LAG-3 sequence of Genbank Accession No. NP_002277. Percent identity can be determined as described herein.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

An "antigen-specific T cell response" refers to responses by a T cell that result from stimulation of the T cell with the antigen for which the T cell is specific. Non-limiting examples of responses by a T cell upon antigen-specific stimulation include proliferation and cytokine production (e.g., IL-2 production).

The term "antibody" as referred to herein includes whole antibodies and any antigen binding fragment (i.e., "antigen-binding portion") or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., a LAG-3 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., 3.sup.rd ed. 1993); (iv) a Fd fragment consisting of the $V_H$ and $C_H1$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a LAG-3 protein is substantially free of antibodies that specifically bind antigens other than LAG-3 proteins). An isolated antibody that specifically binds a human LAG-3 protein may, however, have cross-reactivity to other antigens, such as LAG-3 proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity, which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications can be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds human LAG-3" is intended to refer to an antibody that binds to human LAG-3 protein (and possibly a LAG-3 protein from one or more non-human species) but does not substantially bind to non-LAG-3 proteins. Preferably, the antibody binds to a human LAG-3 protein with "high affinity", namely with a $K_D$ of $1\times10^{-7}$ M or less, more preferably $5\times10^{-8}$ M or less, more preferably $3\times10^{-8}$ M or less, more preferably $1\times10^{-8}$ M or less, more preferably $5\times10^{-9}$ M or less or even more preferably $1\times10^{-9}$ M or less.

The term "does not substantially bind" to a protein or cells, as used herein, means does not bind or does not bind with a high affinity to the protein or cells, i.e. binds to the protein or cells with a $K_D$ of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$," as used herein, is intended to refer to the dissociation constant, which is obtained from the ratio of Kato $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

The term "high affinity" for an IgG antibody refers to an antibody having a $K_D$ of $1\times10^{-7}$ M or less, more preferably $5\times10^{-8}$ M or less, even more preferably $1\times10^{-8}$ M or less, even more preferably $5\times10^{-9}$ M or less and even more preferably $1\times10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

Various aspects of the invention are described in further detail in the following subsections.

Anti-LAG-3 Antibodies Having Particular Functional Properties

The antibodies of the invention are characterized by particular functional features or properties of the antibodies. For example, the antibodies specifically bind to human LAG-3 and may bind to LAG-3 from certain other species, e.g., monkey LAG-3 (e.g., cynomolgus monkey, rhesus monkey), but do not substantially bind to LAG-3 from certain other species, e.g., mouse LAG-3. Preferably, an antibody of the invention binds to human LAG-3 with high affinity.

The ability of the antibody to stimulate an immune response, such as an antigen-specific T cell response, can be indicated by, for example, the ability of the antibody to stimulate interleukin-2 (IL-2) production in an antigen-specific T cell response. In certain embodiments, an antibody of the invention binds to human LAG-3 and exhibits an ability to stimulate an antigen-specific T cell response. In other embodiments, an antibody of the invention binds to human LAG-3 but does not exhibit an ability to stimulate an antigen-specific T cell response. Other means by which to evaluate the ability of the antibody to stimulate an immune response include the ability of the antibody to inhibit tumor growth, such as in an in vivo tumor graft model (see, e.g., Example 6) or the ability of the antibody to stimulate an autoimmune response, such as the ability to promote the development of an autoimmune disease in an autoimmune model, such as the ability to promote the development of diabetes in the NOD mouse model (see, e.g., Example 7).

The binding of an antibody of the invention to LAG-3 can be assessed using one ore more techniques well established in the art. For example, in a preferred embodiment, an antibody can be tested by a flow cytometry assay in which the antibody is reacted with a cell line that expresses human LAG-3, such as CHO cells that have been transfected to express LAG-3 (e.g., human LAG-3, or monkey LAG-3 (e.g., rhesus or cynomolgus monkey) or mouse LAG-3) on their cell surface (see, e.g., Example 3A for a suitable assay). Other suitable cells for use in flow cytometry assays include anti-CD3-stimulated CD4$^+$ activated T cells, which express native LAG-3. Additionally or alternatively, the binding of the antibody, including the binding kinetics (e.g., $K_D$ value) can be tested in BIAcore binding assays (see, e.g., Example 3B for suitable assays). Still other suitable binding assays include ELISA assays, for example using a recombinant LAG-3 protein (see, e.g., Example 1 for a suitable assay).

Preferably, an antibody of the invention binds to a LAG-3 protein with a $K_D$ of $5\times10^{-8}$ M or less, binds to a LAG-3 protein with a $K_D$ of $2\times10^{-8}$ M or less, binds to a LAG-3 protein with a $K_D$ of $5\times10^{-9}$ M or less, binds to a LAG-3 protein with a $K_D$ of $4\times10^{-9}$ M or less, binds to a LAG-3 protein with a $K_D$ of $3\times10^{-9}$ M or less, binds to a LAG-3 protein with a $K_D$ of $2\times10^{-9}$ M or less, binds to a LAG-3 protein with a $K_D$ of $1\times10^{-9}$ M or less, binds to a LAG-3 protein with a $K_D$ of $5\times10^{-10}$ M or less, or binds to a LAG-3 protein with a $K_D$ of $1\times10^{-10}$ M or less.

Typically, an antibody of the invention binds to LAG-3 in lymphoid tissues, such as tonsil, spleen or thymus, which can be detected by immunohistochemistry. Additionally, as described further in Example 8, certain anti-LAG-3 antibodies of the invention stain pituitary tissue (e.g., are retained in the pituitary) as measured by immunohistochemistry, whereas other anti-LAG-3 antibodies of the invention do not stain pituitary tissue (e.g., are not retained in the pituitary) as measured by immunohistochemistry. Thus, in one embodiment, the invention provides a human anti-LAG-3 antibody that stains pituitary tissue by immunohistochemistry, whereas in another embodiment, the invention provides a human anti-LAG-3 antibody that does not stain pituitary tissue by immunohistochemistry.

Preferred antibodies of the invention are human monoclonal antibodies. Additionally or alternatively, the antibodies can be, for example, chimeric or humanized monoclonal antibodies.

Monoclonal Antibodies 25F7, 26H10, 25E3, 8B7, 11F2 and 17E5

Preferred antibodies of the invention are the human monoclonal antibodies 25F7, 26H10, 25E3, 8B7, 11F2 and 17E5 isolated and structurally characterized as described in Examples 1 and 2. The $V_H$ amino acid sequences of 25F7, 26H10, 25E3, 8B7, 11F2 and 17E5 are shown in SEQ ID NOs: 37-42, respectively. The $V_K$ amino acid sequences of 25F7, 26H10, 25E3, 8B7, 11F2 and 17E5 are shown in SEQ ID NOs: 43-48, respectively.

Given that each of these antibodies can bind to human LAG-3, the $V_H$ and $V_L$ sequences can be "mixed and matched" to create other anti-LAG-3 binding molecules of the invention. Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one aspect, this disclosure provides an isolated monoclonal antibody, or antigen binding portion thereof comprising:

(a) a heavy chain variable region comprising an amino acid sequence selected from the group consisting of SEQ ID NOs: 37-42; and (b) a light chain variable region comprising an amino acid sequence selected from the group consisting of SEQ ID NOs: 43-48;

wherein the antibody specifically binds human LAG-3.

Preferred heavy and light chain combinations include:

(a) a heavy chain variable region comprising the amino acid sequence of SEQ ID NO: 37 and a light chain variable region comprising the amino acid sequence of SEQ ID NO: 43;

(b) a heavy chain variable region comprising the amino acid sequence of SEQ ID NO: 38 and a light chain variable region comprising the amino acid sequence of SEQ ID NO: 44;

(c) a heavy chain variable region comprising the amino acid sequence of SEQ ID NO: 39 and a light chain variable region comprising the amino acid sequence of SEQ ID NO: 45;

(d) a heavy chain variable region comprising the amino acid sequence of SEQ ID NO: 40 and a light chain variable region comprising the amino acid sequence of SEQ ID NO: 46;

(e) a heavy chain variable region comprising the amino acid sequence of SEQ ID NO: 41 and a light chain variable region comprising the amino acid sequence of SEQ ID NO: 47; or (f) a heavy chain variable region comprising the amino acid sequence of SEQ ID NO: 42 and a light chain variable region comprising the amino acid sequence of SEQ ID NO: 48.

In another aspect, this disclosure provides antibodies that comprise the heavy chain and light chain CDR1s, CDR2s and CDR3s of 25F7, 26H10, 25E3, 8B7, 11F2 or 17E5, or combinations thereof. The amino acid sequences of the $V_H$ CDR1s of 25F7, 26H10, 25E3, 8B7, 11F2 and 17E5 are shown in SEQ ID NOs: 37-42, respectively. The amino acid sequences of the $V_H$ CDR2s of 25F7, 26H10, 25E3, 8B7, 11F2 and 17E5 are shown in SEQ ID NOs: 43-48, respectively. The amino acid sequences of the $V_H$ CDR3s of 25F7, 26H10, 25E3, 8B7, 11F2 and 17E5 are shown in SEQ ID NOs: 13-14, GGY and 16-18, respectively. The amino acid sequences of the $V_K$ CDR1s of 25F7, 26H10, 25E3, 8B7, 11F2 and 17E5 are shown in SEQ ID NOs: 19-24 respectively. The amino acid sequences of the $V_K$ CDR2s of 25F7, 26H10, 25E3, 8B7, 11F2 and 17E5 are shown in SEQ ID NOs: 25-30. The amino acid sequences of the $V_K$ CDR3s of 25F7, 26H10, 25E3, 8B7, 11F2 and 17E5 are shown in SEQ ID NOs: 31-36, respectively. The CDR regions are delineated using the Kabat system (Kabat et al. (1991) Sequences of Proteins of Immunological Interest, Fifth Edition, U.S. Department of Health and Human Services, NIH Publication No. 91-3242).

Given that each of these antibodies can bind to human LAG-3 and that antigen-binding specificity is provided primarily by the CDR1, CDR2, and CDR3 regions, the $V_H$ CDR1, CDR2, and CDR3 sequences and $V_L$ CDR1, CDR2, and CDR3 sequences can be "mixed and matched" (i.e., CDRs from different antibodies can be mixed and match, although each antibody must contain a $V_H$ CDR1, CDR2, and CDR3 and a $V_L$ CDR1, CDR2, and CDR3) to create other anti-LAG-3 binding molecules of the invention. LAG-3 binding of such "mixed and matched" antibodies can be tested using the binding assays described above and in the Examples (e.g., ELISAs, Biacore® analysis). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_L$ CDR sequences are mixed and matched, the CDR1, CDR2 and/or CDR3 sequence from a particular $V_L$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies 25F7, 26H10, 25E3, 8B7, 11F2 and 17E5.

Accordingly, in another aspect, this disclosure provides an isolated monoclonal antibody, or antigen binding portion thereof comprising:

(a) a heavy chain variable region CDR1 comprising an amino acid sequence selected from the group consisting of SEQ ID NOs: 1-6;

(b) a heavy chain variable region CDR2 comprising an amino acid sequence selected from the group consisting of SEQ ID NOs: 7-12;

(c) a heavy chain variable region CDR3 comprising an amino acid sequence selected from the group consisting of SEQ ID NOs: 13-14, GGY and 16-18;

(d) a light chain variable region CDR1 comprising an amino acid sequence selected from the group consisting of SEQ ID NOs: 19-24;

(e) a light chain variable region CDR2 comprising an amino acid sequence selected from the group consisting of SEQ ID NOs: 25-30; and (f) a light chain variable region CDR3 comprising an amino acid sequence selected from the group consisting of SEQ ID NOs: 31-36;

wherein the antibody specifically binds human LAG-3.

In a preferred embodiment, the antibody comprises:
(a) a heavy chain variable region CDR1 comprising SEQ ID NO: 1;
(b) a heavy chain variable region CDR2 comprising SEQ ID NO: 7;
(c) a heavy chain variable region CDR3 comprising SEQ ID NO: 13;
(d) a light chain variable region CDR1 comprising SEQ ID NO: 19;
(e) a light chain variable region CDR2 comprising SEQ ID NO: 25; and
(f) a light chain variable region CDR3 comprising SEQ ID NO: 31.

In another preferred embodiment, the antibody comprises:
(a) a heavy chain variable region CDR1 comprising SEQ ID NO: 2;
(b) a heavy chain variable region CDR2 comprising SEQ ID NO: 8;
(c) a heavy chain variable region CDR3 comprising SEQ ID NO: 14;
(d) a light chain variable region CDR1 comprising SEQ ID NO: 20;
(e) a light chain variable region CDR2 comprising SEQ ID NO: 26; and
(f) a light chain variable region CDR3 comprising SEQ ID NO: 32.

In another preferred embodiment, the antibody comprises:
(a) a heavy chain variable region CDR1 comprising SEQ ID NO: 3;
(b) a heavy chain variable region CDR2 comprising SEQ ID NO: 9;
(c) a heavy chain variable region CDR3 comprising GGY;
(d) a light chain variable region CDR1 comprising SEQ ID NO: 21;
(e) a light chain variable region CDR2 comprising SEQ ID NO: 27; and
(f) a light chain variable region CDR3 comprising SEQ ID NO: 33.

In another preferred embodiment, the antibody comprises:
(a) a heavy chain variable region CDR1 comprising SEQ ID NO: 4;
(b) a heavy chain variable region CDR2 comprising SEQ ID NO: 10;
(c) a heavy chain variable region CDR3 comprising SEQ ID NO: 16;
(d) a light chain variable region CDR1 comprising SEQ ID NO: 22;
(e) a light chain variable region CDR2 comprising SEQ ID NO: 28; and
(f) a light chain variable region CDR3 comprising SEQ ID NO: 34.

In another preferred embodiment, the antibody comprises:
(a) a heavy chain variable region CDR1 comprising SEQ ID NO: 5;
(b) a heavy chain variable region CDR2 comprising SEQ ID NO: 11;
(c) a heavy chain variable region CDR3 comprising SEQ ID NO: 17;
(d) a light chain variable region CDR1 comprising SEQ ID NO: 23;

(e) a light chain variable region CDR2 comprising SEQ ID NO: 29; and (f) a light chain variable region CDR3 comprising SEQ ID NO: 35.

In another preferred embodiment, the antibody comprises:

(a) a heavy chain variable region CDR1 comprising SEQ ID NO: 6;

(b) a heavy chain variable region CDR2 comprising SEQ ID NO: 12;

(c) a heavy chain variable region CDR3 comprising SEQ ID NO: 18;

(d) a light chain variable region CDR1 comprising SEQ ID NO: 24;

(e) a light chain variable region CDR2 comprising SEQ ID NO: 30; and (f) a light chain variable region CDR3 comprising SEQ ID NO: 36.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al., *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIAjournal* 8:Scientific Review 8 (2001); Igarashi et al., *J. Biochem (Tokyo)* 117:452-7 (1995); Bourgeois et al., *J. Virol* 72:807-10 (1998); Levi et al., *Proc. Nat. Acad. Sci. U.S.A.* 90:4374-8 (1993); Polymenis and Stoller, *J. Immunol.* 152: 5218-5329 (1994) and Xu and Davis, Immunity 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, the present disclosure provides monoclonal antibodies comprising one or more heavy and/or light chain CDR3 domains from an antibody derived from a human or non-human animal, wherein the monoclonal antibody is capable of specifically binding to human LAG-3. Within certain aspects, the present disclosure provides monoclonal antibodies comprising one or more heavy and/or light chain CDR3 domain from a non-human antibody, such as a mouse or rat antibody, wherein the monoclonal antibody is capable of specifically binding to LAG-3. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

Within other aspects, the present disclosure provides monoclonal antibodies comprising one or more heavy and/or light chain CDR3 domain from a human antibody, such as, e.g., a human antibody obtained from a non-human animal, wherein the human antibody is capable of specifically binding to human LAG-3. Within other aspects, the present disclosure provides monoclonal antibodies comprising one or more heavy and/or light chain CDR3 domain from a first human antibody, such as, for example, a human antibody obtained from a non-human animal, wherein the first human antibody is capable of specifically binding to human LAG-3 and wherein the CDR3 domain from the first human antibody replaces a CDR3 domain in a human antibody that is lacking binding specificity for LAG-3 to generate a second human antibody that is capable of specifically binding to human LAG-3. Within some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody.

Antibodies Having Particular Germline Sequences

In certain embodiments, an antibody of the invention comprises a heavy chain variable region from a particular germline heavy chain immunoglobulin gene and/or a light chain variable region from a particular germline light chain immunoglobulin gene.

For example, in a preferred embodiment, this disclosure provides an isolated monoclonal antibody, or an antigen-binding portion thereof, comprising a heavy chain variable region that is the product of or derived from a human $V_H$ 3-20 gene, a human $V_H$ 4-34 gene, a human $V_H$ 3-33 gene or a human $V_H$ 1-24 gene, wherein the antibody specifically binds human LAG-3. In another preferred embodiment, this disclosure provides an isolated monoclonal antibody, or an antigen-binding portion thereof, comprising a light chain variable region that is the product of or derived from a human $V_K$ L18 gene, a human $V_K$ L6 gene or a human $V_K$ A27 gene, wherein the antibody specifically binds human LAG-3. In yet another preferred embodiment, this disclosure provides an isolated monoclonal antibody, or antigen-binding portion thereof, wherein the antibody comprises a heavy chain variable region that is the product of or derived from a human $V_H$ 3-20 gene and comprises a light chain variable region that is the product of or derived from a human $V_K$ L18 gene, wherein the antibody specifically binds human LAG-3. In yet another preferred embodiment, this disclosure provides an isolated monoclonal antibody, or antigen-binding portion thereof, wherein the antibody comprises a heavy chain variable region that is the product of or derived from a human $V_H$ 4-34 gene and comprises a light chain variable region that is the product of or derived from a human $V_K$ L6 gene, wherein the antibody specifically binds human LAG-3. In yet another preferred embodiment, this disclosure provides an isolated monoclonal antibody, or antigen-binding portion thereof, wherein the antibody comprises a heavy chain variable region that is the product of or derived from a human $V_H$ 3-33 gene and comprises a light chain variable region that is the product of or derived from a human $V_K$ A27 gene, wherein the antibody specifically binds human LAG-3. In yet another preferred embodiment, this disclosure provides an isolated monoclonal antibody, or antigen-binding portion thereof, wherein the antibody comprises a heavy chain variable region that is the product of or derived from a human $V_H$ 1-24 gene and comprises a light chain variable region that is the product of or derived from a human $V_K$ L6 gene, wherein the antibody specifically binds human LAG-3. In yet another preferred embodiment, this disclosure provides an isolated monoclonal antibody, or antigen-binding portion thereof, wherein the antibody comprises a heavy chain variable region that is the product of or derived from a human $V_H$ 3-33 gene and comprises a light chain variable region that is the product of or derived from a human $V_K$ L6 gene, wherein the antibody specifically binds human LAG-3.

Such antibodies can also possess one or more of the functional characteristics described in detail above, such as high affinity binding to human LAG-3, binding to monkey LAG-3, lack of binding to mouse LAG-3, the ability to inhibit binding of LAG-3 to MHC Class II molecules and/or the ability to stimulate antigen-specific T cell responses.

An example of an antibody having $V_H$ and $V_L$ of $V_H$ 3-20 and $V_K$ L18, respectively, is the 25E3 antibody. Examples of antibodies having $V_H$ and $V_L$ of $V_H$ 4-34 and $V_K$ L6, respectively, are the 25F7 and 8B7 antibodies. An example of an antibody having $V_H$ and $V_L$ of $V_H$ 3-33 and $V_K$ A27, respectively, is the 26H10 antibody. An example of an antibody having $V_H$ and $V_L$ of $V_H$ 1-24 and $V_K$ L6, respectively, is the 11F2 antibody. An example of an antibody having $V_H$ and $V_L$ of $V_H$ 3-33 and $V_K$ L6, respectively, is the 17E5 antibody.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence can contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody can be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody can display no more than 5, or even no more than 4, 3, 2, or 1 amino acid difference from the amino acid sequence encoded by the germline immunoglobulin gene.

Homologous Antibodies

In yet another embodiment, an antibody of the invention comprises heavy and light chain variable regions comprising amino acid sequences that are homologous to the amino acid sequences of the preferred antibodies described herein, and wherein the antibodies retain the desired functional properties of the anti-LAG-3 antibodies of the invention. For example, this disclosure provides an isolated monoclonal antibody, or antigen binding portion thereof, comprising a heavy chain variable region and a light chain variable region, wherein:

(a) the heavy chain variable region comprises an amino acid sequence that is at least 80% homologous to an amino acid sequence selected from the group consisting of SEQ ID NOs: 37-42;

(b) the light chain variable region comprises an amino acid sequence that is at least 80% homologous to an amino acid sequence selected from the group consisting of SEQ ID NOs: 43-48; and (c) the antibody specifically binds to human LAG-3.

Additionally or alternatively, the antibody can possess one or more of the following functional properties discussed above, such as high affinity binding to human LAG-3, binding to monkey LAG-3, lack of binding to mouse LAG-3, the ability to inhibit binding of LAG-3 to MHC Class II molecules and/or the ability to stimulate antigen-specific T cell responses.

In various embodiments, the antibody can be, for example, a human antibody, a humanized antibody or a chimeric antibody.

In other embodiments, the $V_H$ and/or $V_L$ amino acid sequences can be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding SEQ ID NOs: 49-54 or 55-60, followed by testing of the encoded altered antibody for retained function (i.e., the functions set forth above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present disclosure can further be used as a "query sequence" to perform a search against public databases to, e.g., to identify related sequences. Such searches can be performed using the XBLAST program (version 2.0) of Altschul et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) are useful. See www.ncbi.nlm.nih.gov.

Antibodies with Conservative Modifications

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 25F7, 26H10, 25E3, 8B7, 11F2, 17E5), or conservative modifications thereof, and wherein the antibodies retain the desired functional properties of the anti-LAG-3 antibodies of the invention. It is understood in the art that certain conservative sequence modification can be made which do not remove antigen binding. See, e.g., Brummell et al. (1993) Biochem 32:1180-8; de Wildt et al. (1997) Prot. Eng. 10:835-41; Komissarov et al. (1997) J. Biol. Chem. 272:26864-26870; Hall et al. (1992) J. Immunol. 149:1605-12; Kelley and O'Connell (1993) Biochem. 32:6862-35; Adib-Conquy et al. (1998) Int. Immunol. 10:341-6 and Beers et al. (2000) Clin. Can. Res. 6:2835-43. Accordingly, this disclosure provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of amino acid sequences of SEQ ID NOs: 13-14, GGY and 16-18, and conservative modifications thereof, (b) the light chain variable region CDR3 sequence comprises an amino acid sequence selected from the group consisting of amino acid sequence of SEQ ID NOs: 31-36, and conservative modifications thereof, and (c) the antibody specifically binds human LAG-3.

Additionally or alternatively, the antibody can possess one or more of the following functional properties described above, such as high affinity binding to human LAG-3, binding to monkey LAG-3, lack of binding to mouse LAG-3, the ability to inhibit binding of LAG-3 to MHC Class II molecules and/or the ability to stimulate antigen-specific T cell responses.

In a preferred embodiment, the heavy chain variable region CDR2 sequence comprises an amino acid sequence selected from the group consisting of amino acid sequences of SEQ ID NOs: 7-12, and conservative modifications thereof, and the light chain variable region CDR2 sequence comprises an amino acid sequence selected from the group consisting of amino acid sequences of SEQ ID NOs: 25-30, and conservative modifications thereof. In another preferred embodiment, the heavy chain variable region CDR1 sequence comprises an amino acid sequence selected from the group consisting of amino acid sequences of SEQ ID NOs: 1-6, and conservative modifications thereof, and the light chain variable region CDR1 sequence comprises an amino acid sequence selected from the group consisting of amino acid sequences of SEQ ID NOs: 19-24, and conservative modifications thereof.

In various embodiments, the antibody can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth above) using the functional assays described herein.

Antibodies that Bind to the Same Epitope as Anti-LAG-3 Antibodies

In another embodiment, this disclosure provides antibodies that bind to the same epitope on LAG-3 as any of the anti-LAG-3 monoclonal antibodies of the invention (i.e., antibodies that have the ability to cross-compete for binding to human LAG-3 with any of the monoclonal antibodies of the invention). In preferred embodiments, the reference antibody for cross-competition studies can be the monoclonal antibodies 25F7, 26H10, 25E3, 8B7, 11F2 or 17E5.

Such cross-competing antibodies can be identified based on their ability to cross-compete with 25F7, 26H10, 25E3, 8B7, 11F2 and/or 17E5 in standard LAG-3 binding assays. For example, standard ELISA assays can be used in which a recombinant human LAG-3 protein is immobilized on the plate, one of the antibodies is fluorescently labeled and the ability of non-labeled antibodies to compete off the binding of the labeled antibody is evaluated. Additionally or alternatively, BIAcore analysis can be used to assess the ability of the antibodies to cross-compete. The ability of a test antibody to inhibit the binding of, for example, 25F7, 26H10, 25E3, 8B7, 11F2 and/or 17E5, to human LAG-3 demonstrates that the test antibody can compete with 25F7, 26H10, 25E3, 8B7, 11F2 and/or 17E5 for binding to human LAG-3 and thus binds to the same epitope on human LAG-3 as 25F7, 26H10, 25E3, 8B7, 11F2 and/or 17E5. In a preferred embodiment, the antibody that binds to the same epitope on human LAG-3 as 25E3, 25F7, 8B7, 26H10, 11F2 or 17E5 is a human monoclonal antibody. Such human monoclonal antibodies can be prepared and isolated as described in the Examples.

As discussed further in Example 3C, the binding of 25E3, 25F7 and 8B7 to human LAG-3 has been mapped to an "extra loop" region within the first extracellular domain of human LAG-3. The sequence of the extra loop region is set forth in SEQ ID NO: 79. Using a peptide scan experiment, the binding of 25E3 to the extra loop region has been mapped to the following amino acid sequence: PGHPLAPG (SEQ ID NO: 76), whereas the binding of 25F7 to the extra loop region has been mapped to the following amino acid sequence: HPAAPSSW (SEQ ID NO: 77) and the binding of 8B7 to the extra loop region has been mapped to the following amino acid sequence: PAAPSSWG (SEQ ID NO: 78). Accordingly, in a preferred embodiment, the invention provides an anti-LAG-3 antibody that binds an epitope of human LAG-3 comprising the amino acid sequence PGH-PLAPG (SEQ ID NO: 76). In another preferred embodiment, the invention provides an anti-LAG-3 antibody that binds an epitope of human LAG-3 comprising the amino acid sequence HPAAPSSW (SEQ ID NO: 77) or PAAPSSWG (SEQ ID NO: 78).

Engineered and Modified Antibodies

An antibody of the invention further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al. (1998) *Nature* 332:323-327; Jones et al. (1986) *Nature* 321:522-525; Queen et al. (1989) *Proc. Natl. Acad. See. U.S.A.* 86:10029-10033; U.S. Pat. Nos. 5,225, 539; 5,530,101; 5,585,089; 5,693,762 and 6,180,370.)

Accordingly, another embodiment of the invention pertains to an isolated monoclonal antibody, or antigen binding portion thereof, comprising a heavy chain variable region comprising CDR1, CDR2, and CDR3 sequences comprising an amino acid sequence selected from the group consisting of SEQ ID NOs: 1-6, SEQ ID NOs: 7-12, and SEQ ID NOs: 13-14, GGY and 16-18, respectively, and a light chain variable region comprising CDR1, CDR2, and CDR3 sequences comprising an amino acid sequence selected from the group consisting of SEQ ID NOs: 19-24, SEQ ID NOs: 25-30, and SEQ ID NOs: 31-36, respectively. Thus, such antibodies contain the $V_H$ and $V_L$ CDR sequences of monoclonal antibodies 25F7, 26H10, 25E3, 8B7, 11F2 or 17E5 can contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al. (1991), cited supra; Tomlinson et al. (1992) "The Repertoire of Human Germline $V_H$ Sequences Reveals about Fifty Groups of $V_H$ Segments with Different Hypervariable Loops" *J. Mol. Biol.* 227:776-798; and Cox et al. (1994) "A Directory of Human Germ-line $V_H$ Segments Reveals a Strong Bias in their Usage" *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG 0010109, NT_024637 & BC070333), 3-33 (NG 0010109 & NT_024637) and 3-7 (NG 0010109 & NT_024637). As another example, the following heavy chain germline sequences found in the HCo12 HuMAb mouse are available in the accompanying Genbank Accession Nos.: 1-69 (NG_0010109, NT_024637 & BC070333), 5-51 (NG_0010109 & NT_024637), 4-34 (NG_0010109 & NT_024637), 3-30.3 (CAJ556644) & 3-23 (AJ406678).

Antibody protein sequences are compared against a compiled protein sequence database using one of the sequence similarity searching methods called the Gapped BLAST (Altschul et al. (1997), supra), which is well known to those skilled in the art.

Preferred framework sequences for use in the antibodies of the invention are those that are structurally similar to the framework sequences used by selected antibodies of the invention, e.g., similar to the $V_H$ 3-20 (SEQ ID NO: 69), $V_H$ 4-34 (SEQ ID NO: 61), $V_H$ 3-33 (SEQ ID NO: 65) or $V_H$ 1-24 (SEQ ID NO: 73) framework sequences and/or the $V_K$ L18 (SEQ ID NO: 71), $V_K$ L6 (SEQ ID NO: 63) or $V_K$ A27 (SEQ ID NO: 67) framework sequences used by preferred monoclonal antibodies of the invention. The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180, 370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations can be amino acid substitutions, additions or deletions, but are preferably substitutions. Moreover, typically no more than one, two, three, four or five residues within a CDR region are altered.

Accordingly, in another embodiment, the instant disclosure provides isolated anti-LAG-3 monoclonal antibodies, or antigen binding portions thereof, comprising a heavy chain variable region comprising: (a) a $V_H$ CDR1 region comprising an amino acid sequence selected from the group consisting of SEQ ID NOs: 1-6, or an amino acid sequence having one, two, three, four or five amino acid substitutions, deletions or additions as compared to SEQ ID NOs: 1-6; (b) a $V_H$ CDR2 region comprising an amino acid sequence selected from the group consisting of SEQ ID NOs: 7-12, or an amino acid sequence having one, two, three, four or five amino acid substitutions, deletions or additions as compared to SEQ ID NOs: 7-12; (c) a $V_H$ CDR3 region comprising an amino acid sequence selected from the group consisting of SEQ ID NOs: 13-14, GGY and 16-18, or an amino acid sequence having one, two, three, four or five amino acid substitutions, deletions or additions as compared to SEQ ID NOs: 13-14, GGY and 16-18; (d) a $V_L$ CDR1 region comprising an amino acid sequence selected from the group consisting of SEQ ID NOs: 19-24, or an amino acid sequence having one, two, three, four or five amino acid substitutions, deletions or additions as compared to SEQ ID NOs: 19-24; (e) a $V_L$ CDR2 region comprising an amino acid sequence selected from the group consisting of SEQ ID NOs: 25-30, or an amino acid sequence having one, two, three, four or five amino acid substitutions, deletions or additions as compared to SEQ ID NOs: 25-30; and (f) a $V_L$ CDR3 region comprising an amino acid sequence selected from the group consisting of SEQ ID NOs: 31-36, or an amino acid sequence having one, two, three, four or five amino acid substitutions, deletions or additions as compared to SEQ ID NOs: 31-36.

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

For example, Table A shows regions where a framework region amino acid position (using Kabat numbering system) differs from the germline and how this position can be backmutated to the germline by the indicated substitutions:

TABLE A

Exemplary Backmutations

| Region | Framework Amino Acid Position (Kabat Numbering) | Backmutation |
|---|---|---|
| 25E3 $V_H$ | 72 | G72R |
| 25E3 $V_H$ | 95 | Y95H |
| 25E3 $V_H$ | 97 | T97A |
| 25E3 $V_H$ | 98 | T98R |
| 25F7 $V_H$ | 69 | L69I |
| 25F7 $V_H$ | 71 | L71V |
| 25F7 $V_H$ | 83 | R83S |
| 25F7 $V_H$ | 97 | F97R |
| 8B7 $V_H$ | 76 | K76N |
| 8B7 $V_H$ | 79 | A79S |
| 8B7 $V_H$ | 83 | N83S |
| 8B7 $V_H$ | 112 | P112Q |
| 11F2 $V_H$ | 3 | D3A |
| 17E5 $V_H$ | 3 | H3Q |
| 8B7 $V_H$ | 59 | C59Y |
| 8B7 $V_H$ | 59 | C59S |

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition or alternative to modifications made within the framework or CDR regions, antibodies of the invention can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention can be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In a preferred embodiment, the antibody is an IgG4 isotype antibody comprising a Serine to Proline mutation at a position corresponding to position 228 (S228P; EU index) in the hinge region of the heavy chain constant region. This mutation has been reported to abolish the heterogeneity of inter-heavy chain disulfide bridges in the hinge region (Angal et al. supra; position 241 is based on the Kabat numbering system). For example, in various embodiments, an anti-LAG-3 antibody of the invention can comprise the heavy chain variable region of 25F7 (SEQ ID NO: 37) or 26H10 (SEQ ID NO: 38) linked to a human IgG4 constant region in which the Serine at a position corresponding to position 241 as described in Angal et al., supra, has been mutated to Proline. Thus, for the 25F7 and 26H10 heavy chain variable regions linked to a human IgG4 constant region, this mutation corresponds to an S228P mutation by the EU index.

In one embodiment, the hinge region of CH1 is modified such that the number of cysteine residues in the hinge region is altered, e.g., increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In another embodiment, the antibody is modified to increase its biological half life. Various approaches are possible. For example, one or more of the following mutations can be introduced: T252L, T254S, T256F, as described in U.S. Pat. No. 6,277,375. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551.

In another example, one or more amino acid residues within amino acid positions 231 and 239 are altered to thereby alter the ability of the antibody to fix complement. This approach is described further in PCT Publication WO 94/29351.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described (see Shields et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (a (1,6)-fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 and Yamane-Ohnuki et al. (2004) *Biotechnol Bioeng* 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al. (2002) *J. Biol. Chem.* 277:26733-26740). Antibodies with a modified glycosylation profile can also be produced in chicken eggs, as described in PCT Publication WO 06/089231. Alternatively, antibodies with a modified glycosylation profile can be produced in plant cells, such as *Lemna*. Methods for production of antibodies in a plant system are disclosed in the U.S. patent application Ser. No. 60/836,998, filed on Aug. 11, 2006. PCT Publication WO 99/54342 describes cell lines engineered to express glycoprotein-modifying glycosyl transferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody can be cleaved off using a fucosidase enzyme; e.g., the fucosidase α-L-fucosidase removes fucosyl residues from antibodies (Tarentino et al. (1975) *Biochem.* 14:5516-23).

Another modification of the antibodies herein that is contemplated by this disclosure is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, e.g., EP 0 154 316 and EP 0 401 384.

Antibody Physical Properties

Antibodies of this disclosure can be characterized by their various physical properties, to detect and/or differentiate different classes thereof.

Antibodies of the present disclosure can contain one or more glycosylation sites in either the light or heavy chain variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al. (2000) *Mol Immunol* 37:697-706). Glycosylation has been known to occur at motifs containing an N-X-S/T sequence. In some instances, it is preferred to have an anti-LAG-3 antibody that does not contain variable region glycosylation. This can be achieved either by selecting antibodies that do not contain the glycosylation motif in the variable region or by mutating residues within the glycosylation region.

In a preferred embodiment, the antibodies of the present disclosure do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-LAG-3 antibody that contains a pI value that falls in the normal range. This can be achieved either by selecting antibodies with a pI in the normal range or by mutating charged surface residues.

Each antibody will have a characteristic melting temperature, with a higher melting temperature indicating greater overall stability in vivo (Krishnamurthy R and Manning M C (2002) *Curr Pharm Biotechnol* 3:361-71). Generally, it is preferred that the TM1 (the temperature of initial unfolding) be greater than 60° C., preferably greater than 65° C., even more preferably greater than 70° C. The melting point of an antibody can be measured using differential scanning calorimetry (Chen et al (2003) *Pharm Res* 20:1952-60; Ghirlando et al (1999) *Immunol Lett* 68:47-52) or circular dichroism (Murray et al. (2002) *J. Chromatogr Sci* 40:343-9).

In a preferred embodiment, antibodies are selected that do not degrade rapidly. Degradation of an antibody can be measured using capillary electrophoresis (CE) and MALDI-MS (Alexander A J and Hughes D E (1995) *Anal Chem* 67:3626-32).

In another preferred embodiment, antibodies are selected that have minimal aggregation effects, which can lead to the triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation can be measured by several techniques, including size-exclusion column (SEC), high performance liquid chromatography (HPLC), and light scattering.

Methods of Engineering Antibodies

As discussed above, the anti-LAG-3 antibodies having $V_H$ and $V_L$ sequences disclosed herein can be used to create new anti-LAG-3 antibodies by modifying the $V_H$ and/or $V_L$ sequences, or the constant region(s) attached thereto. Thus, in another aspect of the invention, the structural features of an anti-LAG-3 antibody of the invention, e.g. 25F7, 26H10, 25E3, 8B7, 11F2 or 17E5, are used to create structurally related anti-LAG-3 antibodies that retain at least one functional property of the antibodies of the invention, such as binding to human LAG-3. For example, one or more CDR regions of 25F7, 26H10, 25E3, 8B7, 11F2 or 17E5, or mutations thereof, can be combined recombinantly with known framework regions and/or other CDRs to create additional, recombinantly-engineered, anti-LAG-3 antibodies of the invention, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, this disclosure provides a method for preparing an anti-LAG-3 antibody comprising:

(a) providing: (i) a heavy chain variable region antibody sequence comprising a CDR1 sequence selected from the group consisting of SEQ ID NOs: 1-6, a CDR2 sequence selected from the group consisting of SEQ ID NOs: 7-12, and/or a CDR3 sequence selected from the group consisting of SEQ ID NOs: 13-14, GGY and 16-18; and/or (ii) a light chain variable region antibody sequence comprising a CDR1 sequence selected from the group consisting of SEQ ID NOs: 19-24, a CDR2 sequence selected from the group consisting of SEQ ID NOs: 25-30, and/or a CDR3 sequence selected from the group consisting of SEQ ID NOs: 31-36;

(b) altering at least one amino acid residue within the heavy chain variable region antibody sequence and/or the light chain variable region antibody sequence to create at least one altered antibody sequence; and (c) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-LAG-3 antibodies described herein, which functional properties include, but are not limited to:

(i) high affinity binding to human LAG-3;
(ii) binding to monkey LAG-3;
(iii) lack of binding to mouse LAG-3
(iv) an ability to inhibit binding of LAG-3 to MHC Class II molecules; and/or
(v) an ability to stimulate an immune response (e.g., an antigen-specific T cell response).

The functional properties of the altered antibodies can be assessed using standard assays available in the art and/or described herein, such as those set forth in the Examples.

In certain embodiments of the methods of engineering antibodies of the invention, mutations can be introduced randomly or selectively along all or part of an anti-LAG-3 antibody coding sequence and the resulting modified anti-LAG-3 antibodies can be screened for binding activity and/or other functional properties as described herein. Mutational methods have been described in the art (see, e.g., PCT Publications WO 02/092780 and WO 03/074679).

Nucleic Acid Molecules Encoding Antibodies of the Invention

Another aspect of the invention pertains to nucleic acid molecules that encode the antibodies of the invention. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, Ausubel, et al., ed. (1987) Current Protocols in Molecular Biology, Greene Publishing and Wiley Interscience, New York. A nucleic acid of the invention can be, e.g., DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the invention are those encoding the $V_H$ and $V_L$ sequences of the 25E3, 25F7, 8B7, 26H10, 11F2 and 17E5 monoclonal antibodies. DNA sequences encoding the $V_H$ sequences of 25E3, 25F7, 8B7, 26H10, 11F2 and 17E5 are shown in SEQ ID NOs: 49-54, respectively. DNA sequences encoding the $V_L$ sequences of 25E3, 25F7, 8B7, 26H10, 11F2 and 17E5 are shown in SEQ ID NOs: 55-60, respectively.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat et al. (1991), supra) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (see e.g., Kabat et al., supra) and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)$_3$, such that the $V_H$ and $V_L$ sequences can be expressed as a contiguous single-chain protein, with the $V_L$ and $V_H$ regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Production of Monoclonal Antibodies of the Invention

Monoclonal antibodies (mAbs) of the present disclosure can be produced using the well-known somatic cell hybridization (hybridoma) technique of Kohler and Milstein (1975) Nature 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

In a preferred embodiment, the antibodies of the invention are human monoclonal antibodies. Such human monoclonal antibodies directed against human LAG-3 can be generated using transgenic or transchromosomic mice carrying parts of the human immune system rather than the mouse system. These transgenic and transchromosomic mice include mice referred to herein as the HuMAb Mouse® and KM Mouse®, respectively, and are collectively referred to herein as "human Ig mice."

The HuMAb Mouse® (Medarex®, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg et al. (1994), supra; reviewed in Lonberg (1994) Handbook of Experimental Pharmacology 113: 49-101; Lonberg, N. and Huszar, D. (1995) Intern. Rev. Immunol. 13: 65-93, and Harding and Lonberg (1995) Ann. N.Y. Acad. Sci. 764:536-546). Preparation and use of the HuMAb Mouse®, and the genomic modifications carried by such mice, is further described in Taylor et al. (1992) Nucleic Acids Research 20:6287-6295; Chen et al. (1993) International Immunology 5: 647-656; Tuaillon et al. (1993) Proc. Natl. Acad. Sci. USA 90:3720-3724; Choi et al. (1993) Nature Genetics 4:117-123; Chen et al. (1993) EMBO J. 12: 821-830; Tuaillon et al. (1994) J. Immunol. 152:2912-2920; Taylor et al. (1994) International Immunology 6: 579-591; and Fishwild et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807; PCT Publication Nos. WO 92/03918; WO 93/12227; WO 94/25585; WO 97/13852; WO 98/24884; WO 99/45962 and WO 01/14424, the contents of which are incorporated herein by reference in their entirety.

In another embodiment, human antibodies of the invention can be raised using a mouse that carries human immunoglobulin sequences on transgenes and transchomosomes, such as a mouse that carries a human heavy chain transgene and a human light chain transchromosome. This mouse is referred to herein as a "KM Mouse®," and is described in detail in PCT Publication WO 02/43478. A modified form of this mouse, which further comprises a homozygous disruption of the endogenous FcγRIIB receptor gene, is also described in PCT Publication WO 02/43478 and referred to herein as a "KM/FCGR2D Mouse®." In addition, mice with either the HCo7 or HCo12 heavy chain transgenes or both can be used.

Additional transgenic animal embodiments include the Xenomouse (Abgenix, Inc., U.S. Pat. Nos. 5,939,598; 6,075,181; 6,114,598; 6,150,584 and 6,162,963). Further embodiments include "TC mice" (Tomizuka et al. (2000) Proc. Natl. Acad. Sci. USA 97:722-727) and cows carrying human heavy and light chain transchromosomes (Kuroiwa et al. (2002) *Nature Biotechnology* 20:889-894; PCT Publication WO 02/092812). The contents of these patents and publications are specifically incorporated herein by reference in their entirety.

In one embodiment, human monoclonal antibodies of the invention are prepared using phage display methods for screening libraries of human immunoglobulin genes. See, e.g. U.S. Pat. Nos. 5,223,409; 5,403,484; 5,571,698; 5,427,908; 5,580,717; 5,969,108; 6,172,197; 5,885,793; 6,521,404; 6,544,731; 6,555,313; 6,582,915; and 6,593,081, the contents of which are incorporated herein by reference in their entirety.

Human monoclonal antibodies of the invention can also be prepared using SCID mice into which human immune cells have been reconstituted such that a human antibody response can be generated upon immunization. See, e.g., U.S. Pat. Nos. 5,476,996 and 5,698,767, the contents of which are incorporated herein by reference in their entirety.

In another embodiment, human anti-LAG-3 antibodies are prepared using phage display where the phages comprise nucleic acids encoding antibodies generated in transgenic animals previously immunized with LAG-3. In a preferred embodiment, the transgenic animal is a HuMab, KM, or Kirin mouse. See, e.g. U.S. Pat. No. 6,794,132, the contents of which are incorporated herein by reference in its entirety.

Immunization of Human Ig Mice

In one embodiment of the invention, human Ig mice are immunized with a purified or enriched preparation of a LAG-3 antigen, recombinant LAG-3 protein, or cells expressing a LAG-3 protein. See, e.g., Lonberg et al. (1994), supra; Fishwild et al. (1996), supra; PCT Publications WO 98/24884 or WO 01/14424, the contents of which are incorporated herein by reference in their entirety. In a preferred embodiment, 6-16 week old mice are immunized with 5-50 µg of LAG-3 protein. Alternatively, a portion of LAG-3 fused to a non-LAG-3 polypeptide is used.

In one embodiment, the transgenic mice are immunized intraperitoneally (IP) or intravenously (IV) with LAG-3 antigen in complete Freund's adjuvant, followed by subsequent IP or IV immunizations with antigen in incomplete Freund's adjuvant. In other embodiments, adjuvants other than Freund's or whole cells in the absence of adjuvant are used. The plasma can be screened by ELISA and cells from mice with sufficient titers of anti-LAG-3 human immunoglobulin can be used for fusions.

Generation of Hybridomas Producing Human Monoclonal Antibodies of the Invention

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. Generation of hybridomas is well-known in the art. See, e.g., Harlow and Lane (1988) *Antibodies, A Laboratory Manual*, Cold Spring Harbor Publications, New York.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) *Science* 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody chain genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al. (1988) *Mol. Cell. Biol.* 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the invention can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies of the invention can be tested for binding to human LAG-3 by, for example, standard ELISA. Anti-LAG-3 human IgGs can be further tested for reactivity with a LAG-3 antigen by Western blotting. The binding specificity of an antibody of the invention can also be determined by monitoring binding of the antibody to cells expressing a LAG-3 protein, e.g., flow cytometry. These methods are known in the art. See, e.g., Harlow and Lane (1988), cited supra.

Immunoconjugates

Antibodies of this invention can be conjugated to a therapeutic agent to form an immunoconjugate such as an antibody-drug conjugate (ADC). Suitable therapeutic agents include antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val (SEQ ID NO:15), Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038658; WO 07/051081; WO 07/059404; WO 08/083312; and WO 08/103693; U.S. Patent Publications 20060024317; 20060004081; and 20060247295; the disclosures of which are incorporated herein by reference.

Bispecific Molecules

In another aspect, the present disclosure features bispecific molecules comprising an anti-LAG-3 antibody linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities. In a preferred embodiment, the bispecific molecule comprises a first binding specificity for LAG-3 and a second binding specificity for a triggering molecule that recruits cytotoxic effector cells that can kill a LAG-3 expressing target cell. Examples of suitable triggering molecules are CD64, CD89, CD16, and CD3. See, e.g., Kufer et al., *TRENDS in Biotechnology*, 22 (5), 238-244 (2004).

In an embodiment, a bispecific molecule has, in addition to an anti-Fc binding specificity and an anti-LAG-3 binding specificity, a third specificity. The third specificity can be for an anti-enhancement factor (EF), e.g., a molecule that binds to a surface protein involved in cytotoxic activity and thereby increases the immune response against the target cell. For example, the anti-enhancement factor can bind a cytotoxic T-cell (e.g. via CD2, CD3, CD8, CD28, CD4, CD40, or ICAM-1) or other immune cell, resulting in an increased immune response against the target cell.

Bispecific molecules can come in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv)$_2$ construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al, cited supra; Cao and Suresh, Bioconjugate Chemistry, 9 (6), 635-644 (1998); and van Spriel et al., *Immunology Today*, 21 (8), 391-397 (2000), and the references cited therein.

Pharmaceutical Compositions

In another aspect, the present disclosure provides a pharmaceutical composition comprising an antibody of the present disclosure formulated together with a pharmaceutically acceptable carrier. It may optionally contain one or more additional pharmaceutically active ingredients, such as another antibody or a drug. The pharmaceutical compositions of the invention also can be administered in a combination therapy with, for example, another immunostimulatory agent, anti-cancer agent, an anti-viral agent, or a vaccine, such that the anti-LAG-3 antibody enhances the immune response against the vaccine.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: *The Science and Practice of Pharmacy*, 20th Ed. (Lippincott Williams & Wilkins 2003), the disclosure of which is incorporated herein by reference.

Preferably, a pharmaceutical composition is suitable for intravenous, intramuscular, subcutaneous, parenteral, spinal or epidermal administration (e.g., by injection or infusion). Depending on the route of administration, the active compound can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, e.g., intranasally, orally, vaginally, rectally, sublingually or topically.

The pharmaceutical compounds of the invention can be in the form of pharmaceutically acceptable salts. A "pharmaceutically acceptable salt" refers to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Alternatively, antibody can be administered as a sustained release formulation, in which case less frequent administration is required.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-LAG-3 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 μg/ml and in some methods about 25-300 μg/ml.

A "therapeutically effective dosage" of an anti-LAG-3 antibody of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human or can be another mammal.

The pharmaceutical composition can be a controlled release formulation, including implants, transdermal patches, and microencapsulated delivery systems.

Biodegradable, biocompatible polymers can be used, such as ethylene vinyl acetate, polyanhydrides, polyglycolic acid, collagen, polyorthoesters, and polylactic acid. See, e.g., *Sustained and Controlled Release Drug Delivery Systems*, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparati (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the human monoclonal antibodies of the invention can be formulated to ensure proper distribution in vivo. For example, to ensure that the therapeutic compounds of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al. (1995) *FEBS Lett.* 357:140; M. Owais et al. (1995) *Antimicrob. Agents Chemother.* 39:180; Briscoe et al. (1995) *Am. J. Physiol.* 1233:134; Schreier et al. (1994) *J. Biol. Chem.* 269:9090; Keinanen and Laukkanen (1994) *FEBS Lett.* 346:123; and Killion and Fidler (1994) *Immunomethods* 4:273.

Uses and Methods of the Invention

The antibodies, antibody compositions and methods of the present invention have numerous in vitro and in vivo utilities involving, for example, detection of LAG-3 or enhancement of immune response by blockade of LAG-3. In a preferred embodiment, the antibodies of the present invention are human antibodies. For example, these molecules can be administered to cells in culture, in vitro or ex vivo, or to human subjects, e.g., in vivo, to enhance immunity in a variety of situations. Accordingly, in one aspect, the invention provides a method of modifying an immune response in a subject comprising administering to the subject the antibody, or antigen-binding portion thereof, of the invention such that the immune response in the subject is modified. Preferably, the response is enhanced, stimulated or up-regulated.

Preferred subjects include human patients in need of enhancement of an immune response. The methods are particularly suitable for treating human patients having a disorder that can be treated by augmenting an immune response (e.g., the T-cell mediated immune response). In a particular embodiment, the methods are particularly suitable for treatment of cancer in vivo. To achieve antigen-specific enhancement of immunity, the anti-LAG-3 antibodies can be administered together with an antigen of interest or the antigen may already be present in the subject to be treated (e.g., a tumor-bearing or virus-bearing subject). When antibodies to LAG-3 are administered together with another agent, the two can be administered in either order or simultaneously.

The invention further provides methods for detecting the presence of human LAG-3 antigen in a sample, or measuring the amount of human LAG-3 antigen, comprising contacting the sample, and a control sample, with a human monoclonal antibody, or an antigen binding portion thereof, which specifically binds to human LAG-3, under conditions that allow for formation of a complex between the antibody or portion thereof and human LAG-3. The formation of a complex is then detected, wherein a difference complex formation between the sample compared to the control sample is indicative the presence of human LAG-3 antigen in the sample. Moreover, the anti-LAG-3 antibodies of the invention can be used to purify human LAG-3 via immunoaffinity purification.

Given the ability of anti-LAG-3 antibodies of the invention to inhibit the binding of LAG-3 to MHC Class II molecules and to stimulate antigen-specific T cell responses, the invention also provides in vitro and in vivo methods of using the antibodies of the invention to stimulate, enhance or upregulate antigen-specific T cell responses. For example, the invention provides a method of stimulating an antigen-specific T cell response comprising contacting said T cell with the antibody of the invention such that an antigen-specific T cell response is stimulated. Any suitable indicator of an antigen-specific T cell response can be used to measure the antigen-specific T cell response.

Non-limiting examples of such suitable indicators include increased T cell proliferation in the presence of the antibody and/or increase cytokine production in the presence of the antibody. In a preferred embodiment, interleukin-2 production by the antigen-specific T cell is stimulated.

The invention also provides a method of stimulating an immune response (e.g., an antigen-specific T cell response) in a subject comprising administering an antibody of the invention to the subject such that an immune response (e.g., an antigen-specific T cell response) in the subject is stimulated. In a preferred embodiment, the subject is a tumor-bearing subject and an immune response against the tumor is stimulated. In another preferred embodiment, the subject is a virus-bearing subject and an immune response against the virus is stimulated.

In another aspect, the invention provides a method for inhibiting growth of tumor cells in a subject comprising administering to the subject an antibody of the invention such that growth of the tumor is inhibited in the subject. In yet another aspect, the invention provides a method of treating viral infection in a subject comprising administering to the subject an antibody of the invention such that the viral infection is treated in the subject.

These and other methods of the invention are discussed in further detail below.

Cancer

Blockade of LAG-3 by antibodies can enhance the immune response to cancerous cells in the patient. In one aspect, the present invention relates to treatment of a subject in vivo using an anti-LAG-3 antibody such that growth of cancerous tumors is inhibited. An anti-LAG-3 antibody can be used alone to inhibit the growth of cancerous tumors. Alternatively, an anti-LAG-3 antibody can be used in conjunction with other immunogenic agents, standard cancer treatments, or other antibodies, as described below.

Accordingly, in one embodiment, the invention provides a method of inhibiting growth of tumor cells in a subject, comprising administering to the subject a therapeutically effective amount of an anti-LAG-3 antibody, or antigen-binding portion thereof. Preferably, the antibody is a human anti-LAG-3 antibody (such as any of the human anti-human LAG-3 antibodies described herein). Additionally or alternatively, the antibody can be a chimeric or humanized anti-LAG-3 antibody.

Preferred cancers whose growth may be inhibited using the antibodies of the invention include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the invention includes refractory or recurrent malignancies whose growth may be inhibited using the antibodies of the invention.

Examples of other cancers that can be treated using the methods of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers, especially metastatic cancers that express PD-L1 (Iwai et al. (2005) Int. Immunol. 17:133-144).

Optionally, antibodies to LAG-3 can be combined with an immunogenic agent, such as cancerous cells, purified tumor antigens (including recombinant proteins, peptides, and carbohydrate molecules), cells, and cells transfected with genes encoding immune stimulating cytokines (He et al (2004) J. Immunol. 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

In humans, some tumors have been shown to be immunogenic such as melanomas. By raising the threshold of T cell activation by LAG-3 blockade, the tumor responses in the host can be activated.

LAG-3 blockade is likely to be more effective when combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita et al. (eds.), 1997, Cancer: Principles and Practice of Oncology, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci U.S.A.* 90: 3539-43).

The study of gene expression and large scale gene expression patterns in various tumors has led to the definition of so called tumor specific antigens (Rosenberg, S A (1999) *Immunity* 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. LAG-3 blockade can be used in conjunction with a collection of recombinant proteins and/or peptides expressed in a tumor in order to generate an immune response to these proteins. These proteins are normally viewed by the immune system as self antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) *Science* 266: 2011-2013). (These somatic tissues may be protected from immune attack by various means). Tumor antigen can also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines can include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which can be used in conjunction with LAG-3 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) *Science* 269:1585-1588; Tamura et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle et al. (1998) *Nature Medicine* 4: 328-332). DCs can also be transduced by genetic means to express these tumor antigens as well. DCs have also been fused directly to tumor cells for the purposes of immunization (Kugler et al. (2000) *Nature Medicine* 6:332-336). As a method of vaccination, DC immunization can be effectively combined with LAG-3 blockade to activate more potent anti-tumor responses.

LAG-3 blockade can also be combined with standard cancer treatments. LAG-3 blockade can be effectively combined with chemotherapeutic regimes. In these instances, it may be possible to reduce the dose of chemotherapeutic reagent administered (Mokyr et al. (1998) *Cancer Research* 58: 5301-5304). An example of such a combination is an anti-LAG-3 antibody in combination with decarbazine for the treatment of melanoma. Another example of such a combination is an anti-LAG-3 antibody in combination with interleukin-2 (IL-2) for the treatment of melanoma. The scientific rationale behind the combined use of LAG-3 blockade and chemotherapy is that cell death, that is a consequence of the cytotoxic action of most chemotherapeutic compounds, should result in increased levels of tumor antigen in the antigen presentation pathway. Other combination therapies that may result in synergy with LAG-3 blockade through cell death are radiation, surgery, and hormone deprivation. Each of these protocols creates a source of tumor antigen in the host. Angiogenesis inhibitors can also be combined with LAG-3 blockade. Inhibition of angiogenesis leads to tumor cell death which may feed tumor antigen into host antigen presentation pathways.

LAG-3 blocking antibodies can also be used in combination with bispecific antibodies that target Fcα or Fcγ receptor-expressing effectors cells to tumor cells (see, e.g., U.S. Pat. Nos. 5,922,845 and 5,837,243). Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would be augmented by the use of LAG-3 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). Antibodies to each of these entities can be used in combination with anti-LAG-3 to counteract the effects of the immunosuppressive agent and favor tumor immune responses by the host.

Other antibodies which activate host immune responsiveness can be used in combination with anti-LAG-3. These include molecules on the surface of dendritic cells which activate DC function and antigen presentation. Anti-CD40 antibodies are able to substitute effectively for T cell helper activity (Ridge et al. (1998) *Nature* 393: 474-478) and can be used in conjunction with LAG-3 antibodies (Ito et al. (2000) *Immunobiology* 201 (5) 527-40). Activating antibodies to T cell costimulatory molecules such as CTLA-4 (e.g., U.S. Pat. No. 5,811,097), OX-40 (Weinberg et al. (2000) *Immunol* 164: 2160-2169), 4-1BB (Melero et al. (1997) *Nature Medicine* 3: 682-685 (1997), and ICOS (Hutloff et al. (1999) *Nature* 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. LAG-3 blockade can be used to increase the effectiveness of the donor engrafted tumor specific T cells.

There are also several experimental treatment protocols that involve ex vivo activation and expansion of antigen specific T cells and adoptive transfer of these cells into recipients in order to stimulate antigen-specific T cells against tumor (Greenberg & Riddell (1999) *Science* 285: 546-51). These methods can also be used to activate T cell responses to infectious agents such as CMV. Ex vivo activation in the presence of anti-LAG-3 antibodies can increase the frequency and activity of the adoptively transferred T cells.

Infectious Diseases

Other methods of the invention are used to treat patients that have been exposed to particular toxins or pathogens. Accordingly, another aspect of the invention provides a method of treating an infectious disease in a subject comprising administering to the subject an anti-LAG-3 antibody, or antigen-binding portion thereof, such that the subject is treated for the infectious disease. Preferably, the antibody is a human anti-human LAG-3 antibody (such as any of the human anti-LAG-3 antibodies described herein). Additionally or alternatively, the antibody can be a chimeric or humanized antibody.

Similar to its application to tumors as discussed above, antibody mediated LAG-3 blockade can be used alone, or as an adjuvant, in combination with vaccines, to stimulate the immune response to pathogens, toxins, and self-antigens. Examples of pathogens for which this therapeutic approach can be particularly useful, include pathogens for which there is currently no effective vaccine, or pathogens for which conventional vaccines are less than completely effective. These include, but are not limited to HIV, Hepatitis (A, B, & C), Influenza, Herpes, Giardia, Malaria, Leishmania, *Staphylococcus aureus, Pseudomonas aeruginosa*. LAG-3 blockade is particularly useful against established infections by agents such as HIV that present altered antigens over the course of the infections. These novel epitopes are recognized as foreign at the time of anti-human LAG-3 administration, thus provoking a strong T cell response that is not dampened by negative signals through LAG-3.

Some examples of pathogenic viruses causing infections treatable by methods of the invention include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the invention include chlamydia, rickettsial bacteria, mycobacteria, staphylococci, streptococci, pneumonococci, meningococci and gonococci, klebsiella, proteus, serratia, pseudomonas, legionella, diphtheria, salmonella, bacilli, cholera, tetanus, botulism, anthrax, plague, leptospirosis, and Lymes disease bacteria.

Some examples of pathogenic fungi causing infections treatable by methods of the invention include *Candida* (*albicans, krusei, glabrata, tropicalis*, etc.), *Cryptococcus neoformans, Aspergillus* (*fumigatus, niger*, etc.), Genus Mucorales (*mucor, absidia, rhizopus*), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the invention include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii, Nippostrongylus brasiliensis*.

In all of the above methods, LAG-3 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) *Proc. Natl. Acad. Sci. USA* 90:6444-6448; Poljak (1994) *Structure* 2:1121-1123).

Autoimmune Reactions

Anti-LAG-3 antibodies may provoke and amplify autoimmune responses. Indeed, induction of anti-tumor responses using tumor cell and peptide vaccines reveals that many anti-tumor responses involve anti-self reactivities (van Elsas et al. (2001) *J. Exp. Med.* 194:481-489; Overwijk, et al. (1999) *Proc. Natl. Acad. Sci. U.S.A.* 96: 2982-2987; Hurwitz, (2000) supra; Rosenberg & White (1996) *J. Immunother Emphasis Tumor Immunol* 19 (1): 81-4). Therefore, it is possible to consider using anti-LAG-3 blockade in conjunction with various self proteins in order to devise vaccination protocols to efficiently generate immune responses against these self proteins for disease treatment. For example, Alzheimer's disease involves inappropriate accumulation of Aβ peptide in amyloid deposits in the brain; antibody responses against amyloid are able to clear these amyloid deposits (Schenk et al., (1999) *Nature* 400: 173-177).

Other self proteins can also be used as targets such as IgE for the treatment of allergy and asthma, and TNFα for rheumatoid arthritis. Finally, antibody responses to various hormones may be induced by the use of anti-LAG-3 antibody. Neutralizing antibody responses to reproductive hormones can be used for contraception. Neutralizing antibody response to hormones and other soluble factors that are required for the growth of particular tumors can also be considered as possible vaccination targets.

Analogous methods as described above for the use of anti-LAG-3 antibody can be used for induction of therapeutic autoimmune responses to treat patients having an inappropriate accumulation of other self-antigens, such as amyloid deposits, including AR in Alzheimer's disease, cytokines such as TNFα, and IgE.

Vaccines

Anti-LAG-3 antibodies can be used to stimulate antigen-specific immune responses by coadministration of an anti-LAG-3 antibody with an antigen of interest (e.g., a vaccine). Accordingly, in another aspect the invention provides a method of enhancing an immune response to an antigen in a subject, comprising administering to the subject: (i) the antigen; and (ii) an anti-LAG-3 antibody, or antigen-binding portion thereof, such that an immune response to the antigen in the subject is enhanced. Preferably, the antibody is a human anti-human LAG-3 antibody (such as any of the human anti-LAG-3 antibodies described herein). Additionally or alternatively, the antibody can be a chimeric or humanized antibody. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

Suitable routes of administering the antibody compositions (e.g., human monoclonal antibodies, multispecific and bispecific molecules and immunoconjugates) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-LAG-3 antibodies of the invention can be co-administered with one or other more therapeutic agents, e.g., a cytotoxic agent, a radiotoxic agent or an immunosuppressive agent. The antibody can be linked to the agent (as an immuno-complex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, dacarbazine and cyclophosphamide hydroxyurea which, by themselves, are only effective at levels which are toxic or subtoxic to a patient. Cisplatin is intravenously administered as a 100 mg/ml dose once every four weeks and adriamycin is intravenously administered as a 60-75 mg/ml dose once every 21 days. Co-administration of the human anti-LAG-3 antibodies, or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Also within the scope of the present invention are kits comprising the antibody compositions of the invention (e.g., human antibodies, bispecific or multispecific molecules, or immunoconjugates) and instructions for use. The kit can further contain at least one additional reagent, or one or more additional human antibodies of the invention (e.g., a human antibody having a complementary activity which binds to an epitope in LAG-3 antigen distinct from the first human antibody). Kits typically include a label indicating the intended use of the contents of the kit. The term label includes any writing, or recorded material supplied on or with the kit, or which otherwise accompanies the kit.

Combination Therapy

In another aspect, the invention provides methods of combination therapy in which an anti-LAG-3 antibody is coadministered with one or more additional antibodies that are effective in stimulating immune responses to thereby further enhance, stimulate or upregulate immune responses in a subject. For example, the invention provides a method for stimulating an immune response in a subject comprising administering to the subject an anti-LAG-3 antibody and one or more additional immunostimulatory antibodies, such as an anti-PD-1 antibody, an anti-PD-L1 antibody and/or an anti-CTLA-4 antibody, such that an immune response is stimulated in the subject, for example to inhibit tumor growth or to stimulate an anti-viral response. In one embodiment, the subject is administered an anti-LAG-3 antibody and an anti-PD-1 antibody. In another embodiment, the subject is administered an anti-LAG-3 antibody and an anti-PD-L1 antibody. In yet another embodiment, the subject is administered an anti-LAG-3 antibody and an anti-CTLA-4 antibody. In one embodiment, the anti-LAG-3 antibody is a human antibody, such as an antibody of the disclosure. Alternatively, the anti-LAG-3 antibody can be, for example, a chimeric or humanized antibody (e.g., prepared from a mouse anti-LAG-3 mAb). In another embodiment, the at least one additional immunostimulatory antibody (e.g., anti-PD-1, anti-PD-L1 and/or anti-CTLA-4 antibody) is a human antibody. Alternatively, the at least one additional immunostimulatory antibody can be, for example, a chimeric or humanized antibody (e.g., prepared from a mouse anti-PD-1, anti-PD-L1 and/or anti-CTLA-4 antibody).

In one embodiment, the present invention provides a method for treating a hyperproliferative disease (e.g., cancer), comprising administering a LAG-3 antibody and a CTLA-4 antibody to a subject. In further embodiments, the anti-LAG-3 antibody is administered at a subtherapeutic dose, the anti-CTLA-4 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering an anti-LAG-3 antibody and a subtherapeutic dose of anti-CTLA-4 antibody to a subject. In certain embodiments, the subject is human. In certain embodiments, the anti-CTLA-4 antibody is human sequence monoclonal antibody 10D1 (described in PCT Publication WO 01/14424) and the anti-LAG-3 antibody is human sequence monoclonal antibody, such as 25F7, 26H10, 25E3, 8B7, 11F2 or 17E5 described herein. Other anti-CTLA-4 antibodies encompassed by the methods of the present invention include, for example, those disclosed in: WO 98/42752; WO 00/37504; U.S. Pat. No. 6,207,156; Hurwitz et al. (1998) *Proc. Natl. Acad. Sci. USA* 95(17):10067-10071; Camacho et al. (2004) *J. Clin. Oncology* 22(145): Abstract No. 2505 (antibody CP-675206); and Mokyr et al. (1998) *Cancer Res.* 58:5301-5304. In certain embodiments, the anti-CTLA-4 antibody binds to human CTLA-4 with a $K_D$ of $5\times10^{-8}$ M or less, binds to human CTLA-4 with a $K_D$ of $1\times10^{-8}$ M or less, binds to human CTLA-4 with a $K_D$ of $5\times10^{-9}$ M or less, or binds to human CTLA-4 with a $K_D$ of between $1\times10^{-8}$ M and $1\times10^{-10}$ M or less.

In one embodiment, the present invention provides a method for treating a hyperproliferative disease (e.g., cancer), comprising administering a LAG-3 antibody and a PD-1 antibody to a subject. In further embodiments, the anti-LAG-3 antibody is administered at a subtherapeutic dose, the anti-PD-1 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering an anti-LAG-3 antibody and a subtherapeutic dose of anti-PD-1 antibody to a subject. In certain embodiments, the subject is human. In certain embodiments, the anti-PD-1 antibody is a human sequence monoclonal antibody and the anti-LAG-3 antibody is human sequence monoclonal antibody, such as 25F7, 26H10, 25E3, 8B7, 11F2 or 17E5 described herein. Examples of human sequence anti-PD-1 antibodies include 17D8, 2D3, 4H1, 5C4 and 4A11, which are described in PCT Publication WO 06/121168. In certain embodiments, the anti-PD-1 antibody binds to human PD-1 with a $K_D$ of $5 \times 10^{-8}$ M or less, binds to human PD-1 with a $K_D$ of $1 \times 10^{-8}$ M or less, binds to human PD-1 with a $K_D$ of $5 \times 10^{-9}$ M or less, or binds to human PD-1 with a $K_D$ of between $1 \times 10^{-8}$ M and $1 \times 10^{-10}$ M or less.

In one embodiment, the present invention provides a method for treating a hyperproliferative disease (e.g., cancer), comprising administering a LAG-3 antibody and a PD-L1 antibody to a subject. In further embodiments, the anti-LAG-3 antibody is administered at a subtherapeutic dose, the anti-PD-L1 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering an anti-LAG-3 antibody and a subtherapeutic dose of anti-PD-L1 antibody to a subject. In certain embodiments, the subject is human. In certain embodiments, the anti-PD-L1 antibody is a human sequence monoclonal antibody and the anti-LAG-3 antibody is human sequence monoclonal antibody, such as 25F7, 26H10, 25E3, 8B7, 11F2 or 17E5 described herein. Examples of human sequence anti-PD-L1 antibodies include 3G10, 12A4, 10A5, 5F8, 10H10, 1B12, 7H1, 11E6, 12B7 and 13G4, which are described in PCT Publication WO 07/005874. In certain embodiments, the anti-PD-L1 antibody binds to human PD-L1 with a $K_D$ of $5 \times 10^{-8}$ M or less, binds to human PD-L1 with a $K_D$ of $1 \times 10^{-8}$ M or less, binds to human PD-L1 with a $K_D$ of $5 \times 10^{-9}$ M or less, or binds to human PD-L1 with a $K_D$ of between $1 \times 10^{-8}$ M and $1 \times 10^{-10}$ M or less.

Blockade of LAG-3 and one or more second target antigens such as CTLA-4 and/or PD-1 and/or PD-L1 by antibodies can enhance the immune response to cancerous cells in the patient. Cancers whose growth may be inhibited using the antibodies of the instant disclosure include cancers typically responsive to immunotherapy. Representative examples of cancers for treatment with the combination therapy of the instant disclosure include those cancers specifically listed above in the discussion of monotherapy with anti-LAG-3 antibodies.

In certain embodiments, the combination of therapeutic antibodies discussed herein can be administered concurrently as a single composition in a pharmaceutically acceptable carrier, or concurrently as separate compositions with each antibody in a pharmaceutically acceptable carrier. In another embodiment, the combination of therapeutic antibodies can be administered sequentially. For example, an anti-CTLA-4 antibody and an anti-LAG-3 antibody can be administered sequentially, such as anti-CTLA-4 antibody being administered first and anti-LAG-3 antibody second, or anti-LAG-3 antibody being administered first and anti-CTLA-4 antibody second. Additionally or alternatively, an anti-PD-1 antibody and an anti-LAG-3 antibody can be administered sequentially, such as anti-PD-1 antibody being administered first and anti-LAG-3 antibody second, or anti-LAG-3 antibody being administered first and anti-PD-1 antibody second. Additionally or alternatively, an anti-PD-L1 antibody and an anti-LAG-3 antibody can be administered sequentially, such as anti-PD-L1 antibody being administered first and anti-LAG-3 antibody second, or anti-LAG-3 antibody being administered first and anti-PD-L1 antibody second.

Furthermore, if more than one dose of the combination therapy is administered sequentially, the order of the sequential administration can be reversed or kept in the same order at each time point of administration, sequential administrations can be combined with concurrent administrations, or any combination thereof. For example, the first administration of a combination anti-CTLA-4 antibody and anti-LAG-3 antibody can be concurrent, the second administration can be sequential with anti-CTLA-4 first and anti-LAG-3 second, and the third administration can be sequential with anti-LAG-3 first and anti-CTLA-4 second, etc. Additionally or alternatively, the first administration of a combination anti-PD-1 antibody and anti-LAG-3 antibody can be concurrent, the second administration can be sequential with anti-PD-1 first and anti-LAG-3 second, and the third administration can be sequential with anti-LAG-3 first and anti-PD-1 second, etc. Additionally or alternatively, the first administration of a combination anti-PD-L1 antibody and anti-LAG-3 antibody can be concurrent, the second administration can be sequential with anti-PD-L1 first and anti-LAG-3 second, and the third administration can be sequential with anti-LAG-3 first and anti-PD-L1 second, etc. Another representative dosing scheme can involve a first administration that is sequential with anti-LAG-3 first and anti-CTLA-4 (and/or anti-PD-1 and/or anti-PD-L1) second, and subsequent administrations may be concurrent.

Optionally, the combination of anti-LAG-3 and one or more additional antibodies (e.g., anti-CTLA-4 and/or anti-PD-1 and/or anti-PD-L1 antibodies) can be further combined with an immunogenic agent, such as cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below). A combined LAG-3 and CTLA-4 and/or PD-1 and/or PD-L1 blockade can be further combined with a vaccination protocol, such as any of the vaccination protocols discussed in detail above with respect to monotherapy with anti-LAG-3 antibodies.

A combined LAG-3 and CTLA-4 and/or PD-1 and/or PD-L1 blockade can also be further combined with standard cancer treatments. For example, a combined LAG-3 and CTLA-4 and/or PD-1 and/or PD-L1 blockade can be effectively combined with chemotherapeutic regimes. In these instances, it is possible to reduce the dose of other chemotherapeutic reagent administered with the combination of the instant disclosure (Mokyr et al. (1998) *Cancer Research* 58: 5301-5304). An example of such a combination is a combination of anti-LAG-3 and anti-CTLA-4 antibodies and/or anti-PD-1 antibodies and/or anti-PD-L1 antibodies further in combination with decarbazine for the treatment of melanoma. Another example is a combination of anti-LAG-3 and anti-CTLA-4 antibodies and/or anti-PD-1 antibodies and/or anti-PD-L1 antibodies further in combination with interleukin-2 (IL-2) for the treatment of melanoma. The scientific rationale behind the combined use of LAG-3 and CTLA-4 and/or PD-1 and/or PD-L1 blockade with chemotherapy is that cell death, which is a consequence of the cytotoxic action of most chemotherapeutic compounds, should result in increased levels of tumor antigen in the antigen presentation pathway. Other combination therapies that may result in synergy with a combined LAG-3 and CTLA-4 and/or PD-1 and/or PD-L1 blockade through cell death include radiation, surgery, or hormone deprivation. Each of these protocols creates a source of tumor antigen in the host. Angiogenesis inhibitors can also be combined with a combined LAG-3 and CTLA-4 and/or PD-1 and/or PD-L1 blockade. Inhibition of angiogenesis leads to tumor cell death, which can be a source of tumor antigen fed into host antigen presentation pathways.

A combination of LAG-3 and CTLA-4 and/or PD-1 and/or PD-L1 blocking antibodies can also be used in combination with bispecific antibodies that target Fcα or Fcγ receptor-expressing effector cells to tumor cells (see, e.g., U.S. Pat. Nos. 5,922,845 and 5,837,243). Bispecific antibodies can be used to target two separate antigens. The T cell arm of these responses would be augmented by the use of a combined LAG-3 and CTLA-4 and/or PD-1 and/or PD-L1 blockade.

In another example, a combination of anti-LAG-3 and anti-CTLA-4 and/or anti-PD-1 antibodies and/or anti-PD-L1 antibodies can be used in conjunction with anti-neoplastic antibodies, such as Rituxan® (rituximab), Herceptin® (trastuzumab), Bexxar® (tositumomab), Zevalin® (ibritumomab), Campath® (alemtuzumab), Lymphocide® (eprtuzumab), Avastin® (bevacizumab), and Tarceva® (erlotinib), and the like. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4, PD-1, PD-L1 or LAG-3. In an exemplary embodiment, a treatment of a hyperproliferative disease (e.g., a cancer tumor) can include an anti-cancer antibody in combination with anti-LAG-3 and anti-CTLA-4 and/or anti-PD-1 and/or anti-PD-L1 antibodies, concurrently or sequentially or any combination thereof, which can potentiate an anti-tumor immune responses by the host.

Tumors evade host immune surveillance by a large variety of mechanisms. Many of these mechanisms may be overcome by the inactivation of proteins, which are expressed by the tumors and which are immunosuppressive. These include, among others, TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). In another example, antibodies to each of these entities can be further combined with an anti-LAG-3 and anti-CTLA-4 and/or anti-PD-1 and/or anti-PD-L1 antibody combination to counteract the effects of immunosuppressive agents and favor anti-tumor immune responses by the host.

Other antibodies that can be used to activate host immune responsiveness can be further used in combination with an anti-LAG-3 and anti-CTLA-4 and/or anti-PD-1 and/or anti-PD-L1 antibody combination. These include molecules on the surface of dendritic cells that activate DC function and antigen presentation. Anti-CD40 antibodies (Ridge et al., supra) can be used in conjunction with an anti-LAG-3 and anti-CTLA-4 and/or anti-PD-1 and/or anti-PD-L1 combination (Ito et al., supra). Other activating antibodies to T cell costimulatory molecules Weinberg et al., supra, Melero et al. supra, Hutloff et al., supra) may also provide for increased levels of T cell activation.

As discussed above, bone marrow transplantation is currently being used to treat a variety of tumors of hematopoietic origin. A combined LAG-3 and CTLA-4 and/or PD-1 and/or PD-L1 blockade can be used to increase the effectiveness of the donor engrafted tumor specific T cells.

Several experimental treatment protocols involve ex vivo activation and expansion of antigen specific T cells and adoptive transfer of these cells into recipients in order to antigen-specific T cells against tumor (Greenberg & Riddell, supra). These methods can also be used to activate T cell responses to infectious agents such as CMV. Ex vivo activation in the presence of anti-LAG-3 and anti-CTLA-4 and/or anti-PD-1 and/or anti-PD-L1 antibodies can be expected to increase the frequency and activity of the adoptively transferred T cells.

In certain embodiments, the present invention provides a method for altering an adverse event associated with treatment of a hyperproliferative disease (e.g., cancer) with an immunostimulatory agent, comprising administering a anti-LAG-3 antibody and a subtherapeutic dose of anti-CTLA-4 and/or anti-PD-1 and/or anti-PD-L1 antibody to a subject. For example, the methods of the present invention provide for a method of reducing the incidence of immunostimulatory therapeutic antibody-induced colitis or diarrhea by administering a non-absorbable steroid to the patient. Because any patient who will receive an immunostimulatory therapeutic antibody is at risk for developing colitis or diarrhea induced by such an antibody, this entire patient population is suitable for therapy according to the methods of the present invention. Although steroids have been administered to treat inflammatory bowel disease (IBD) and prevent exacerbations of IBD, they have not been used to prevent (decrease the incidence of) IBD in patients who have not been diagnosed with IBD. The significant side effects associated with steroids, even non-absorbable steroids, have discouraged prophylactic use.

In further embodiments, a combination LAG-3 and CTLA-4 and/or PD-1 and/or PD-L1 blockade (i.e., immunostimulatory therapeutic antibodies anti-LAG-3 and anti-CTLA-4 and/or anti-PD-1 antibodies and/or anti-PD-L1 antibodies) can be further combined with the use of any non-absorbable steroid. As used herein, a "non-absorbable steroid" is a glucocorticoid that exhibits extensive first pass metabolism such that, following metabolism in the liver, the bioavailability of the steroid is low, i.e., less than about 20%. In one embodiment of the invention, the non-absorbable steroid is budesonide. Budesonide is a locally-acting glucocorticosteroid, which is extensively metabolized, primarily by the liver, following oral administration. ENTOCORT EC® (Astra-Zeneca) is a pH- and time-dependent oral formulation of budesonide developed to optimize drug delivery to the ileum and throughout the colon. ENTOCORT EC® is approved in the U.S. for the treatment of mild to moderate Crohn's disease involving the ileum and/or ascending colon. The usual oral dosage of ENTOCORT EC® for the treatment of Crohn's disease is 6 to 9 mg/day. ENTOCORT EC® is released in the intestines before being absorbed and retained in the gut mucosa. Once it passes through the gut mucosa target tissue, ENTOCORT EC® is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT EC® can result in systemic glucocorticoid effects such as hypercorticism and adrenal suppression. See PDR 58$^{th}$ ed. 2004; 608-610.

In still further embodiments, a combination LAG-3 and CTLA-4 and/or PD-1 and/or PD-L1 blockade (i.e., immunostimulatory therapeutic antibodies anti-LAG-3 and anti-CTLA-4 and/or anti-PD-1 and/or anti-PD-L1 antibodies) in conjunction with a non-absorbable steroid can be further combined with a salicylate. Salicylates include 5-ASA agents such as, for example: sulfasalazine (AZULFIDINE®, Pharmacia & UpJohn); olsalazine (DIPENTUM®, Pharmacia & UpJohn); balsalazide (COLAZAL®, Salix Pharmaceuticals, Inc.); and mesalamine (ASACOL®, Procter & Gamble Pharmaceuticals; PENTASA®, Shire US; CANASA®, Axcan Scandipharm, Inc.; ROWASA®, Solvay).

In accordance with the methods of the present invention, a salicylate administered in combination with anti-LAG-3 and anti-CTLA-4 and/or anti-PD-1 and/or anti-PD-L1 antibodies and a non-absorbable steroid can includes any overlapping or sequential administration of the salicylate and the non-absorbable steroid for the purpose of decreasing the incidence of colitis induced by the immunostimulatory antibodies. Thus, for example, methods for reducing the incidence of colitis induced by the immunostimulatory antibodies according to the present invention encompass administering a salicylate and a non-absorbable concurrently or sequentially (e.g., a salicylate is administered 6 hours after a non-absorbable steroid), or any combination thereof. Further, according to the present invention, a salicylate and a non-absorbable steroid can be administered by the same route (e.g., both are administered orally) or by different routes (e.g., a salicylate is administered orally and a non-absorbable steroid is administered rectally), which may differ from the route(s) used to administer the anti-LAG-3 and anti-CTLA-4 and/or anti-PD-1 and/or anti-PD-L1 antibodies.

The present disclosure is further illustrated by the following examples, which should not be construed as further limiting. The contents of all figures and all references, Genbank sequences, patents and published patent applications cited throughout this application are expressly incorporated herein by reference. In particular, the disclosures of PCT publications WO 09/045957, WO 09/073533, WO 09/073546, and WO 09/054863 are expressly incorporated herein by reference.

Example 1: Generation of Human Monoclonal Antibodies Against LAG-3

Anti-LAG-3 human monoclonal antibodies were generated using transgenic mice that express human antibody genes, as follows.

Antigens

Recombinant human LAG-3 fusion proteins were used as the immunogen to raise anti-human LAG-3 antibodies. In certain immunizations, a fusion protein comprising the entire extracellular region (domains 1-4) of human LAG-3 fused to a human immunoglobulin Fc domain (R&D Systems, Catalog #2319-L3) (D1-D4 hFc) or a mouse immunoglobulin Fc domain (D1-D4 mFc) was used as the immunogen. For other immunizations, a fusion protein comprising only the first two extracellular domains of human LAG-3 fused to a mouse immunoglobulin Fc domain (D1-D2 mFc) was used as the immunogen. The LAG-3 fusion proteins were prepared using standard recombinant DNA techniques.

Transgenic Transchromosomic KM Mouse™ and KM/FCGR2D Mouse™ Strains

Fully human monoclonal antibodies to human LAG-3 were prepared using mice of the transgenic transchromosomic KM Mouse™ and KM/FCGR2D Mouse™ strains, which expresses human antibody genes.

In the KM Mouse™ strain, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187. Furthermore, this mouse strain carries a human kappa light chain transgene, KCo5, as described in Fishwild et al., supra. The strain also contains the SC20 transchromosome, which carries the human Ig heavy chain locus, as described in PCT Publication WO 02/43478. The KM/FCGR2D Mouse™ strain is the same as the KM Mouse™ strain except that its genome also comprises a homozygous disruption of the endogenous FcγRIIB gene. The KM Mouse™ and KM/FCGR2D Mouse™ strains are also described in detail in U.S. Application Publication No. 20020199213.

KM Mouse™ and KM/FCGR2D Mouse™ Immunizations:

To generate fully human monoclonal antibodies to LAG-3, mice of the KM Mouse™ and KM/FCGR2D Mouse™ strains were immunized with one of the three different recombinant LAG-3 fusion protein described above (D1-D4 hFc, D1-D4 mFc, D1-D2, mFc). General immunization schemes are described in Lonberg et al. (1994) supra; Fishwild et al., supra and PCT Publication WO 98/24884. The mice were 6-16 weeks of age upon the first infusion of antigen. Mice were immunized intraperitoneally (IP) and/or subcutaneously (SC). The mice were immunized biweekly four times with g of the recombinant LAG-3 fusion protein, followed by immunization twice with g of the same immunogen in Ribi as an adjuvant. The immune response was monitored by retroorbital bleeds. The plasma was screened by ELISA (as described below), and mice with sufficient titers of anti-LAG-3 human immunoglobulin were used for fusions. Prior to sacrifice and removal of the spleens, the mice were boosted intravenously and intraperitoneally with 20 µg of antigen followed by a subsequent intravenous boost with 20 µg of antigen.

Selection of KM and KM/FCGR2D Mice Producing Anti-LAG-3 Antibodies To select mice producing antibodies that bound LAG-3 protein, sera from mice immunized with the D1-D4 hFc fusion protein were tested by a modified ELISA as originally described by Fishwild et al. (1996). Briefly, microtiter plates were coated with purified recombinant LAG-3 fusion protein at 1 µg/ml in PBS, 50 µl/wells incubated 4° C. overnight, then blocked with 200 µl/well of 5% BSA in PBS. Dilutions of plasma from LAG-3-immunized mice were added to each well and incubated for 1-2 hours at ambient temperature. The plates were washed with PBS/Tween and then incubated with a goat-anti-human kappa light chain polyclonal antibody conjugated with Horse Radish Peroxidase (HRP) for 1 hour at room temperature. After washing, the plates were developed with ABTS substrate and analyzed by spectrophotometer at OD 405.

For mice immunized with the D1-D4 mFc or D1-D2 mFc fusion proteins, sera from these mice with were tested by indirect ELISA using goat anti-mouse IgG to coat the plates for one hour prior to coating with the antigen to eliminate nonspecific binding to the mouse Fc part. Then the same ELISA steps as described above were carried out.

Mice that developed the highest titers of anti-LAG-3 antibodies were used for fusions. Fusions were performed as described below and hybridoma supernatants were tested for anti-LAG-3 activity by ELISA.

Generation of Hybridomas Producing Human Monoclonal Antibodies to LAG-3 Proteins The mouse splenocytes, isolated from the KM or KM/FCGR2D mice, were fused by electric field based electrofusion using a Cyto Pulse large chamber cull fusion electroporator (Cyto Pulse Sciences, Inc., Glen Burnie, Md.) to a mouse myeloma cell line. The resulting hybridomas were then screened for the production of antigen-specific antibodies. Single cell suspensions of splenic lymphocytes from immunized mice were fused to one-fourth the number of P3X63 Ag8.6.53 (ATCC CRL 1580) nonsecreting mouse myeloma cells. Cells were plated at approximately $1 \times 10^5$/well in flat bottom microtiter plate, followed by about two week incubation in selective medium containing 10% fetal calf serum, supplemented with origen (IGEN) in RPMI, L-glutamine, sodium pyruvate, HEPES, penicillin, streptamycin, gentamycin, 1×HAT, and β-mercaptoethanol. After 1-2 weeks, cells were cultured in medium in which the HAT was replaced with HT. Individual wells were then screened by ELISA (described above) for human anti-LAG-3 monoclonal IgG antibodies. Once extensive hybridoma growth occurred, medium was monitored usually after 10-14 days. The antibody secreting hybridomas were replated, screened again and, if still positive for human IgG, anti-LAG-3 monoclonal antibodies were subcloned at least twice by limiting dilution. The stable subclones were then cultured in vitro to generate small amounts of antibody in tissue culture medium for further characterization.

Hybridoma clones 25F7, 26H10, 25E3, 8B7, 11F2 and 17E5 were selected for further analysis and sequencing.

Example 2: Structural Characterization of Human Anti-LAG-3 Monoclonal Antibodies 25F7, 26H10, 25E3, 8B7, 11F2 and 17E5

The cDNA sequences encoding the heavy and light chain variable regions of the mAbs expressed by the 25F7, 26H10, 25E3, 8B7, 11F2 and 17E5 clones, as described in Example 1, were sequenced using the following protocol. Total RNA was prepared from $5 \times 10^6$ hybridoma cells using the RNeasy Mini Kit (Qiagen, Valencia, Calif.). cDNA was prepared by the 5'-RACE protocol with the SMART RACE cDNA Amplification Kit (Clontech Laboratories, Inc., Mountain View, Calif.) and SuperScript II Reverse Transcriptase (Invitrogen, Carlsbad, Calif.). V-regions of each antibody were amplified using a 3' human-specific constant region primer, paired with the 5' RACE universal primer mix. PCR products containing the V-region were cloned into the pCR4-TOPO vector (Invitrogen, Carlsbad, Calif.) and transformed into E. coli strain TOP10 (Invitrogen, Carlsbad, Calif.). Either miniprep DNA or Templiphi (GE Healthcare Biosciences, Piscataway, N.J., USA) samples were prepared, and subjected to DNA sequencing (Sequetech, Mountain View, Calif.). The resultant DNA sequences were analyzed for in-frame rearrangements and other antibody characteristics. The expressed proteins were characterized by standard protein chemistry analysis. The 25E3, 25F7 and 26H10 clones were found to express an antibody comprising an IgG1 heavy chain and a kappa light chain, whereas the 8B7 and 17E5 clones were found to express an antibody comprising an IgG4 heavy chain and a kappa light chain and the 11F2 clone was found to express an antibody comprising an IgG2 heavy chain and a kappa light chain.

The nucleotide and amino acid sequences of the heavy chain variable region of 25F7 are shown in FIG. 1A and in SEQ ID NO: 49 and 37, respectively. The nucleotide and amino acid sequences of the kappa light chain variable region of 25F7 are shown in FIG. 1B and in SEQ ID NO: 55 and 43, respectively. Comparison of the 25F7 heavy chain immunoglobulin sequence to the known human germline immunoglobulin heavy chain sequences (FIG. 7) showed that the 25F7 heavy chain utilizes a $V_H$ segment from human germline $V_H$ 4-34 (SEQ ID NO:61), and a JH segment from human germline JH5b (SEQ ID NO:62). Further analysis of the 25F7 $V_H$ sequence using the Kabat system of CDR region determination led to the delineation of the heavy chain CDR1, CDR2 and CDR3 regions as shown in FIG. 1A and in SEQ ID NOs: 1, 7 and 13, respectively. Comparison of the 25F7 light chain immunoglobulin sequence to the known human germline immunoglobulin light chain sequences (FIG. 8) showed that the 25F7 kappa light chain utilizes a $V_K$ segment from human germline $V_K$ L6 (SEQ ID NO:63) and a $J_K$ segment from human germline JK 2 (SEQ ID NO:64). Further analysis of the 25F7 $V_K$ sequence using the Kabat system of CDR region determination led to the delineation of the light chain CDR1, CDR2 and CDR3 regions as shown in FIG. 1B and in SEQ ID NOs: 19, 25 and 31, respectively.

The nucleotide and amino acid sequences of the heavy chain variable region of 26H10 are shown in FIG. 2A and in SEQ ID NO: 50 and 38, respectively. The nucleotide and amino acid sequences of the light chain variable region of 26H10 are shown in FIG. 2B and in SEQ ID NO: 56 and 44, respectively. Comparison of the 26H10 heavy chain immunoglobulin sequence to the known human germline immunoglobulin heavy chain sequences (FIG. 9) showed that the 26H10 heavy chain utilizes a $V_H$ segment from human germline $V_H$ 3-33 (SEQ ID NO:65), and a JH segment from human germline JH 6B (SEQ ID NO:66). Further analysis of the 26H10 $V_H$ sequence using the Kabat system of CDR region determination led to the delineation of the heavy chain CDR1, CDR2 and CDR3 regions as shown in FIG. 2A and in SEQ ID NOs: 2, 8 and 14, respectively. Comparison of the 26H10 light chain immunoglobulin sequence to the known human germline immunoglobulin light chain sequences (FIG. 10) showed that the 26H10 kappa light chain utilizes a $V_k$ segment from human germline $V_K$ A27 (SEQ ID NO:67) and a $J_K$ segment from human germline JK 3 (SEQ ID NO:68). Further analysis of the 26H10 $V_k$ sequence using the Kabat system of CDR region determination led to the delineation of the light chain CDR1, CDR2 and CDR3 regions as shown in FIG. 2B and in SEQ ID NOs: 20, 26 and 32, respectively.

The nucleotide and amino acid sequences of the heavy chain variable region of 25E3 are shown in FIG. 3A and in SEQ ID NO: 51 and 39, respectively. The nucleotide and amino acid sequences of the light chain variable region of 25E3 are shown in FIG. 3B and in SEQ ID NO: 57 and 45, respectively. Comparison of the 25E3 heavy chain immunoglobulin sequence to the known human germline immunoglobulin heavy chain sequences (FIG. 11) showed that the 25E3 heavy chain utilizes a $V_H$ segment from human germline $V_H$ 3-20 (SEQ ID NO:69), and a JH segment from human germline JH 4b (SEQ ID NO:70). Further analysis of the 25e3 $V_H$ sequence using the Kabat system of CDR region determination led to the delineation of the heavy chain CDR1, CDR2 and CDR3 regions as shown in FIG. 3A and in SEQ ID NOs: 3, 9 and GGY, respectively. Comparison of the 25E3 light chain immunoglobulin sequence to the known human germline immunoglobulin light chain sequences (FIG. 12) showed that the 25E3 kappa light chain utilizes a $V_k$ segment from human germline $V_K$ L18 (SEQ ID NO:71) and a $J_K$ segment from human germline JK 2 (SEQ ID NO:64). Further analysis of the 25E3 $V_k$ sequence using the Kabat system of CDR region determination led to the delineation of the light chain CDR1, CDR2 and CDR3 regions as shown in FIG. 3B and in SEQ ID NOs: 21, 27 and 33, respectively.

The nucleotide and amino acid sequences of the heavy chain variable region of 8B7 are shown in FIG. 4A and in SEQ ID NO: 52 and 40, respectively. The nucleotide and amino acid sequences of the light chain variable region of 8B7 are shown in FIG. 4B and in SEQ ID NO: 58 and 46, respectively. Comparison of the 8B7 heavy chain immunoglobulin sequence to the known human germline immunoglobulin heavy chain sequences (FIG. 13) showed that the 8B7 heavy chain utilizes a $V_H$ segment from human germline $V_H$ 4-34 (SEQ ID NO:61), and a JH segment from human germline JH 5B (SEQ ID NO:62). Further analysis of the 8B7 $V_H$ sequence using the Kabat system of CDR region determination led to the delineation of the heavy chain CDR1, CDR2 and CDR3 regions as shown in FIG. 4A and in SEQ ID NOs: 4, 10 and 16, respectively. Comparison of the 8B7 light chain immunoglobulin sequence (FIG. 14) to the known human germline immunoglobulin light chain sequences showed that the 8B7 kappa light chain utilizes a $V_k$ segment from human germline $V_K$ L6 (SEQ ID NO:63) and a $J_K$ segment from human germline JK 4 (SEQ ID NO:72). Further analysis of the 26H10 $V_k$ sequence using the Kabat system of CDR region determination led to the delineation of the light chain CDR1, CDR2 and CDR3 regions as shown in FIG. 4B and in SEQ ID NOs: 22, 28 & 34, respectively.

The nucleotide and amino acid sequences of the heavy chain variable region of 11F2 are shown in FIG. 5A and in SEQ ID NO: 53 and 41, respectively. The nucleotide and amino acid sequences of the light chain variable region of 11F2 are shown in FIG. 5B and in SEQ ID NO: 59 and 47, respectively. Comparison of the 11F2 heavy chain immunoglobulin sequence to the known human germline immunoglobulin heavy chain sequences (FIG. 15) showed that the 11F2 heavy chain utilizes a $V_H$ segment from human germline $V_H$ 1-24 (SEQ ID NO:73), a D segment from the human germline 2-15, and a JH segment from human germline JH 4B (SEQ ID NO:70). Further analysis of the 11F2 $V_H$ sequence using the Kabat system of CDR region determination led to the delineation of the heavy chain CDR1, CDR2 and CDR3 regions as shown in FIG. 13A and in SEQ ID NOs: 5, 11 and 17, respectively. Comparison of the 11F2 light chain immunoglobulin sequence to the known human germline immunoglobulin light chain sequences (FIG. 16) showed that the 11F2 kappa light chain utilizes a $V_k$ segment from human germline $V_K$ L6 (SEQ ID NO:63) and a $J_K$ segment from human germline JK 1 (SEQ ID NO:74). Further analysis of the 11F2 $V_k$ sequence using the Kabat system of CDR region determination led to the delineation of the light chain CDR1, CDR2 and CDR3 regions as shown in FIG. 5B and in SEQ ID NOs: 23, 29 and 35, respectively.

The nucleotide and amino acid sequences of the heavy chain variable region of 17E5 are shown in FIG. 6A and in SEQ ID NO: 54 and 42, respectively. The nucleotide and amino acid sequences of the light chain variable region of 17E5 are shown in FIG. 6B and in SEQ ID NO: 60 and 48, respectively. Comparison of the 17E5 heavy chain immunoglobulin sequence to the known human germline immunoglobulin heavy chain sequences (FIG. 17) showed that the 17E5 heavy chain utilizes a $V_H$ segment from human germline $V_H$ 3-33 (SEQ ID NO:65), a D segment from the human germline 2-2, and a JH segment from human germline JH 4B (SEQ ID NO:70). Further analysis of the 17E5 $V_H$ sequence using the Kabat system of CDR region determination led to the delineation of the heavy chain CDR1, CDR2 and CDR3 regions as shown in FIG. 6A and in SEQ ID NOs: 6, 12 and 18, respectively. Comparison of the 17E5 light chain immunoglobulin sequence to the known human germline immunoglobulin light chain sequences (FIG. 18) showed that the 17E5 kappa light chain utilizes a $V_k$ segment from human germline $V_K$ L6 (SEQ ID NO:63) and a $J_K$ segment from human germline JK 5 (SEQ ID NO:75). Further analysis of the 17E5 $V_k$ sequence using the Kabat system of CDR region determination led to the delineation of the light chain CDR1, CDR2 and CDR3 regions as shown in FIG. 6B and in SEQ ID NOs: 24, 30 and 36, respectively.

The 25F7, 26H10, 25E3, 8B7, 11F2 and 17E5 variable regions can be converted to full-length antibodies of any desired isotype using standard recombinant DNA techniques. For example, DNA encoding the $V_H$ and $V_L$ regions can be cloned into an expression vector that carries the heavy and light chain constant regions such that the variable regions are operatively linked to the constant regions. Alternatively, separate vectors can be used for expression of the full-length heavy chain and the full-length light chain. Non-limiting examples of expression vectors suitable for use in creating full-length antibodies include the pIE vectors described in U.S. Patent Publication No. 20050153394.

Example 3: Characterization of Binding Properties of LAG-3 Monoclonal Antibodies In this example, the binding of human anti-LAG-3 antibodies to cell surface LAG-3 (human, monkey and mouse LAG-3) was examined by flow cytometry. Furthermore, binding kinetics to LAG-3 were analyzed by BIACORE analysis. Still further epitope mapping was conducted using a peptide scan experiment.

A. Flow Cytometry Studies

1. CHO-human LAG-3 Cell Binding

To test the ability of the antibodies to bind to cell surface LAG-3 protein, the antibodies were incubated with a CHO cell line that had been transfected to express human LAG-3 on the cell surface. The 25F7, 26H10, 25E3, 8B7, 11F2 and 17E5 monoclonal antibodies were serially diluted with cold 1×PFAE buffer (1×PBS+2% FBS, 0.02% sodium azide, 2 mM Na EDTA). For the binding reaction, 50 µl of diluted antibody solution was added to a 50 µl cell suspension containing $2 \times 10^5$ cells and the mixture was incubated on ice for 30 minutes. The cells were then washed two times with 1×PFAE buffer. A 1:100 dilution of FITC-labeled goat anti-human kappa light chain antibody (Bethyl Laboratories, Inc., Cat. #A80-115F) was added and the mixture was incubated for 30 minutes at 4° C., followed by washing twice with cold 1×PFAE buffer. After the final wash, 150 µl of cold 1×PFAE containing 10 µg/mL propidium iodide (Roche Applied Science, Cat #1_348_639) was added to each solution and analysis of antibody binding was carried out by flow cytometry using a FACScalibur flow cytometer (BD Bioscience).

The results of the flow cytometry analysis are summarized below in Table 1, which shows $EC_{50}$ for binding to CHO-human LAG-3, demonstrating that 25F7, 26H10, 25E3, 8B7, 11F2 and 17E5 bind effectively to cell-surface human LAG-3, with 25F7 having approximately a 20 fold lower $EC_{50}$ than 25E3 but approximately equivalent $EC_{50}$ to that of 8B7 and 26H10. The $EC_{50}$ results for 11F2 and 17E5 were in the same range as for 25E3.

TABLE 1

Binding of Anti-LAG-3 Antibodies to CHO Cells Expressing Human LAG-3

| Antibody | $EC_{50}$ (nM) |
| --- | --- |
| 25F7 | 0.45-2.52 |
| 8B7 | 1.93-4.44 |

TABLE 1-continued

Binding of Anti-LAG-3 Antibodies to
CHO Cells Expressing Human LAG-3

| Antibody | $EC_{50}$ (nM) |
| --- | --- |
| 26H10 | 1.81-3.64 |
| 11F2 | 15.12 |
| 25E3 | 14.9-25.39 |
| 17E5 | 12.3 |

2. Activated human CD4+ T Cell Binding

To test the ability of the antibodies to bind to native human LAG-3 on the surface of activated human T cells, resting CD4+ T cells were isolated from purified peripheral blood mononuclear cells and subjected to three days of stimulation with a combination of anti-CD3 and anti-CD28 antibodies affixed to polystyrene beads. The 25F7, 8B7 and 26H10 monoclonal antibodies were serially diluted with cold 1×PFAE buffer (1×PBS+2% FBS, 0.02% sodium azide, 2 mM Na EDTA). For the binding reaction, 50 µl of diluted antibody solution was mixed with 50 µl of PE-labeled anti-human CD4 (BD Bioscience, Cat #555347). Activated T cells were processed by the same protocol described above. The analysis of antibody binding was conducted as described above.

The results of the flow cytometry analysis are summarized below in Table 2, which shows $EC_{50}$ for binding to activated human CD4+ T cells, demonstrating that all three antibodies bind similarly to cell-surface human LAG-3.

TABLE 2

Binding of Anti-LAG-3 Antibodies
to Activated human CD4+ T cells

| Antibody | $EC_{50}$ (nM) |
| --- | --- |
| 25F7 | 0.27-0.45 |
| 26H10 | 0.41-0.84 |
| 8B7 | 0.69-1.80 |

3. Monkey LAG-3 Antigen Binding

To determine whether the anti-LAG-3 antibodies cross-react with monkey LAG-3, a cDNA sequence was cloned by RT-PCR from a preparation of pooled cDNA prepared by reverse transcription of RNAs from a collection of cynomolgus and rhesus monkey tissue samples. The sequence was first amplified from the cDNA pool using primers (5' forward primer: 5Mcyn1408; 5'-atgtgggaggctcagttcctg-3' (SEQ ID NO: 91) & 3' reverse primer: 3Mcyn1408a; 5'-gtcagagctgctccggctc-3' (SEQ ID NO: 92)) using a GC-rich PCR amplification system (Roche) and was cloned into a recipient TOPO cloning vector (Invitrogen) for sequence analysis. Clones matching the reference Genbank rhesus monkey LAG-3 sequence (Genbank Accession No. XM_001108923) were subsequently re-amplified from the TOPO-cloning vector DNA utilizing a second set of primers that incorporated restriction enzyme sites for directional cloning in a mammalian cell expression vector.

Monkey LAG-3 clone pa23-5 was isolated and sequenced. The isolated monkey sequence exhibited 99.6% identity to the reference Genbank rhesus monkey LAG-3 sequence. A comparison of the amino acid sequence of cDNA clone pa23-3 (SEQ ID NO: 93) with rhesus monkey LAG-3 (SEQ ID NO: 94) from Genbank (Accession No. XM_001108923) is shown in FIG. 19. The two sequences are identical except for a one amino acid difference at position 419 (arginine in clone pa23-5 versus threonine in the Genbank rhesus sequence) and on this basis it is concluded that cDNA clone pa23-5 represents the rhesus LAG-3 gene sequence.

The cDNA of clone pa23-5 was inserted into an expression construct, which was transfected into CHO-S suspension cells by nucleofection (Amaxa). Rhesus LAG-3 expression by sorted, selection drug-resistant clones was verified by FACS analysis. This clonal CHO cell line over-expressing rhesus LAG-3 was used in similar FACS assays to those described above to measure antibody cross reactivity to the monkey protein. Briefly, the 25F7, 8B7 and 26H10 monoclonal antibodies were serially diluted with cold 1×PFAE buffer (1×PBS+2% FBS, 0.02% sodium azide, 2 mM Na EDTA). For the binding reaction, 50 µl of diluted antibody solution was added to a 50 µl cell suspension containing $2×10^5$ cells and the mixture was incubated on ice for 30 minutes. The cells were processed by the same protocol described above. The analysis of antibody binding was conducted as described above.

In a separate experiment, the antibodies were tested for binding to cynomolgus monkey LAG-3 using activated cynomolgus monkey T cells. In vitro activation of these monkey T cells was achieved through anti-CD3/anti-CD28 treatment of the T cells by essentially the same protocol described above for the in vitro activation of human T cells, followed by flow cytometry analysis performed as described above for staining of in vitro activated human CD4+ T cells.

The results of the flow cytometry analyses using the CHO-rhesus LAG-3 cells and the activated cynomolgus T cells are summarized below in Table 3, which shows $EC_{50}$ for binding to the two different types of cells expressing monkey LAG-3. These results showed that all antibodies bind effectively to both LAG-3 on the activated cynomolgus T cells and the rhesus LAG-3 (SEQ ID NO: 93) transfected into CHO cells. There is a hierarchy, however, of binding affinities, with clone 26H10 showing the highest affinity, which is approximately 2.5 and 6-fold better than that of clones 8B7 and 25F7, respectively. Difference in binding hierarchy between the two cell types may reflect amino acid sequence differences between the rhesus and cynomolgus LAG-3 proteins.

TABLE 3

Binding of Anti-LAG-3 Antibodies to Monkey LAG-3

| Antibody | Activated Cyno CD4+ T cells $EC_{50}$ (nM) | CHO-rhesus LAG3 $EC_{50}$ (nM) |
| --- | --- | --- |
| 26H10 | 5.19 | 4.684 |
| 25F7 | 14.18 | 22.72 |
| 8B7 | 30.45 | 10.01 |

4. Mouse LAG-3 Antigen Binding

To determine whether the antibodies cross-reacted with mouse LAG-3, similar flow cytometry studies to those described above were performed using as the target cell a mouse T cell hybridoma cell line (3A9) that had been transfected to express mouse LAG-3 on its cell surface, followed by FACS analysis to detect antibody binding. The results indicated that, in contrast to a control anti-mouse LAG3 control antibody which showed strong staining, none of the human antibodies 25E3, 25F7, 8B7 or 26H10 exhibited binding above background levels to cell surface mouse LAG-3, demonstrating that none of these antibodies cross-react with mouse LAG-3.

B. BIACORE Analysis

The binding of the 25E3, 25F7, 8B7, 26H10 and 17E5 antibodies to recombinant LAG-3 protein was examined by BIAcore™ using a capture method. The 25E3, 25F7, 8B7, 26H10 and 17E5 antibodies each were captured using anti-CH1, a reagent antibody that is specific towards the heavy chain constant region 1 of human antibody (Zymed, Clone HP6045, Stock conc. 1.0 mg/mL). Anti-CH1 was coated on a CM5 chip (BR-1000-14, Research Grade) at high density (9700-11500RUs). The coating was carried out based on the standard immobilization procedure recommended by the manufacturer. The 25E3, 25F7, 8B7, 26H10 or 17E5 purified antibody, with concentrations ranging from 0.5-3 μg/mL, was then captured on the anti-CH1 coated surface at the flow-rate of 10 uL/min for 1 minute. A single concentration of recombinant human LAG-3 fusion protein (20 nM) was injected over captured antibody for 3 minutes at a flow rate of 25 μg/mL. The antigen was allowed to dissociate for 7.5 minutes. The chip surface was regenerated after each cycle with 25 μL of 25 mM NaOH followed by 30 μL of HBS-EP wash. Isotype controls were run on the chip, and the data used to subtract non-specific binding. All the experiments were carried out on a Biacore 3000 surface plasmon resonance instrument, using BIAcore Control software v 3.2. Data analysis was carried out using BiaEvaluation v3.2 software. The results are shown in Table 4 below. The BIAcore results for 25E3, 25F7, 8B7, 26H10 and 17E5 confirm the flow cytometry results that all five antibodies are capable of binding with high affinity to human LAG-3.

TABLE 4

Binding Kinetics of Anti-LAG-3 Antibody to Recombinant Human LAG-3

| Antibody | $K_D \times 10^{-9}$ (M) |
| --- | --- |
| 25E3 | 0.09 |
| 8B7 | 0.09 |
| 26H10 | 0.10 |
| 25F7 | 0.47 |
| 17E5 | 4.53 |

C. Epitope Mapping

In the LAG-3 protein, the immunoglobulin-like first domain of the extracellular region contains an exposed "extra loop" having the amino acid sequence: GPPAAAPGHPLAPGPHPAAPSSWGPRPRRY (SEQ ID NO: 79). To examine the binding of 25E3, 25F7, 8B7 and 26H10 to this region of LAG-3, and map the epitope bound by each antibody, a peptide scan experiment was performed across this region. A series of 10 overlapping peptides that scanned across the full length of the extra loop sequence were prepared and conjugated to biotin. For ELISA analysis, microtiter plates pre-coated with streptavidin (Sigma-Aldrich, Cat #M5432) were used to capture the biotinylated loop peptide-conjugates applied in a 100 μl volume at a concentration of 2 g/mL and incubated 18 hours at 4° C., after which the plates were washed 3 times and blocked at room temperature for 1 hour with blocking buffer (1×PBS+10% FBS). Next, human anti-LAG-3 antibodies serially diluted 3-fold in blocking buffer from 10 g/mL were applied and the plates were incubated at room temperature for 2 hours and then washed three times. To detect bound human antibody a HRP-conjugated goat anti-human kappa light chain antibody (Bethyl Laboratories, Cat #A80-115P) was diluted to 1 μg/mL in blocking buffer and applied to assay wells for 1 hour followed by three washes and application of TMB substrate (eBioscience, Cat #00-4201-56). Optical density readings at 650 nm wavelength were made on a Spectramax 340PC spectrophotometer (Molecular Dynamics, Inc.). The results of the peptide scan experiment are summarized below in Table 5.

TABLE 5

Anti-LAG Antibody Binding to Peptide Scan of LAG-3 Extra Loop

| LAG-3 Extra Loop Peptide Scan | SEQ | 25E3 | 8B7 | 25F7 | 26H10 |
| --- | --- | --- | --- | --- | --- |
| GPPAAAPGHPLAPGPHPAAPSSWGPRPRRY | 79 | | | | |
| GPPAAAPGHPLA | 80 | − | − | − | − |
| PAAAPGHPLAPG | 81 | ++ | − | − | − |
| AAPGHPLAPGPH | 82 | ++ | − | − | − |
| PGHPLAPGPHPA | 83 | + | − | − | − |
| HPLAPGPHPAAP | 84 | ± | − | − | − |
| LAPGPHPAAPSS | 85 | − | − | − | − |
| PGPHPAAPSSWG | 86 | − | ++ | ++ | − |
| PHPAAPSSWGPR | 87 | − | ++ | ++ | − |
| PAAPSSWGPRPR | 88 | − | ++ | + | − |
| APSSWGPRPRRY | 89 | − | − | − | − |

Based on these results, it was determined that the 25E3 antibody recognized a region within the extracellular loop comprising the amino acid sequence PGHPLAPG (SEQ ID NO: 76), whereas the 25F7 antibody recognized a region within the extra loop comprising the amino acid sequence HPAAPSSW (SEQ ID NO: 77) and 8B7 appeared to recognize a region within the extracellular loop comprising the amino acid sequence PAAPSSWG (SEQ ID NO: 78). In contrast, no binding of the full length extra loop peptide or any of the shorter scanning peptides by the 26H10 antibody could be detected.

The regions identified in this study are underlined in the full-length extra loop sequence:

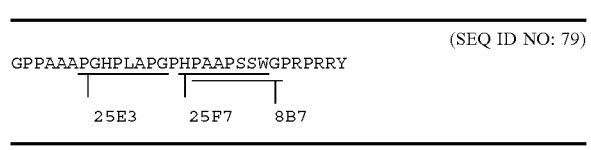

(SEQ ID NO: 79)

Thus, the peptide scan results indicate that the 25E3, 25F7 and 8B7 antibodies bind to different although closely located epitopes within human LAG-3.

To further examine binding of these antibodies to the extra loop peptide region, additional ELISA assays were performed. In an ELISA assay using the human full-length extra loop peptide (SEQ ID NO: 79), $EC_{50}$ values for binding were determined for 25E3, 25F7 and 8B7. Additionally, a similar peptide ELISA was conducted using the full length extra loop peptide sequence from rhesus monkey LAG-3, having the sequence GPPAPAPGHPPAPGHRPAAP YSWGPRPRRY (SEQ ID NO: 90), and $EC_{50}$ values for binding were determined for 25F7 and 8B7. The results are summarized below in Table 6. The results confirm that antibodies 25E3, 25F7 and 8B7 are capable of recognizing the human LAG-3 extra loop peptide region. Moreover, antibodies 25F7 and 8B7 also bind to the rhesus LAG-3 extra loop peptide region, albeit less well compared to the human sequence, which may be due to the species sequence divergence in this polypeptide. The results also confirm that the 26H10 antibody is not capable of recognizing the LAG-3 extra loop peptide.

TABLE 6

Binding of Anti-LAG-3 Antibodies to Human and Rhesus LAG-3 Extra Loop Peptide

| Antibody | Human Extra Loop $EC_{50}$ (nM) | Rhesus Extra Loop $EC_{50}$ (nM) |
| --- | --- | --- |
| 25E3 | 0.55 | Not tested |
| 25F7 | 0.29-0.95 | 13.09 |
| 8B7 | 0.28-1.35 | 0.60 |
| 26H10 | No binding | No binding |

Example 4: Inhibition of Binding of LAG-3 to MHC Class II by Anti-LAG-3 mAbs

To test the ability of the anti-LAG-3 antibodies to inhibit binding of LAG-3 to MHC Class II molecules, an in vitro binding assay was performed in which a LAG-3 fusion protein, comprising human LAG-3 extracellular domain fused to mouse Fc (hLAG-3-mIg), was reacted with Daudi cells, which express human MHC Class II molecules.

To test antibody inhibition of LAG-3 binding to MHC Class II, 25E3, 25F7, 8B7 and 26H10 were serially diluted from 20 µg/mL in PFAE buffer and to these serial dilutions was added 1 µg/ml of hLAG-3-mIg fusion protein. This mixture was incubated for 20 minutes at room temperature prior to adding to $2 \times 10^5$ 1×PFAE-washed Daudi cells. The mixture was applied to Daudi cells and incubated at 4° C. for 30 minutes. The cells were pelleted (three minutes, 400×g), washed once with 1×PFAE buffer and re-pelleted, and binding of hLAG-3-mIg to the Daudi cells was detected using a recombinant PE-labeled anti-mIgG Fcγ secondary reagent. Analysis of LAG-3-mIg binding was carried out with the FACScalibur flow cytometer (BD Bioscience). The results are summarized in Table 7 below, which shows $IC_{50}$ values in nM.

TABLE 7

Inhibition of LAG-3 Binding to MHC Class II by Anti-LAG-3 Antibodies

| Antibody | $IC_{50}$ (nM) |
| --- | --- |
| 25E3 | 0.8-6.78 |
| 25F7 | 0.12-0.92 |
| 8B7 | 0.19-0.95 |
| 26H10 | 0.10 |

The results demonstrate that all four antibodies are effective in inhibiting binding of LAG-3 to MHC Class II antibodies, with 25F7, 8B7 and 26H10 exhibiting $IC_{50}$ values approximately 7 to 13-fold lower than that of 25E3.

Example 5: Stimulation of Antigen-Specific T Cell Response by Anti-LAG-3 mAbs

To test the ability of the anti-LAG-3 antibodies to stimulate an antigen-specific T cell response, a 3A9 T Cell Peptide Stimulation Assay (see e.g., Workman et al. (2003) J. Immunol. 169:5392-5395; Workman et al. (2002) Eur. J. Immunol. 32:2255-2263) was used.

In this assay, a mouse T cell hybridoma, 3A9, specific for the peptide HEL48-62, was used as the responder T cell. The responder 3A9 T cell was retrovirally transduced to express either human LAG-3 or mouse LAG-3 on its cell surface. The antigen presenting cell (APC) used to present the HEL48-62 peptide antigen to the 3A9 cells was the mouse MHC Class II positive cell line LK35.2. Separate studies determined that a human LAG-3 fusion protein was capable of binding to mouse MHC Class II molecules, thereby validating the use of LK35.2 mouse APCs in this assay. Antigen-specific stimulation of the 3A9 cells was indicated by production of interleukin-2 (IL-2), the secretion of which was measured by ELISA (mouse IL-2 OptEIA kit, BD Bioscience, Cat #555148 according to manufacturer's recommendations).

Ectopic expression of human or mouse LAG-3 on the 3A9 T cells, in the absence of any antibodies, led to an inhibitory effect on antigen-specific responses when the transfected T cells were incubated with the LK35.2 APCs presenting the HEL48-62 peptide antigen, as indicated by an increase in the amount of peptide antigen needed to stimulate IL-2 production by the 3A9 cells in comparison to the peptide dose response profile of control 3A9 T cells.

To test antibody stimulation of the antigen-specific T cell response, the APC ($2.5 \times 10^4$ cells) was first preincubated with the antigenic peptide (200 nM) for 30 minutes at 37° C. and the 3A9 T cells ($5.0 \times 10^4$ cells expressing either mLAG-3, hLAG-3 or control cells) were preincubated with an anti-hLAG-3 antibody (25E3, 25F7, 8B7, 26H10, 11F2, 17E5), serially diluted in three fold dilution from 25 µg/mL) for 15 minutes at 37° C. The 3A9 T cells were then added to the antigen-pulsed APCs and the culture incubated for 24 hours at 37° C. The supernatants were then harvested and measured for production of mouse IL-2. The results for the 3A9 T cells expressing human LAG-3 are in Table 8, which shows $IC_{50}$ values in nM.

TABLE 8

Stimulation of Antigen-Specific T Cell Responses by Anti-LAG-3 Antibodies

| Antibody | 3A9-hLAG-3 Peptide Assay $IC_{50}$ (nM) |
|---|---|
| 25F7 | 0.14-1.94 |
| 26H10 | 1.45-6.49 |
| 8B7 | 3.25-13.90 |
| 25E3 | 3.88-70.78 |
| 11F2 | 81.50-240 |
| 17E5 | No inhibition |

The results show that antibodies 25F7, 8B7 and 26H10, and to a lesser extent 25E3, were able to stimulate IL-2 production in an antigen-specific T cell response assay, whereas antibody 11F2 exhibited minimal ability to inhibit and antibody 17E5 was not functional in this assay. None of the antibodies altered the measured IL-2 production by control 3A9 T cells or 3A9 T cells transfected with mouse LAG-3 protein, demonstrating the specificity of the stimulatory effect.

Example 6: Tumor Growth Inhibition by Anti-LAG-3 mAb, Alone or in Combination

To test the ability of anti-LAG-3 antibody, alone or in combination with another immunostimulatory antibody, to inhibit the growth of tumor cells in vivo, two different syngeneic mouse tumor graft models were used. The first model used murine SaIN fibrosarcoma cells. The second model used the murine MC38 colon cancer cell line.

In a first experiment, mice (A/J strain) were each implanted with 2×10$^6$ SaIN fibrosarcoma cells on day 0 and the tumor cells were allowed to grow for seven days. On day 7, day 10 and day 12 post-implantation, the mice were treated with 10 mg/kg of either an anti-LAG-3 mAb alone (the rat anti-mouse LAG-3 mAb C9B7W; eBioscience, Cat. No. 14-2231), an anti-PD-L1 antibody alone (an anti-mouse PD-L1 mAb 14D8), the anti-LAG-3 and anti-PD-L1 antibodies in combination, or an IgG1 isotype control antibody. The 14D8 mAb is a rat anti-mouse PD-L1 antibody that has been chimerized to contain the mouse IgG1 and mouse kappa constant regions.

Tumor volumes in the mice were measured for over 50 days post-implantation and mean and median tumor volumes were determined. Mean tumor growth inhibition was calculated (based on treatment with the isotype control IgG1 antibody being 0% inhibition). The results for day 24 post-implantation are summarized below in Table 9:

TABLE 9

Mean Tumor Growth Inhibition in SaIN Tumor Model

| Day | IgG1 | LAG-3 | PD-L1 | Combo |
|---|---|---|---|---|
| 24 | — | 68 | 74.9 | 95.8 |

Thus, anti-LAG3 antibody alone, or anti-PD-L1 antibody treatment alone, resulted in tumor growth inhibition, while the combination of both antibodies led to even greater tumor growth inhibition. With respect to the treatment groups, by the end of the experiment the results were that 4 of 10 mice treated with anti-LAG3 alone became tumor free, whereas only 1 of 10 mice treated with the control IgG1 antibody became tumor free. Similarly, 4 of 11 mice treated with anti-PD-L1 alone were rendered tumor free. Treatment of mice with the combination of anti-LAG3 and anti-PD-L1 resulted in 9 of 10 mice becoming tumor free; the remaining mouse not tumor free had an indolent tumor that remained small throughout the study.

Two additional studies used mice implanted with cells of the murine MC38 colon cancer cell line. In the first experiment, C57Bl/6 mice were each implanted with 2×10$^6$ MC38 cells on day 0, and were treated on day 7, day 10 and day 12 post-implantation with 200 µg/dose of anti-LAG-3 alone (C9B7W mAb), anti-PD-1 alone (the 4H2 mAb) or anti-LAG-3 and anti-PD-1 in combination. An IgG1 isotype matched antibody, at 400 µg/dose, was used as a control. The 4H2 mAb is a rat anti-mouse PD-1 antibody that has been chimerized to contain the mouse IgG1 and mouse kappa constant regions.

Mean tumor volume, median tumor volume and % survival was determined at 80 days post-implantation. The results showed that LAG-3 monotherapy in this tumor model (MC38) showed little or no activity in inhibiting tumor growth and none of the treated mice survived the duration of the experiment. In contrast, anti-PD-1 monotherapy showed significant activity, with 4 of 10 mice tumor free at the end of the experiment. Moreover, similar to the results with the SaIN model, the combination therapy of anti-LAG-3 plus anti-PD-1 was more effective than either treatment alone, with 7 of 8 mice being tumor free at the end of the experiment.

In a second experiment with the MC38 model, C57Bl/6 mice were each implanted with 2×10$^6$ MC38 cells on day 0, and were treated on day 5, day 8 and day 11 post-implantation with 200 µg/dose of test antibody and/or 400 µg/dose control IgG antibody, as follows: (i) an anti-IgG1 control antibody; (ii) an anti-LAG-3 mAb (C9B7W mAb) together with the control IgG1; (iii) an anti-PD-1 antibody (4H2) together with the control IgG1; (iv) an anti-CTLA-4 antibody (the 9D9 mouse anti-mouse CTLA-4 mAb) together with the control IgG1; (v) the anti-LAG-3 mAb together with the anti-PD-1 mAb; or (vi) the anti-LAG-3 mAb together with the anti-CTLA-4 mAb. The 9D9 mAb is a mouse anti-mouse CTLA-4 antibody that was raised in a mouse in which the endogenous mouse CTLA-4 had been knocked out.

Mean tumor volume, median tumor volume and % survival was determined for over 100 days post-implantation. The results were similar to the first experiment in that LAG-3 monotherapy showed little or no activity in inhibiting MC38 tumor growth and none of the treated mice survived the duration of the experiment. CTLA-4 monotherapy also showed little or no activity in inhibiting MC38 tumor growth and none of the treated mice survived the duration of the experiment. In contrast, anti-PD-1 monotherapy again showed significant activity, with 4 of 10 mice tumor free at the end of the experiment. Moreover, again combination therapy was more effective than monotherapy. For mice treated with the combination of anti-LAG-3 and anti-CTLA-4, 3 of 10 mice were tumor free at the end of the experiment and for the mice treated with the combination of anti-LAG-3 and anti-PD-1, 8 of 10 mice were tumor free at the end of the experiment.

Thus, the above-described in vivo tumor graft studies demonstrated that, for at least certain tumor models, anti-LAG antibody treatment alone resulted in significant inhibition of tumor growth in vivo. Furthermore, for multiple tumor models, the combination therapy of anti-LAG-3 antibody together with either anti-PD-1 antibody, anti-PD-L1 antibody or anti-CTLA-4 antibody resulted in even greater anti-tumor activity than monotherapy alone.

Example 7: Promotion of Autoimmunity in NOD Mice by Inhibition by Anti-LAG-3 mAb To test the ability of anti-LAG-3 antibody to stimulate an immune response, as indicated by the development of autoimmunity, the NOD mouse model of diabetes was utilized. NOD mice are known to be prone to developing autoimmune diabetes. Progression of diabetes can be followed in female NOD mice by measuring serum glucose. Thus, the effect of anti-LAG-3 treatment, alone or in combination with either immunostimulatory antibodies, on the development of diabetes in female NOD mice was examined.

Female NOD mice were treated on day 0, day 2 and day 5 with 250 μg/dose of either: (i) an IgG1 isotype control antibody; (ii) anti-LAG-3 mAb alone (C9B7W mAb); (iii) anti-PD-1 mAb alone (4H2 mAb); (iv) anti-CTLA-4 mAb alone (9D9 mAb); (v) anti-LAG-3 mAb together with anti-PD-1 mAb; or (vi) anti-LAG-3 mAb together with anti-CTLA-4. The results demonstrated with anti-LAG-3 treatment alone or anti-PD-1 treatment alone (but not anti-CTLA-4 treatment alone) increased the number of mice converting to the diabetic phenotype. Moreover, the combination treatment of anti-LAG-3 plus anti-PD-1, or anti-LAG-3 plus anti-CTLA-4, was even more effective in converting mice to the diabetic phenotype.

Thus, these results demonstrate that blockade of LAG-3 interaction with its receptor interfered with a negative immunoregulatory signal that allowed for greater immunological activity in the NOD mice, and this greater immunological activity in the LAG-3 treated mice could be enhanced by combination treatment with either anti-PD-1 or anti-CTLA-4 antibody.

Example 8: Immunohistochemistry Using Anti-LAG-3 mAbs

In this experiment, fluorescently-labeled anti-LAG-3 human antibodies were used in immunohistochemistry experiments. The following FITC-labeled, human anti-LAG-3 antibodies were used: 25F7-FITC (F:P=2.9; IgG1 version); 25F7-G4-FITC (F:P=2.7; IgG4 version); 8B7-FITC (F:P=2.6) and 26H10-FITC (F:P=3.4). A panel of lymphoid tissues, specifically tonsil (two samples), spleen (two samples) and thymus (two samples), was examined, along with pituitary tissue (four samples). LAG-3 transfected CHO cells also were used as a control. Acetone-fixed cryostat sections were used. The sections were stained with FITC-labeled anti-LAG-3 antibody (0.2-5 μg/ml), followed by staining with a rabbit anti-FITC antibody as a bridge antibody and then visualization using the rabbit EnVision™+ System Kit (Dako USA, Carpinteria, Calif.).

The results are summarized below in Table 10.

TABLE 10

Immunohistochemistry using Anti-LAG-3 mAbs

| Tissue | 25F7-FITC | 25F7-G4-FITC | 8B7-FITC | 26H10-FITC |
|---|---|---|---|---|
| CHO/LAG-3 Cells | + (strong) | + (strong) | + (strong) | + (strong) |
| Tonsil (n = 2) | + (strong; rare in scattered LC, 2/2) | + (strong; rare in scattered LC, 2/2) | + (strong; rare in scattered LC, 2/2) | + (strong; rare in scattered LC, 2/2) |
| Spleen (n = 2) | + (very weak, mainly in red pulp, 2/2) | + (very weak, mainly in red pulp, 2/2) | + (weak, mainly in red pulp, 2/2) | + (very weak, mainly in red pulp, 2/2) |
| Thymus (n = 2) | + (strong; very rare in scattered LC, 1/2) | + (strong; very rare in scattered LC, 1/2) | + (strong; very rare in scattered LC, 1/2) | + (strong; very rare in scattered LC, 1/2) |
| Pituitary (n = 4) | + (strong; occasional in adeno-hypophysis, 3/4) | + (strong; occasional in adeno-hypophysis, 3/4) | − | + (strong; occasional in adeno-hypophysis, 3/4; weak moderate, rare, 1/4) |

LC = lymphocyte;
+ = positive staining;
− = negative staining

As expected, LAG-3 expression was detected in the panel of lymphoid tissue. Additionally, two of the three anti-LAG-3 antibodies examined, 257 (IgG1 and IgG4 versions) and 26H10, exhibited retention in pituitary tissue, whereas one antibody examined, 81B7, did not show this retention in the pituitary tissue. Thus, the immunohistochemistry experiment identified two subsets of anti-LAG-3 antibodies, wherein one subset is retained in pituitary tissue and the other subset is not retained in pituitary tissue.

| SUMMARY OF SEQUENCE LISTING | |
|---|---|
| SEQ ID NO: | SEQUENCE |
| 1 | $V_H$ CDR1 a.a. 25F7 |
| 2 | $V_H$ CDR1 a.a. 26H10 |
| 3 | $V_H$ CDR1 a.a. 25E3 |
| 4 | $V_H$ CDR1 a.a. 8B7 |
| 5 | $V_H$ CDR1 a.a. 11F2 |
| 6 | $V_H$ CDR1 a.a. 17E5 |
| 7 | $V_H$ CDR2 a.a. 25F7 |
| 8 | $V_H$ CDR2 a.a. 26H10 |
| 9 | $V_H$ CDR2 a.a. 25E3 |
| 10 | $V_H$ CDR2 a.a. 8B7 |
| 11 | $V_H$ CDR2 a.a. 11F2 |
| 12 | $V_H$ CDR2 a.a. 17E5 |
| 13 | $V_H$ CDR3 a.a. 25F7 |

| SEQ ID NO: | SEQUENCE |
|---|---|
| 14 | $V_H$ CDR3 a.a. 26H10 |
| 15 | PVGVV |
| 16 | $V_H$ CDR3 a.a. 8B7 |
| 17 | $V_H$ CDR3 a.a. 11F2 |
| 18 | $V_H$ CDR3 a.a. 17E5 |
| 19 | $V_K$ CDR1 a.a. 25F7 |
| 20 | $V_K$ CDR1 a.a. 26H10 |
| 21 | $V_K$ CDR1 a.a. 25E3 |
| 22 | $V_K$ CDR1 a.a. 8B7 |
| 23 | $V_K$ CDR1 a.a. 11F2 |
| 24 | $V_K$ CDR1 a.a. 17E5 |
| 25 | $V_K$ CDR2 a.a. 25F7 |
| 26 | $V_K$ CDR2 a.a. 26H10 |
| 27 | $V_K$ CDR2 a.a. 25E3 |
| 28 | $V_K$ CDR2 a.a. 8B7 |
| 29 | $V_K$ CDR2 a.a. 11F2 |
| 30 | $V_K$ CDR2 a.a. 17E5 |
| 31 | $V_K$ CDR3 a.a. 25F7 |
| 32 | $V_K$ CDR3 a.a. 26H10 |
| 33 | $V_K$ CDR3 a.a. 25E3 |
| 34 | $V_K$ CDR3 a.a. 8B7 |
| 35 | $V_K$ CDR3 a.a. 11F2 |
| 36 | $V_K$ CDR3 a.a. 17E5 |
| 37 | $V_H$ a.a. 25F7 |
| 38 | $V_H$ a.a. 26H10 |
| 39 | $V_H$ a.a. 25E3 |
| 40 | $V_H$ a.a. 8B7 |
| 41 | $V_H$ a.a. 11F2 |
| 42 | $V_H$ a.a. 17E5 |
| 43 | $V_K$ a.a. 25F7 |
| 44 | $V_K$ a.a. 26H10 |
| 45 | $V_K$ a.a. 25E3 |
| 46 | $V_K$ a.a. 8B7 |
| 47 | $V_K$ a.a. 11F2 |
| 48 | $V_K$ a.a. 17E5 |
| 49 | $V_H$ n.t. 25F7 |
| 50 | $V_H$ n.t. 26H10 |
| 51 | $V_H$ n.t. 25E3 |
| 52 | $V_H$ n.t. 8B7 |
| 53 | $V_H$ n.t. 11F2 |
| 54 | $V_H$ n.t. 17E5 |
| 55 | $V_K$ n.t. 25F7 |
| 56 | $V_K$ n.t. 26H10 |
| 57 | $V_K$ n.t. 25E3 |
| 58 | $V_K$ n.t. 8B7 |
| 59 | $V_K$ n.t. 11F2 |
| 60 | $V_K$ n.t. 17E5 |
| 61 | $V_H$ 4-34 germline a.a. |
| 62 | $V_H$ JH5b germline a.a. |
| 63 | $V_k$ L6 germline a.a. |
| 64 | $V_k$ JK2 germline a.a. |
| 65 | $V_H$ 3-33 germline a.a. |
| 66 | $V_H$ JH6b germline a.a. |
| 67 | $V_k$ A 27 germline a.a. |
| 68 | $V_k$ JK3 germline a.a. |
| 69 | $V_H$ 3-20 germline a.a. |
| 70 | $V_H$ JH4b germline a.a. |
| 71 | $V_k$ L-18 germline a.a. |
| 72 | $V_k$ JK4 germline a.a. |
| 73 | $V_H$ 1-24 germline a.a. |
| 74 | $V_k$ JK1 germline a.a. |
| 75 | $V_k$ JK5 germline a.a. |
| 76 | PGHPLAPG |
| 77 | HPAAPSSW |
| 78 | PAAPSSWG |
| 79 | GPPAAAPGHPLAPGPHPAAPSSWGPRPRRY |
| 80 | GPPAAAPGHPLA |
| 81 | PAAAPGHPLAPG |
| 82 | AAPGHPLAPGPH |
| 83 | PGHPLAPGPHPA |
| 84 | HPLAPGPHPAAP |
| 85 | LAPGPHPAAPSS |
| 86 | PGPHPAAPSSWG |

| SUMMARY OF SEQUENCE LISTING | |
|---|---|
| SEQ ID NO: | SEQUENCE |
| 87 | PHPAAPSSWGPR |
| 88 | PAAPSSWGPRPR |
| 89 | APSSWGPRPRRY |
| 90 | GPPAPAPGHPPAPGHRPAA PYSWGPRPRRY |
| 91 | atgtgggaggctcagttcctg |
| 92 | gtcagagctgctccggctc |
| 93 | Rhesus LAG-3 clone pa23-5 a.a. |
| 94 | Rhesus LAG-3 a.a. (XM_001108923) |

What is claimed:

1. A method for treating a renal cancer in a subject comprising administering to the subject an anti-LAG-3 antibody and an anti-PD-1 antibody.

2. The method of claim 1, wherein the anti-LAG-3 antibody inhibits binding of LAG-3 to major histocompatibility (MHC) class II molecules.

3. The method of claim 1, wherein the anti-LAG-3 antibody stimulates interleukin-2 (IL-2) production in an antigen-specific T cell response.

4. The method of claim 1, wherein the anti-LAG-3 antibody is a human antibody.

5. The method of claim 1, wherein the anti-LAG-3 antibody is a chimeric or humanized antibody.

6. The method of claim 1, wherein the anti-PD-1 antibody is a human antibody.

7. The method of claim 1, wherein the anti-PD-1 antibody is a chimeric or humanized antibody.

8. The method of claim 1, wherein the anti-LAG-3 antibody and the anti-PD-1 antibody are comprised in a bispecific molecule.

9. The method of claim 8, wherein the anti-PD-1 antibody is a humanized antibody and the anti-LAG-3 antibody is a human antibody or a humanized antibody.

10. The method of claim 8, wherein the anti-PD-1 antibody is a human antibody and the anti-LAG-3 antibody is a human antibody or a humanized antibody.

11. The method of claim 1, wherein the anti-LAG-3 antibody and the anti-PD-1 antibody are administered sequentially.

12. The method of claim 1, further comprising administering a chemotherapeutic agent.

13. The method of claim 1, further comprising administering an angiogenesis inhibitor.

14. The method of claim 1, wherein the subject is a human.

15. The method of claim 1, wherein the renal cancer is metastatic renal cancer.

16. The method of claim 1, wherein the renal cancer is clear cell carcinoma.

17. A method for treating a renal cancer in a subject comprising administering to the subject an anti-LAG-3 antibody and an anti-PD-1 antibody, wherein the anti-LAG-3 antibody and the anti-PD-1 antibody are administered as separate compositions with each antibody in a pharmaceutically acceptable carrier.

18. The method of claim 17, wherein the anti-PD-1 antibody is a humanized antibody and the anti-LAG-3 antibody is a human antibody or a humanized antibody.

19. The method of claim 17, wherein the anti-PD-1 antibody is a human antibody and the anti-LAG-3 antibody is a human antibody or a humanized antibody.

20. A method for treating a renal cancer in a subject comprising administering to the subject an anti-LAG-3 antibody and an anti-PD-1 antibody, wherein the anti-LAG-3 antibody and the anti-PD-1 antibody are administered as a single composition in a pharmaceutically acceptable carrier.

21. The method of claim 20, wherein the anti-PD-1 antibody is a humanized antibody and the anti-LAG-3 antibody is a human antibody or a humanized antibody.

22. The method of claim 20, wherein the anti-PD-1 antibody is a human antibody and the anti-LAG-3 antibody is a human antibody or a humanized antibody.

* * * * *